(12) United States Patent
Wittamer et al.

(10) Patent No.: US 8,003,347 B2
(45) Date of Patent: Aug. 23, 2011

(54) NUCLEIC ACIDS ENCODING CHEMERINR LIGANDS

(75) Inventors: Valeria Wittamer, Waterloo (BE); Jean-Francois Mirjolet, Dijon (FR); Isabelle Migeotte, Brussels (BE); David Communi, Braine le Chateau (BE); Alberto Mantovani, Milan (IT); Silvano Sozzani, Bovezzo (IT); Marisa Vulcano, Milan (IT); Jean-Denis Franssen, Nivelles (BE); Stephane Brezillon, Dilbeek (BE); Michel Detheux, Marche-lez-Ecausines (BE); Gilbert Vassart, Brussels (BE); Marc Parmentier, Beerzel (BE); Emmanuel Lepoul, Cessy (FR)

(73) Assignee: Euroscreen S.A., Brussels (BE)

( * ) Notice: Subject to any disclaimer, the term of this patent is extended or adjusted under 35 U.S.C. 154(b) by 153 days.

(21) Appl. No.: 12/184,783

(22) Filed: Aug. 1, 2008

(65) Prior Publication Data

US 2009/0081729 A1 Mar. 26, 2009

Related U.S. Application Data

(60) Division of application No. 10/603,566, filed on Jun. 25, 2003, now Pat. No. 7,419,658, which is a continuation-in-part of application No. 10/201,187, filed on Jul. 23, 2002, now abandoned, which is a continuation-in-part of application No. 09/905,253, filed on Jul. 13, 2001, now abandoned.

(60) Provisional application No. 60/303,858, filed on Jul. 9, 2001.

(51) Int. Cl.
*C12N 15/00* (2006.01)
*C12N 15/85* (2006.01)
*C12N 15/19* (2006.01)
*C07H 21/04* (2006.01)
*C07K 14/52* (2006.01)

(52) U.S. Cl. ........ 435/69.1; 435/325; 536/23.1; 530/351

(58) Field of Classification Search ........................ None
See application file for complete search history.

(56) References Cited

U.S. PATENT DOCUMENTS

| 5,948,664 | A | 9/1999 | Williams et al. |
| 6,822,072 | B1 | 11/2004 | Edwards et al. |
| 2003/0022188 | A1 | 1/2003 | Macina et al. |
| 2003/0096299 | A1 | 5/2003 | Wittamer et al. |
| 2005/0084936 | A1 | 4/2005 | Lal et al. |

FOREIGN PATENT DOCUMENTS

| WO | WO/00/31258 | 6/2000 |
| WO | WO/02/03798 | 1/2002 |

OTHER PUBLICATIONS

Adams et al.; "1,25 Dihydroxyvitamin D3 and Dexamethasone Induce the Cyclooxygenase 1 Gene in Osteoclast-Supporting Stromal Cells"; (199); J. of Cellular Biochemistry; 74:587-595.
Nagpal, et al.; "Tazarotene-induced gene 2 (TIG2), a novel retinoid-responsive gene in skin"; (1997); J. Invest. Dermatol.; 109: 91-95.
Samson et al.; "Chem R23, a putative chemoattractant receptor is expressed in monocyte-derived denritic cells and macrophages and is a coreceptor for SIV and some primary HIV-1 strains"; (1998); Eur. J. Immunology; 28: 1689-1700.
Methner, et al.; "A novel G protein-coupled receptor with homology to neuropeptdie and chemoattractant receptors expressed during bone development"; (1997); Biochemical and Biophysical Research Communications; 233: 336-342.
Kotani et al. "the metastasis-suppressor gene KiSS-1 encodes kisspeptins, the natural ligans of the orphan G protein-coupled receptor GPR54", (2001), J. Biol. Chem. 276: 34631-34636.
Joost, P. et al. "Phylogenetic analysis of 277 human G-protein-coupled receptors as a tool for the prediction of orphan receptor ligands", (2002), Genome Biology 3, 0063.1-0063.16.
Lee et al., "Orphan G protein-coupled receptors in the CNS", (2001), Curr. Opin. Pharacol., 1:31-39.
Im et al., "Orphan G protein-coupled receptors and beyond", (2002), Jpn. J. Pharmacolo., 90: 101-106.
Communi et al., "Receptors responsive to extracellular pyrimidine nucleotides" Trends in Pharmacological Sciences, 18(3): 83-86, Mar. 1, 1997.
Communi et al., "Cloning of a human purinergic P2Y receptor coupled to phospholipase C and adenyl cyclase" J. Biol. Chem. 272(51):31969-31973.
Owman et al., "Molecular cloning and tissue distribution of a novel chemo-attractant-like receptor," Biochem Biophys Res. Commun., Dec 18, 1997:241(2)390-394.
International Search Report, Oct. 22, 2003, PCT/EP2002/07647.
Wittamer et al., Specific recruitment of antigen-presenting cells by chemerin, a novel processed ligand from human inflammatory fluids, the journal of experimental medicine, Oct. 6, 2003, vol. 198, No. 7, pp. 977-985.
Wittamer et al., "The C-terminal nanopeptide of mature chemerin activates the chemerin receptor with low nanomolar potency," The J. of Biological Chemistry, Mar. 12, 2004, vol. 279, No. 11, pp. 9956-9962.
International Search Report, Oct. 25, 2005, PCT/EP2004/006945.
Gantz et al., Moleular Cloning of a Novel Receptor (cmklr1) With Homology to the Chemotactic Factor Receptors, Cytogenetics and Cell Genetics, vol. 74, pp. 286-290 (1996).
Zabel et al., Chemoattractants, Extracellular Proteases, and the Integrated Host Defense Response, Experimental Hematology, vol. 34, pp. 1021-1032 (2006).
Duvic et al., Molecular Mechanisms of Tazarotene Action in Psoriasis, J. Am. Adac. Dermatol., vol. 37, pp. S18-24, Aug. 1997.

*Primary Examiner* — Ruixiang Li
(74) *Attorney, Agent, or Firm* — Edwards Angell Palmer & Dodge LLP; Kathleen Williams; Amy DeCloux

(57) ABSTRACT

The present invention relates to a G-protein coupled receptor and a novel ligand therefor. The invention provides screening assays for the identification of candidate compounds which modulate the activity of the G-protein coupled receptor, as well as assays useful for the diagnosis and treatment of a disease or disorder related to the dysregulation of G-protein coupled receptor signaling.

10 Claims, 41 Drawing Sheets

Figure 1: Nucleotide (SEQ ID NO: 1) and deduced amino acid sequence of human ChemerinR (AC075748)

```
  1   M   E   D   E   D   Y   N   T   S   I   S   Y   G   D   E    15
175   ATG GAG GAT GAA GAT TAC AAC ACT TCC ATC AGT TAC GGT GAT GAA  219

16   Y   P   D   Y   L   D   S   I   V   V   L   E   D   L   S    30
220   TAC CCT GAT TAT TTA GAC TCC ATT GTG GTT TTG GAG GAC TTA TCC  264

31   P   L   E   A   R   V   T   R   I   F   L   V   V   V   Y    45
265   CCC TTG GAA GCC AGG GTG ACC AGG ATC TTC CTG GTG GTG GTC TAC  309

46   S   I   V   C   F   L   G   I   L   G   N   G   L   V   I    60
310   AGC ATC GTC TGC TTC CTC GGG ATT CTG GGC AAT GGT CTG GTG ATC  354

61   I   I   A   T   F   K   M   K   K   T   V   N   M   V   W    75
355   ATC ATT GCC ACC TTC AAG ATG AAG AAG ACA GTG AAC ATG GTC TGG  399

76   F   L   N   L   A   V   A   D   F   L   F   N   V   F   L    90
400   TTC CTC AAC CTG GCA GTG GCA GAT TTC CTG TTC AAC GTC TTC CTC  444

91   P   I   H   I   T   Y   A   A   M   D   Y   H   W   V   F   105
445   CCA ATC CAT ATC ACC TAT GCC GCC ATG GAC TAC CAC TGG GTT TTC  489

106   G   T   A   M   C   K   I   S   N   F   L   L   I   H   N   120
490   GGG ACA GCC ATG TGC AAG ATC AGC AAC TTC CTT CTC ATC CAC AAC  534

121   M   F   T   S   V   F   L   L   T   I   I   S   S   D   R   135
535   ATG TTC ACC AGC GTC TTC CTG CTG ACC ATC ATC AGC TCT GAC CGC  579

136   C   I   S   V   L   L   P   V   W   S   Q   N   H   R   S   150
580   TGC ATC TCT GTG CTC CTC CCT GTC TGG TCC CAG AAC CAC CGC AGC  624

151   V   R   L   A   Y   M   A   C   M   V   I   W   V   L   A   165
625   GTT CGC CTG GCT TAC ATG GCC TGC ATG GTC ATC TGG GTC CTG GCT  669

166   F   F   L   S   S   P   S   L   V   F   R   D   T   A   N   180
670   TTC TTC TTG AGT TCC CCA TCT CTC GTC TTC CGG GAC ACA GCC AAC  714

181   L   H   G   K   I   S   C   F   N   N   F   S   L   S   T   195
715   CTG CAT GGG AAA ATA TCC TGC TTC AAC AAC TTC AGC CTG TCC ACA  759

196   P   G   S   S   S   W   P   T   H   S   Q   M   D   P   V   210
760   CCT GGG TCT TCC TCG TGG CCC ACT CAC TCC CAA ATG GAC CCT GTG  804

211   G   Y   S   R   H   M   V   V   T   V   T   R   F   L   C   225
805   GGG TAT AGC CGG CAC ATG GTG GTG ACT GTC ACC CGC TTC CTC TGT  849

226   G   F   L   V   P   V   L   I   I   T   A   C   Y   L   T   240
850   GGC TTC CTG GTC CCA GTC CTC ATC ATC ACA GCT TGC TAC CTC ACC  894

241   I   V   C   K   L   Q   R   N   R   L   A   K   T   K   K   255
895   ATC GTC TGC AAA CTG CAG CGC AAC CGC CTG GCC AAG ACC AAG AAG  939

```
     940 CCC TTC AAG ATT ATT GTG ACC ATC ATC ATT ACC TTC TTC CTC TGC  984

271  W   C   P   Y   H   T   L   N   L   L   E   L   H   H   T   285
     985 TGG TGC CCC TAC CAC ACA CTC AAC CTC CTA GAG CTC CAC CAC ACT 1029

286  A   M   P   G   S   V   F   S   L   G   L   P   L   A   T   300
    1030 GCC ATG CCT GGC TCT GTC TTC AGC CTG GGT TTG CCC CTG GCC ACT 1074

301  A   L   A   I   A   N   S   C   M   N   P   I   L   Y   V   315
    1075 GCC CTT GCC ATT GCC AAC AGC TGC ATG AAC CCC ATT CTG TAT GTT 1119

316  F   M   G   Q   D   F   K   K   F   K   V   A   L   F   S   330
    1120 TTC ATG GGT CAG GAC TTC AAG AAG TTC AAG GTG GCC CTC TTC TCT 1164

331  R   L   V   N   A   L   S   E   D   T   G   H   S   S   Y   345
    1165 CGC CTG GTC AAT GCT CTA AGT GAA GAT ACA GGC CAC TCT TCC TAC 1209

346  P   S   H   R   S   F   T   K   M   S   S   M   N   E   R   360
    1210 CCC AGC CAT AGA AGC TTT ACC AAG ATG TCA TCA ATG AAT GAG AGG 1254

361  T   S   M   N   E   R   E   T   G   M   L   *               372
    1255 ACT TCT ATG AAT GAG AGG GAG ACC GGC ATG CTT TGA             1290
```

Figure 2: Amino acid sequence of human ChemerinR (371 amino acids) (SEQ ID NO 2).

MEDEDYNTSISYGDEYPDYLDSIVVLEDLSPLEARVTRIF<u>LVVVYSIVCFLGILGNGLVIIIAT</u>
<u>F</u>KMKKTVNMVW<u>FLNLAVADFLFNVFLPIHITYAAMD</u>YHWVFGTAMCK<u>ISNFLLIHNMFTSVFLL</u>
<u>TIISSDRCISVLLPVWSQNHRSVR</u>LA<u>YMACMVIWVLAFFLSSPSLVF</u>RDTANLHGKISCFNNFS
LSTPGSSSWPTHSQMDPVGYSRHMVVTVTR<u>FLCGFLVPVLIITACYLTIVC</u>KLQRNRLAKTKKP
FK<u>IIVTIIITFFLCWCPYHTLNLL</u>ELHHTAMPGSVFSLG<u>LPLATALAIANSCMNP</u>ILYVFMGQD
FKKFKVALFSRLVNALSEDTGHSSYP*SHR*SFTKMSSMNERTSMNERETGML

Figure 3: Nucleotide and deduced amino acid sequence of mouse dez (AC u79525 – SEQ ID NOs:3 and 4, respectively)

```
   1   M   E   Y   D   A   Y   N   D   S   G   I   Y   D   D   E    15
 265 ATG GAG TAC GAC GCT TAC AAC GAC TCC GGC ATC TAT GAT GAT GAG   309

16   Y   S   D   G   F   G   Y   F   V   D   L   E   E   A   S    30
 310 TAC TCT GAT GGC TTT GGC TAC TTT GTG GAC TTG GAG GAG GCG AGT   354

31   P   W   E   A   K   V   A   P   V   F   L   V   V   I   Y    45
 355 CCG TGG GAG GCC AAG GTG GCC CCG GTC TTC CTG GTG GTG ATC TAC   399

46   S   L   V   C   F   L   G   L   L   G   N   G   L   V   I    60
 400 AGC TTG GTG TGC TTC CTC GGT CTC CTA GGC AAC GGC CTG GTG ATT   444

61   V   I   A   T   F   K   M   K   K   T   V   N   T   V   W    75
 445 GTC ATC GCC ACC TTC AAG ATG AAG AAG ACC GTG AAC ACT GTG TGG   489

76   F   V   N   L   A   V   A   D   F   L   F   N   I   F   L    90
 490 TTT GTC AAC CTG GCT GTG GCC GAC TTC CTG TTC AAC ATC TTT TTG   534

91   P   M   H   I   T   Y   A   A   M   D   Y   H   W   V   F   105
 535 CCG ATG CAC ATC ACC TAC GCG GCC ATG GAC TAC CAC TGG GTG TTC   579

106   G   K   A   M   C   K   I   S   N   F   L   L   S   H   N   120
 580 GGG AAG GCC ATG TGC AAG ATC AGC AAC TTC TTG CTC AGC CAC AAC   624

121   M   Y   T   S   V   F   L   L   T   V   I   S   F   D   R   135
 625 ATG TAC ACC AGC GTC TTC CTG CTG ACT GTC ATC AGC TTT GAC CGC   669

136   C   I   S   V   L   L   P   V   W   S   Q   N   H   R   S   150
 670 TGC ATC TCC GTG CTG CTC CCC GTC TGG TCC CAG AAC CAC CGC AGC   714

151   I   R   L   A   Y   M   T   C   S   A   V   W   V   L   A   165
 715 ATC CGC CTG GCC TAC ATG ACC TGC TCG GCC GTC TGG GTC CTG GCT   759

166   F   F   L   S   S   P   S   L   V   F   R   D   T   A   N   180
 760 TTC TTC TTG AGC TCC CCG TCC CTT GTC TTC CGG GAC ACC GCC AAC   804

181   I   H   G   K   I   T   C   F   N   N   F   S   L   A   A   195
 805 ATT CAT GGG AAG ATA ACC TGC TTC AAC AAC TTC AGC TTG GCC GCG   849

196   P   E   S   S   P   H   P   A   H   S   Q   V   V   S   T   210
 850 CCT GAG TCC TCC CCA CAT CCC GCC CAC TCG CAA GTA GTT TCC ACA   894

211   G   Y   S   R   H   V   A   V   T   V   T   R   F   L   C   225
 895 GGG TAC AGC AGA CAC GTG GCG GTC ACT GTC ACC CGC TTC CTT TGC   939

226   G   F   L   I   P   V   F   I   I   T   A   C   Y   L   T   240
 940 GGC TTC CTG ATC CCC GTC TTC ATC ATC ACG GCC TGC TAC CTT ACC   984

241   I   V   F   K   L   Q   R   N   R   L   A   K   N   K   K   255
 985 ATC GTC TTC AAG CTG CAG CGC AAC CGC CTG GCC AAG AAC AAG AAG  1029

256   P   F   K   I   I   I   T   I   I   I   T   F   F   L   C   270
1030 CCC TTC AAG ATC ATC ATC ACC ATC ATC ATC ACC TTC TTC CTC TGC  1074

271   W   C   P   Y   H   T   L   Y   L   L   E   L   H   H   T   285
1075 TGG TGC CCC TAC CAC ACC CTC TAC CTG CTG GAG CTC CAC CAC ACA  1119

286   A   V   P   S   S   V   F   S   L   G   L   P   L   A   T   300
1120 GCT GTG CCA AGC TCT GTC TTC AGC CTG GGG CTA CCC CTG GCC ACG  1164
```

Figure 3 Continued

```
301    A    V    A    I    A    N    S    C    M    N    P    I    L    Y    V      315
1165  GCC  GTC  GCC  ATC  GCC  AAC  AGC  TGC  ATG  AAC  CCC  ATT  CTG  TAC  GTC    1209

316    F    M    G    H    D    F    R    K    F    K    V    A    L    F    S      330
1210  TTC  ATG  GGC  CAC  GAC  TTC  AGA  AAA  TTC  AAG  GTG  GCC  CTC  TTC  TCC    1254

331    R    L    A    N    A    L    S    E    D    T    G    P    S    S    Y      345
1255  CGC  CTG  GCC  AAC  GCC  CTG  AGT  GAG  GAC  ACA  GGC  CCC  TCC  TCC  TAC    1299

346    P    S    H    R    S    F    T    K    M    S    S    L    N    E    K      360
1300  CCC  AGT  CAC  AGG  AGC  TTC  ACC  AAG  ATG  TCG  TCT  TTG  AAT  GAG  AAG    1344

361    A    S    V    N    E    K    E    T    S    T    L    *                      372
1345  GCT  TCG  GTG  AAT  GAG  AAG  GAG  ACC  AGT  ACC  CTC  TGA                    1380
```

Figure 4: Nucleotide and deduced amino acid sequence of rat G-protein coupled chemoattractant-1 (AC NM_022218 - SEQ ID Nos: 5 and 6, respectively).

```
  1   M   E   Y   E   G   Y   N   D   S   S   I   Y   G   E   E    15
  1 ATG GAG TAC GAG GGT TAC AAC GAC TCC AGC ATC TAC GGT GAG GAG     45

16   Y   S   D   G   S   D   Y   I   V   D   L   E   E   A   G    30
 46 TAT TCT GAC GGC TCG GAC TAC ATC GTG GAC TTG GAG GAG GCG GGT     90

31   P   L   E   A   K   V   A   E   V   F   L   V   V   I   Y    45
 91 CCA CTG GAG GCC AAG GTG GCC GAG GTC TTC CTG GTG GTA ATC TAC    135

46   S   L   V   C   F   L   G   I   L   G   N   G   L   V   I    60
136 AGC TTG GTG TGC TTC CTC GGG ATC CTA GGC AAT GGC CTG GTG ATT    180

61   V   I   A   T   F   K   M   K   K   T   V   N   T   V   W    75
181 GTC ATC GCC ACC TTC AAG ATG AAG AAG ACG GTG AAC ACC GTG TGG    225

76   F   V   N   L   A   V   A   D   F   L   F   N   I   F   L    90
226 TTT GTC AAC CTG GCC GTG GCT GAC TTC CTG TTC AAC ATC TTC TTG    270

91   P   I   H   I   T   Y   A   A   M   D   Y   H   W   V   F   105
271 CCC ATC CAC ATC ACC TAT GCC GCT ATG GAC TAC CAC TGG GTG TTC    315

106   G   K   A   M   C   K   I   S   S   F   L   L   S   H   N   120
316 GGG AAA GCC ATG TGC AAG ATT AGT AGC TTT CTG CTA AGC CAC AAC    360

121   M   Y   T   S   V   F   L   L   T   V   I   S   F   D   R   135
361 ATG TAC ACC AGC GTC TTC CTG CTC ACT GTC ATC AGC TTC GAC CGC    405

136   C   I   S   V   L   L   P   V   W   S   Q   N   H   R   S   150
406 TGC ATC TCC GTG CTC CTC CCC GTC TGG TCC CAG AAC CAC CGC AGC    450

151   V   R   L   A   Y   M   T   C   V   V   V   W   V   W   L   165
451 GTG CGT CTG GCC TAC ATG ACC TGC GTG GTT GTC TGG GTC TGG CTT    495

166   S   S   E   S   P   P   S   L   V   F   G   H   V   S   T   180
496 TCT TCT GAG TCT CCC CCG TCC CTC GTC TTC GGA CAC GTC AGC ACC    540

181   S   H   G   K   I   T   C   F   N   N   F   S   L   A   A   195
541 AGC CAC GGG AAG ATA ACC TGC TTC AAC AAC TTC AGC CTG GCG GCG    585

196   P   E   P   F   S   H   S   T   H   P   R   T   D   P   V   210
586 CCC GAG CCT TTC TCT CAT TCC ACC CAC CCG CGA ACA GAC CCG GTA    630

211   G   Y   S   R   H   V   A   V   T   V   T   R   F   L   C   225
631 GGG TAC AGC AGA CAT GTG GCG GTC ACC GTC ACC CGC TTC CTC TGT    675

226   G   F   L   I   P   V   F   I   I   T   A   C   Y   L   T   240
676 GGC TTC CTG ATC CCC GTC TTC ATC ATC ACG GCC TGT TAC CTC ACC    720

241   I   V   F   K   L   Q   R   N   R   Q   A   K   T   K   K   255
721 ATC GTC TTC AAG TTG CAG CGC AAC CGC CAG GCC AAG ACC AAG AAG    765

256   P   F   K   I   I   I   T   I   I   I   T   F   F   L   C   270
766 CCC TTC AAG ATC ATC ATC ACC ATC ATC ATC ACC TTC TTC CTC TGC    810

271   W   C   P   Y   H   T   L   Y   L   L   E   L   H   H   T   285
811 TGG TGC CCC TAC CAC ACA CTC TAC CTG CTG GAG CTC CAC CAC ACG    855

```
 856 GCT GTG CCA GCC TCT GTC TTC AGC CTG GGA CTG CCC CTG GCC ACA      900

301  A   V   A   I   A   N   S   C   M   N   P   I   L   Y   V      315
 901 GCC GTC GCC ATC GCC AAC AGC TGT ATG AAC CCC ATC CTG TAC GTC      945

316  F   M   G   H   D   F   K   K   F   K   V   A   L   F   S      330
 946 TTC ATG GGC CAC GAC TTC AAA AAA TTC AAG GTG GCC CTT TTC TCC      990

331  R   L   V   N   A   L   S   E   D   T   G   P   S   S   Y      345
 991 CGC CTG GTG AAT GCC CTG AGC GAG GAC ACA GGA CCC TCC TCC TAC     1035

346  P   S   H   R   S   F   T   K   M   S   S   L   I   E   K      360
1036 CCC AGT CAC AGG AGC TTC ACC AAG ATG TCC TCA TTG ATT GAG AAG     1080

361  A   S   V   N   E   K   E   T   S   T   L   *                  372
1081 GCT TCA GTG AAT GAG AAA GAG ACC AGC ACC CTC TGA                 1116
```

Figure 5: Alignment of ChemerinR
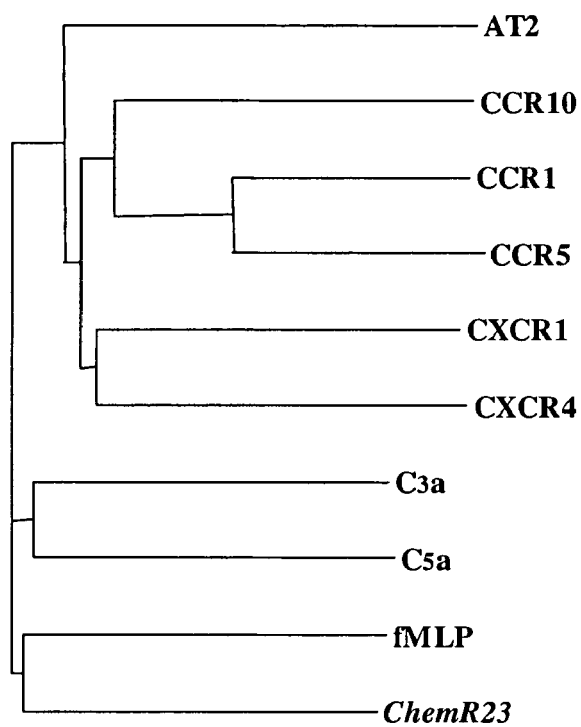

Figure 6: Nucleotide and deduced amino acid sequence of human Preprochemerin (AC Q99969 - SEQ ID Nos: 7 and 8, respectively)

```
  1 M   R   R   L   L   I   P   L   A   L   W   L   G   A   V    15
 97 ATG CGA CGG CTG CTG ATC CCT CTG GCC CTG TGG CTG GGT GCG GTG  141

16 G   V   G   V   A   E   L   T   E   A   Q   R   R   G   L    30
142 GGC GTG GGC GTC GCC GAG CTC ACG GAA GCC CAG CGC CGG GGC CTG  186

31 Q   V   A   L   E   E   F   H   K   H   P   P   V   Q   W    45
187 CAG GTG GCC CTG GAG GAA TTT CAC AAG CAC CCG CCC GTG CAG TGG  231

46 A   F   Q   E   T   S   V   E   S   A   V   D   T   P   F    60
232 GCC TTC CAG GAG ACC AGT GTG GAG AGC GCC GTG GAC ACG CCC TTC  276

61 P   A   G   I   F   V   R   L   E   F   K   L   Q   Q   T    75
277 CCA GCT GGA ATA TTT GTG AGG CTG GAA TTT AAG CTG CAG CAG ACA  321

76 S   C   R   K   R   D   W   K   K   P   E   C   K   V   R    90
322 AGC TGC CGG AAG AGG GAC TGG AAG AAA CCC GAG TGC AAA GTC AGG  366

91 P   N   G   R   K   R   K   C   L   A   C   I   K   L   G   105
367 CCC AAT GGG AGG AAA CGG AAA TGC CTG GCC TGC ATC AAA CTG GGC  411

106 S   E   D   K   V   L   G   R   L   V   H   C   P   I   E   120
412 TCT GAG GAC AAA GTT CTG GGC CGG TTG GTC CAC TGC CCC ATA GAG  456

121 T   Q   V   L   R   E   A   E   E   H   Q   E   T   Q   C   135
457 ACC CAA GTT CTG CGG GAG GCT GAG GAG CAC CAG GAG ACC CAG TGC  501

136 L   R   V   Q   R   A   G   E   D   P   H   S   F   Y   F   150
502 CTC AGG GTG CAG CGG GCT GGT GAG GAC CCC CAC AGC TTC TAC TTC  546

151 P   G   Q   F   A   F   S   K   A   L   P   R   S   *       164
547 CCT GGA CAG TTC GCC TTC TCC AAG GCC CTG CCC CGC AGC TAA      588
```

Figure 7: Nucleotide and deduced amino acid sequence of mouse Preprochemerin (SEQ ID Nos: 9 and 10, respectively)

```
  1   M   K   C   L   L   I   S   L   A   L   W   L   G   T   V    15
102  ATG AAG TGC TTG CTG ATC TCC CTA GCC CTA TGG CTG GGC ACA GTG   146

16   G   T   R   G   T   E   P   E   L   S   E   T   Q   R   R    30
147  GGC ACA CGT GGG ACA GAG CCC GAA CTC AGC GAG ACC CAG CGC AGG   191

31   S   L   Q   V   A   L   E   E   F   H   K   H   P   P   V    45
192  AGC CTA CAG GTG GCT CTG GAG GAG TTC CAC AAA CAC CCA CCT GTG   236

46   Q   L   A   F   Q   E   I   G   V   D   R   A   E   E   V    60
237  CAG TTG GCC TTC CAA GAG ATC GGT GTG GAC AGA GCT GAA GAA GTG   281

61   L   F   S   A   G   T   F   V   R   L   E   F   K   L   Q    75
282  CTC TTC TCA GCT GGC ACC TTT GTG AGG TTG GAA TTT AAG CTC CAG   326

76   Q   T   N   C   P   K   K   D   W   K   K   P   E   C   T    90
327  CAG ACC AAC TGC CCC AAG AAG GAC TGG AAA AAG CCG GAG TGC ACA   371

91   I   K   P   N   G   R   R   R   K   C   L   A   C   I   K   105
372  ATC AAA CCA AAC GGG AGA AGG CGG AAA TGC CTG GCC TGC ATT AAA   416

106   M   D   P   K   G   K   I   L   G   R   I   V   H   C   P   120
417  ATG GAC CCC AAG GGT AAA ATT CTA GGC CGG ATA GTC CAC TGC CCA   461

121   I   L   K   Q   G   P   Q   D   P   Q   E   L   Q   C   I   135
462  ATT CTG AAG CAA GGG CCT CAG GAT CCT CAG GAG TTG CAA TGC ATT   506

136   K   I   A   Q   A   G   E   D   P   H   G   Y   F   L   P   150
507  AAG ATA GCA CAG GCT GGC GAA GAC CCC CAC GGC TAC TTC CTA CCT   551

151   G   Q   F   A   F   S   R   A   L   R   T   K   *           163
552  GGA CAG TTT GCC TTC TCC AGG GCC CTG AGA ACC AAA TAA           590
```

Figure 8: Nucleotide and deduced amino acid sequence of human Prochemerin (SEQ ID Nos: 11 and 12 respectively)

```
  1 E   L   T   E   A   Q   R   R   G   L   Q   V   A   L   E  15
  1 GAG CTC ACG GAA GCC CAG CGC CGG GGC CTG CAG GTG GCC CTG GAG 45

16 E   F   H   K   H   P   P   V   Q   W   A   F   Q   E   T  30
 46 GAA TTT CAC AAG CAC CCG CCC GTG CAG TGG GCC TTC CAG GAG ACC 90

31 S   V   E   S   A   V   D   T   P   F   P   A   G   I   F  45
 91 AGT GTG GAG AGC GCC GTG GAC ACG CCC TTC CCA GCT GGA ATA TTT 135

46 V   R   L   E   F   K   L   Q   Q   T   S   C   R   K   R  60
136 GTG AGG CTG GAA TTT AAG CTG CAG CAG ACA AGC TGC CGG AAG AGG 180

61 D   W   K   K   P   E   C   K   V   R   P   N   G   R   K  75
181 GAC TGG AAG AAA CCC GAG TGC AAA GTC AGG CCC AAT GGG AGG AAA 225

76 R   K   C   L   A   C   I   K   L   G   S   E   D   K   V  90
226 CGG AAA TGC CTG GCC TGC ATC AAA CTG GGC TCT GAG GAC AAA GTT 270

91 L   G   R   L   V   H   C   P   I   E   T   Q   V   L   R 105
271 CTG GGC CGG TTG GTC CAC TGC CCC ATA GAG ACC CAA GTT CTG CGG 315

106 E   A   E   E   H   Q   E   T   Q   C   L   R   V   Q   R 120
316 GAG GCT GAG GAG CAC CAG GAG ACC CAG TGC CTC AGG GTG CAG CGG 360

121 A   G   E   D   P   H   S   F   Y   F   P   G   Q   F   A 135
361 GCT GGT GAG GAC CCC CAC AGC TTC TAC TTC CCT GGA CAG TTC GCC 405

136 F   S   K   A   L   P   R   S                              143
406 TTC TCC AAG GCC CTG CCC CGC AGC                             429
```

Figure 9: Nucleotide and deduced amino acid sequence of human Chemerin (SEQ ID Nos 13 and 14 respectively)

```
  1 E   L   T   E   A   Q   R   R   G   L   Q   V   A   L   E   15
  1 GAG CTC ACG GAA GCC CAG CGC CGG GGC CTG CAG GTG GCC CTG GAG 45

16 E   F   H   K   H   P   P   V   Q   W   A   F   Q   E   T   30
 46 GAA TTT CAC AAG CAC CCG CCC GTG CAG TGG GCC TTC CAG GAG ACC 90

31 S   V   E   S   A   V   D   T   P   F   P   A   G   I   F   45
 91 AGT GTG GAG AGC GCC GTG GAC ACG CCC TTC CCA GCT GGA ATA TTT 135

46 V   R   L   E   F   K   L   Q   Q   T   S   C   R   K   R   60
136 GTG AGG CTG GAA TTT AAG CTG CAG CAG ACA AGC TGC CGG AAG AGG 180

61 D   W   K   K   P   E   C   K   V   R   P   N   G   R   K   75
181 GAC TGG AAG AAA CCC GAG TGC AAA GTC AGG CCC AAT GGG AGG AAA 225

76 R   K   C   L   A   C   I   K   L   G   S   E   D   K   V   90
226 CGG AAA TGC CTG GCC TGC ATC AAA CTG GGC TCT GAG GAC AAA GTT 270

91 L   G   R   L   V   H   C   P   I   E   T   Q   V   L   R   105
271 CTG GGC CGG TTG GTC CAC TGC CCC ATA GAG ACC CAA GTT CTG CGG 315

106 E   A   E   E   H   Q   E   T   Q   C   L   R   V   Q   R   120
316 GAG GCT GAG GAG CAC CAG GAG ACC CAG TGC CTC AGG GTG CAG CGG 360

121 A   G   E   D   P   H   S   F   Y   F   P   G   Q   F   A   135
361 GCT GGT GAG GAC CCC CAC AGC TTC TAC TTC CCT GGA CAG TTC GCC 405

136 F   S                                                       137
406 TTC TCC                                                     411
```

Figure 10: Amino acid sequence alignment of human (SEQ ID NO: 8) and mouse Preprochemerin (SEQ ID NO: 10). Identical and similar residues are shaded.

```
                 *        20         *        40         *
HUMAN : MRRLLIPLALWLGAVGVG--VAELTEAQRRGLQVALEEFHKHPPVQWAFQETSVE :  53
MOUSE : MKCLLISLALWLGTWGTRGTEPELSETQRRSLQVALEEFHKHPPVQLAFQEIGVD :  55

60         *        80         *        100        *
HUMAN : SAVDTPFPAGIFVRLEFKLQQTSCRKRDWKKPECKVRPNGRKRKCLACIKLGSED : 108
MOUSE : RAEEVLFSAGTFVRLEFKLQQTNCPKKDWKKPECTIKPNGRRRKCLACIKMDPKG : 110

120         *       140         *       160
HUMAN : KVLGRLVHCPIETQVLREAEEHQETQCLRVQRAGEDPHSFYFPGQFAFSKALPRS : 163
MOUSE : KILGRIVHCPILKC---GPQDPQELQCIKIAQAGEDPHGYFLPGQFAFSRALRTK : 162
```

Figure 11. Sequence Alignment of Chemerin Polypeptide Sequences

```
       1                                                                50 mus    MKCLLISLAL  WLGTVGTRGT  EPELSETQRR  SLQVALEEFH  KHPPVQLAFQ
   rat    MKCLLISLAL  WLGTADIHGT  ELELSETQRR  GLQVALEEFH  RHPPVQWAFQ
 human    MRRLLIPLAL  WLGAVGV..G  VAELTEAQRR  GLQVALEEFH  KHPPVQWAFQ
   sus    MWQLLLPLAL  WLGTMGL..G  RAELTAAQLR  GLQVALEEFH  KHPPVQWAFR
   bos    MWQLLLPLAL  GLGTMGL..G  RAELTTAQHR  GLQVALEEFH  KHPPVLWAFQ
gallus    ~RAVGMKLLL  GIAVVVLALA  DAGQSPLQRR  VVKDVLDYFH  SRSNVQFLFR 51                                                               100 mus    EIGVDRAEEV  LFSAGTFVRL  EFKLQQTNCP  KKDWKKPECT  IKPNGRRRKC
   rat    EIGVDSADDL  FFSAGTFVRL  EFKLQQTSCL  KKDWKKPECT  IKPNGRKRKC
 human    ETSVESAVDT  PFPAGIFVRL  EFKLQQTSCR  KRDWKKPECK  VRPNGRKRKC
   sus    ETGVNSAMDT  PFPAGTFVRL  EFKLQQTSCR  KRDWKKAECK  VKPNGRKRKC
   bos    VTSVDNAADT  LFPAGQFVRL  EFKLQQTSCR  KKDWRKEDCK  VKPNGRKRKC
gallus    EQSVEGAVER  VDSSGTFVQL  HLNLAQTACR  KQAQRKQNCR  IMENRRKPVC 101                                                              150 mus    LACIKMDPKG  ..KILGRIVH  C.PILKQGP.  Q..DPQELQC  IKIAQAGEDP
   rat    LACIKLDPKG  ..KVLGRMVH  C.PILKQGPQ  Q..EPQESQC  SKIAQAGEDS
 human    LACIKLGSED  ..KVLGRLVH  C.PIETQVLR  EAEEHQETQC  LRVQRAGEDP
   sus    LACIKLNSED  ..KVLGRMVH  C.PIETQVQR  EPEERQEAQC  SRVERAGEDP
   bos    LACIKLDSKD  ..QVLGRMVH  C.PIQTQVQR  ELDDAQDAQC  SRVERAGEDP
gallus    LACYKFDSSD  VPKVLDKYYN  CGPSHHLAMK  DIKHRDEAEC  RAVEEAGKTS
```

Figure 11 Continued

```
           151                168
   mus    HGYFLPGQFA FSRALRTK (SEQ ID NO: 10)
   rat    RIYFFPGQFA FSRAL    (SEQ ID NO: 76)
 human    HSFYFPGQFA FSKALPRS (SEQ ID NO: 8)
   sus    HSYYFPGQFA FFKALPPS (SEQ ID NO: 77)
   bos    HSYYLPGQFA FIKAL    (SEQ ID NO: 78)
gallus    DVLYLPGMFA FSKGLP   (SEQ ID NO: 79)
```

Identities :

|  | bos.pep | mus.pep | sus.pep | gallus | rat.pep |
|---|---|---|---|---|---|
| human.pep | 83.750 | 56.250 | 86.503 | 30.675 | 61.392 |
| bos.pep |  | 54.375 | 87.500 | 31.875 | 56.329 |
| mus.pep |  |  | 54.375 | 31.677 | 73.125 |
| sus.pep |  |  |  | 31.288 | 58.228 |
| gallus.pep |  |  |  |  | 30.818 |

Figure 12: Partial chromatogram of the fifth step of purification
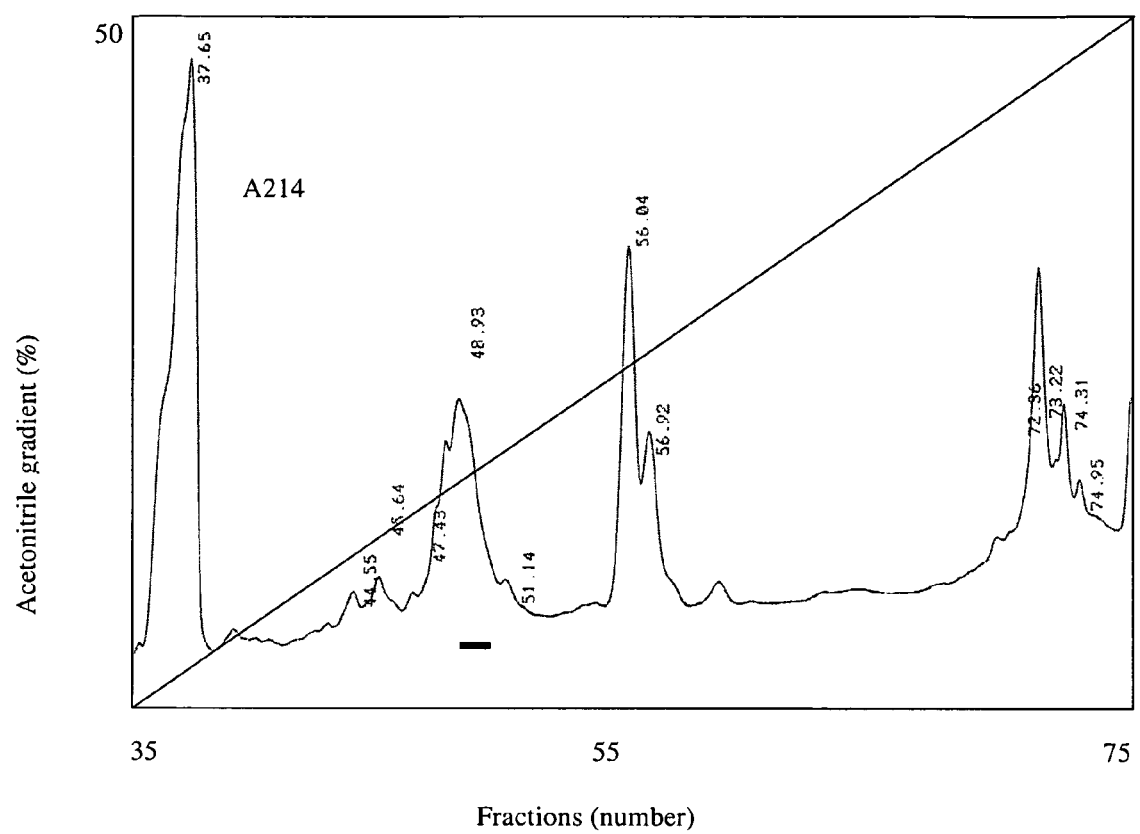

Figure 13: Primary screening of HPLC fractions obtained from the fractionation of human ovary ascites.
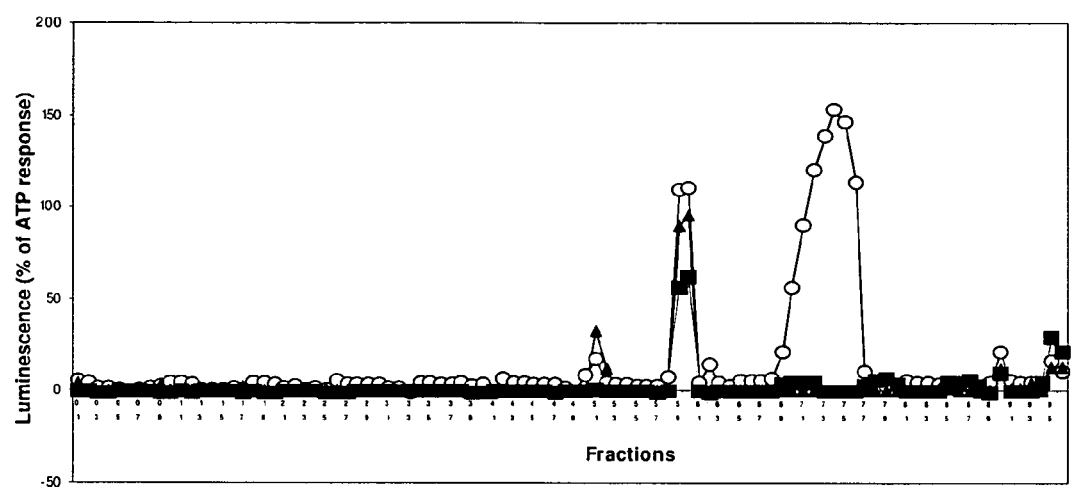

Figure 14: Activation of ChemerinR by cells transfected with Preprochemerin (TIG 2)
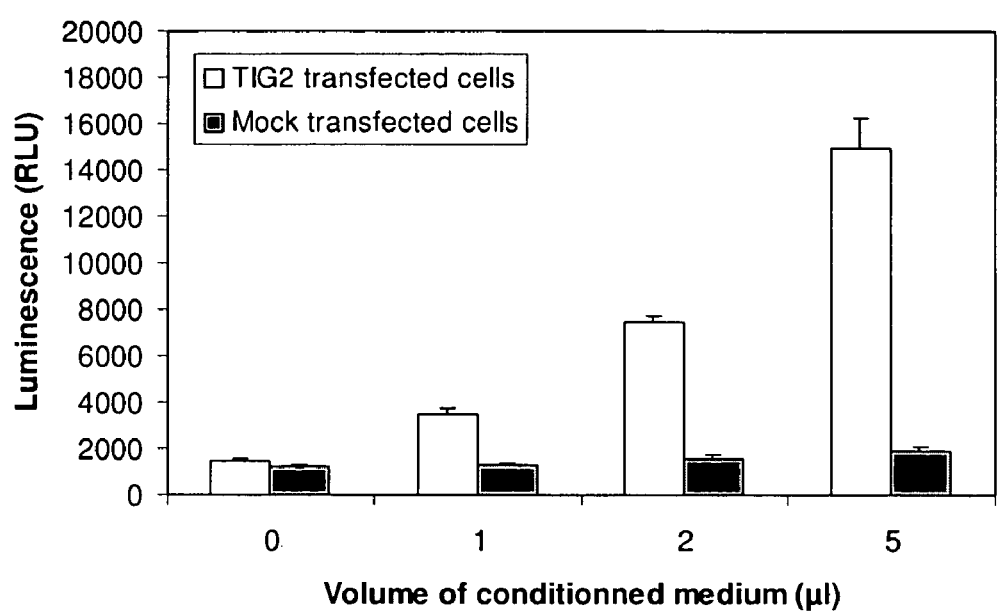

Figure 15: Characterization of antibodies directed against ChemerinR
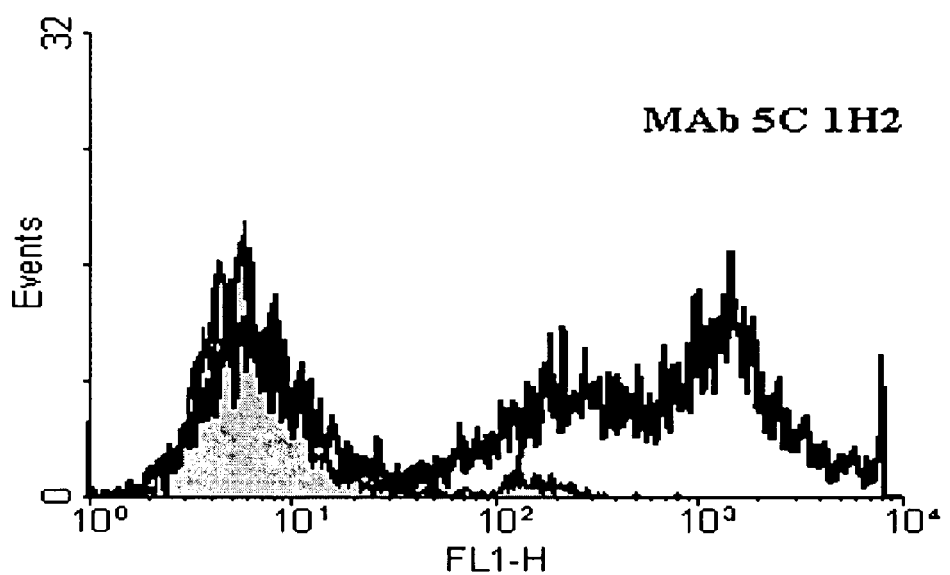

Figure 16.

Nucleotide (SEQ ID NO: 72) and deduced amino acid sequence (SEQ ID NO: 73) of a human truncated form of Proprechemerin

```
  1   M     R     R     L     L     I     P     L     A     W     L     G     A     V      15
  1  ATG   CGA   CGG   CTG   CTG   ATC   CCT   CTG   GCC   CTG   TGG   CTG   GGT   GCG   GTG    45

16   G     V     G     V     A     E     L     T     E     A     Q     R     R     G     L    30
 46  GGC   GTG   GGC   GTC   GCC   GAG   CTC   ACG   GAA   GCC   CAG   CGC   CGG   GGC   CTG    90

31   Q     V     A     L     E     E     F     H     K     H     P     P     V     Q     W    45
 91  CAG   GTG   GCC   CTG   GAG   GAA   TTT   CAC   AAG   CAC   CCG   CCC   GTG   CAG   TGG   135

46   A     F     Q     E     T     S     V     E     S     A     V     D     T     P     F    60
136  GCC   TTC   CAG   GAG   ACC   AGT   GTG   GAG   AGC   GCC   GTG   GAC   ACG   CCC   TTC   180

61   P     A     G     I     F     V     R     L     E     F     K     L     Q     Q     T    75
181  CCA   GCT   GGA   ATA   TTT   GTG   AGG   CTG   GAA   TTT   AAG   CTG   CAG   CAG   ACA   225

76   S     C     R     K     R     D     W     K     K     P     E     C     K     V     R    90
226  AGC   TGC   CGG   AAG   AGG   GAC   TGG   AAG   AAA   CCC   GAG   TGC   AAA   GTC   AGG   270

91   P     N     G     R     K     R     K     C     L     A     C     I     K     L     G   105
271  CCC   AAT   GGG   AGG   AAA   CGG   AAA   TGC   CTG   GCC   TGC   ATC   AAA   CTG   GGC   315

106   S     E     D     K     V     L     G     R     L     V     H     C     P     I     E   120
316  TCT   GAG   GAC   AAA   GTT   CTG   GGC   CGG   TTG   GTC   CAC   TGC   CCC   ATA   GAG   360

121   T     Q     V     L     R     E     A     E     E     H     Q     E     T     Q     C   135
361  ACC   CAA   GTT   CTG   CGG   GAG   GCT   GAG   GAG   CAC   CAG   GAG   ACC   CAG   TGC   405

136   L     R     V     Q     R     A     G     E     D     P     H     S     F     Y     F   150
406  CTC   AGG   GTG   CAG   CGG   GCT   GGT   GAG   GAC   CCC   CAC   AGC   TTC   TAC   TTC   450

151   P     G     Q     F     A     F     S                                                    157
451  CCT   GGA   CAG   TTC   GCC   TTC   TCC                                                   471
```

Figure 20a Human Chemerin peptides

| | |
|---|---|
| Human prochemerin-25 | QRAGEDPHSFYFPGQFAFSKALPRS (SEQ ID NO: 52) |
| Human prochemerin-6 | KALPRS (SEQ ID NO: 95) |
| Human Chemerin-19 | QRAGEDPHSFYFPGQFAFS (SEQ ID NO: 53) |
| Human [Lys-20]Chemerin-19 | QRAGEDPHSFYFPGQFAFSK (SEQ ID NO: 54) |
| Human [ΔSer19]Chemerin-19 | QRAGEDPHSFYFPGQFAF (SEQ ID NO: 55) |
| Human [ΔPhe18Ser19]Chemerin-19 | QRAGEDPHSFYFPGQFA (SEQ ID NO: 56) |
| Human Chemerin-17 | AGEDPHSFYFPGQFAFS (SEQ ID NO: 22) |
| Human Chemerin-15 | EDPHSFYFPGQFAFS (SEQ ID NO: 96) |
| Human Chemerin-13 | PHSFYFPGQFAFS (SEQ ID NO: 64) |
| Human Chemerin-12 | HSFYFPGQFAFS (SEQ ID NO: 63) |
| Human Chemerin-11 | SFYFPGQFAFS (SEQ ID NO: 97) |
| Human Chemerin-10 | FYFPGQFAFS (SEQ ID NO: 98) |
| Human Chemerin-9 | YFPGQFAFS (SEQ ID NO: 61) |
| Human Chemerin-8 | FPGQFAFS (SEQ ID NO: 60) |
| Human Chemerin-7 | PGQFAFS (SEQ ID NO: 99) |
| Human Chemerin-6 | GQFAFS (SEQ ID NO: 100) |
| Human Chemerin-5 | QFAFS (SEQ ID NO: 101) |
| Human [Ala-1]Chemerin-9 | AFPGQFAFS (SEQ ID NO: 65) |
| Human [Ala-2]Chemerin-9 | YAPGQFAFS (SEQ ID NO: 66) |
| Human [Ala-3]Chemerin-9 | YFAGQFAFS (SEQ ID NO: 67) |
| Human [Ala-4]Chemerin-9 | YFPAQFAFS (SEQ ID NO: 102) |
| Human [Ala-5]Chemerin-9 | YFPGAFAFS (SEQ ID NO: 68) |
| Human [Ala-6]Chemerin-9 | YFPGQAAFS (SEQ ID NO: 69) |
| Human [Ala-8]Chemerin-9 | YFPGQFAAS (SEQ ID NO: 70) |
| Human [Ala-9]Chemerin-9 | YFPGQFAFA (SEQ ID NO: 71) |

Figure 20b Mouse Chemerin polypeptides

| | |
|---|---|
| Mouse Chemerin-19 | AQAGEDPHGYFLPGQFAFS (SEQ ID NO: 43) |
| Mouse Chemerin-12 | HGYFLPGQFAFS (SEQ ID NO: 44) |
| Mouse Chemerin-11 | GYFLPGQFAFS (SEQ ID NO: 45) |
| Mouse Chemerin-10 | YFLPGQFAFS (SEQ ID NO: 46) |
| Mouse Chemerin-9 | FLPGQFAFS (SEQ ID NO: 47) |
| Mouse Chemerin-8 | LPGQFAFS (SEQ ID NO: 48) |
| Mouse prochemerin-26 | IAQAGEDPHGYFLPGQFAFSRALRTK (SEQ ID NO: 49) |
| Mouse [Arg-21]Chemerin-20 | IAQAGEDPHGYFLPGQFAFSR (SEQ ID NO: 50) |

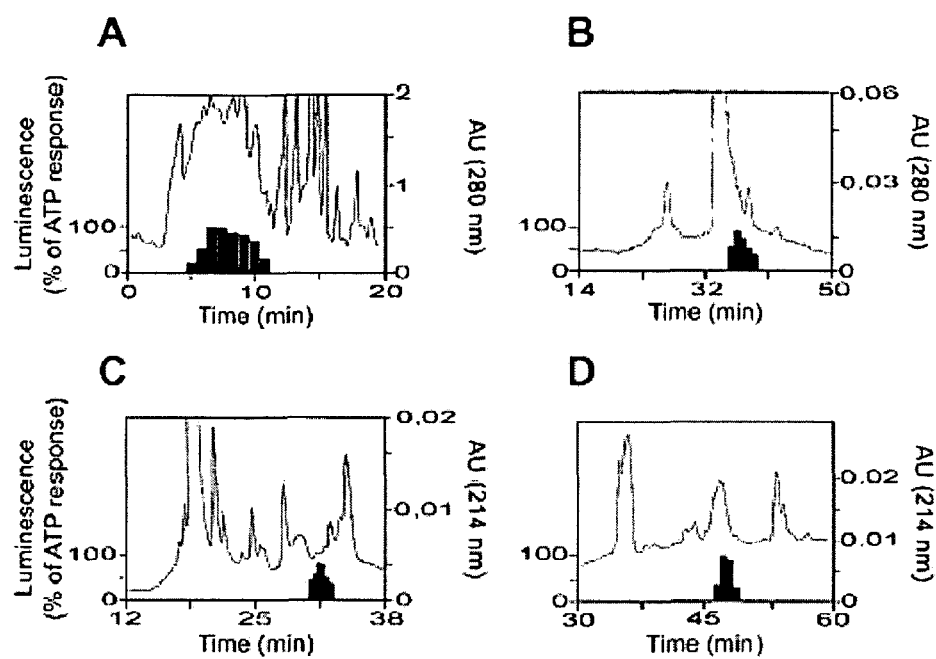
Figure 21. Purification of the natural ligand of the ChemR23 receptor from human inflammatory fluid.

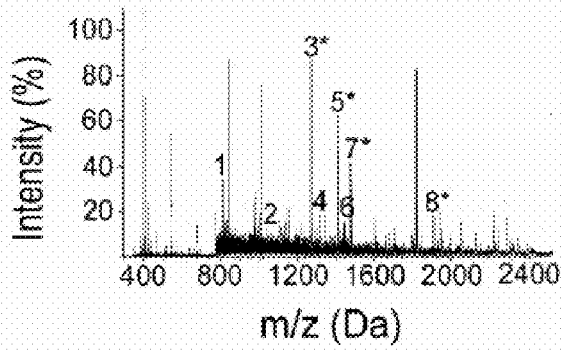

A

B

| # | a.a. | Sequence | M+H |
|---|------|----------|-----|
| 1 | 72-78 | (K) LQQTSCR (K) | 835.41 |
| 2 | 81-88 | (R) DWKKPECK (V) | 1033.51 |
| 3* | 29-39 | (R) GLQVALEEFHK (H) | 1270.68 |
| 4 | 98-109 | (K) CLACIKLGSEDK (V) | 1279.64 |
| 5* | 114-125 | (R) LVHCPIETQVLR (E) | 1407.78 |
| 6 | 28-39 | (R) RGLQVALEEFHK (H) | 1426.78 |
| 7* | 126-137 | (R) EAEEHQETQCLR (V) | 1472.64 |
| 8* | 141-157 | (R) AGEDPHSFYFPGQFAFS (K) | 1904.02 |

C

```
human          mrrlliplalwlgavgv-gv-a            22
mouse          mkcllislalwlgtvgtRGTE             24
FALL39  mktqrdghslgrw-slvlllglvmplaiiaQ         31 human     TTAG                       SYES       54
mouse     STTQ                       GYPR       56
FALL39  VLSYREAVLR TDGINQRSSDANLYRLLDLP         63
                                  *
human     VPT     I            CP PWK           86
mouse     EEV     A            C  DWKK          88
FALL39  RPTMLGDPD PKFVS TVKE VCPTTQQS           95
           *        * * *                *
human   -CRVR     C AC   GSED V         C      117
mouse   -CTI      C AC  MDPKG           C      119
FALL39  DCDF K D LVKP GTVT QARGSFDI SCDK       127
                                      *
human       TV R AEE    CLRVQR      SFY        149
mouse       LK  -GPQQDP  CIKIAQ     GYF        149
FALL39  DNKRfallgdffrkskekigkefkrivqrikd       159 human   F         kalprs                       163
mouse   L         ralrtk                       163
FALL39  flrnlvprtes                            170
```

Figure 22. Identification of Chemerin as the natural ligand of ChemR23, the Chemerin receptor.

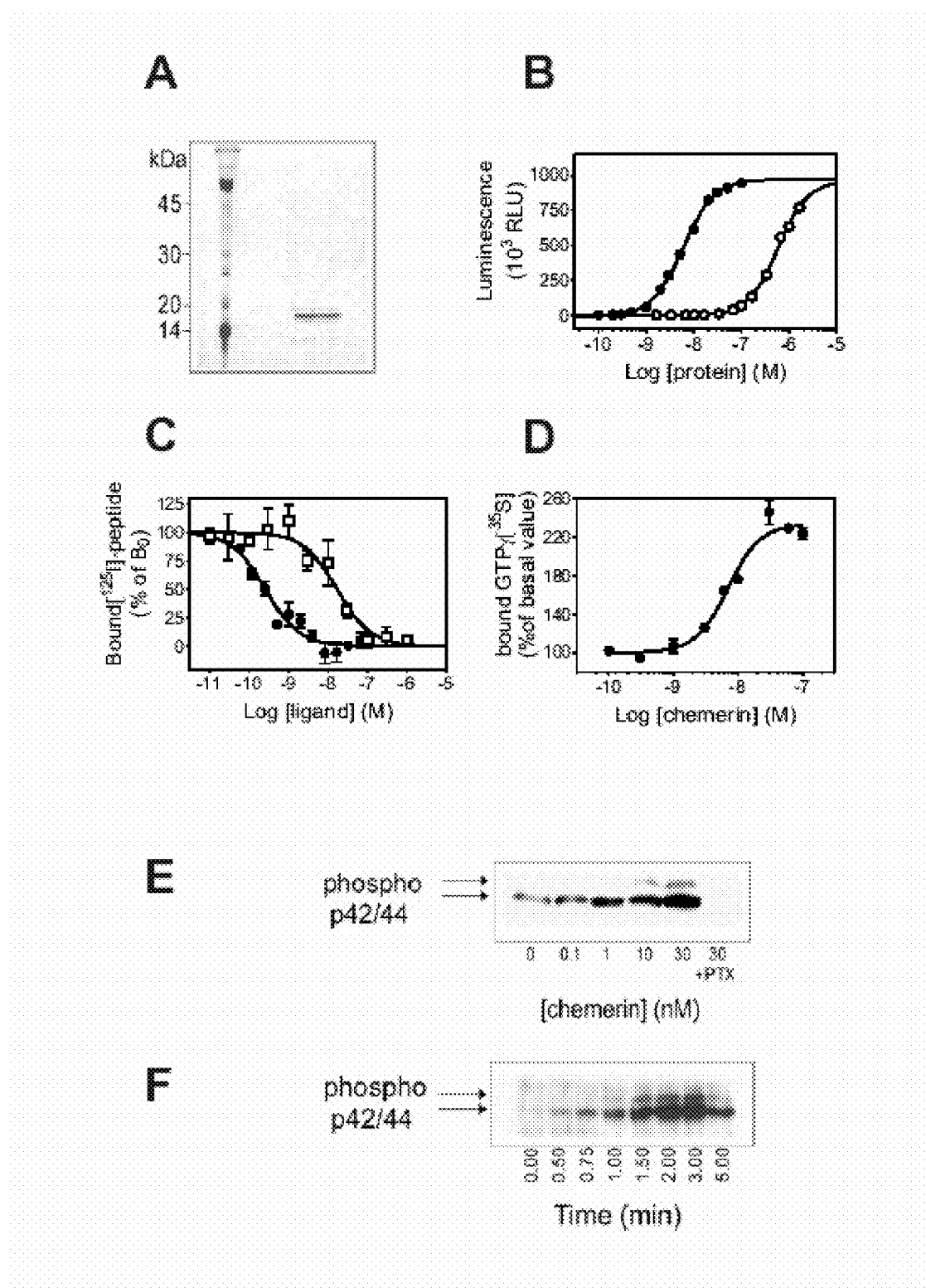
Figure 23. Pharmacology of the Chemerin receptor.

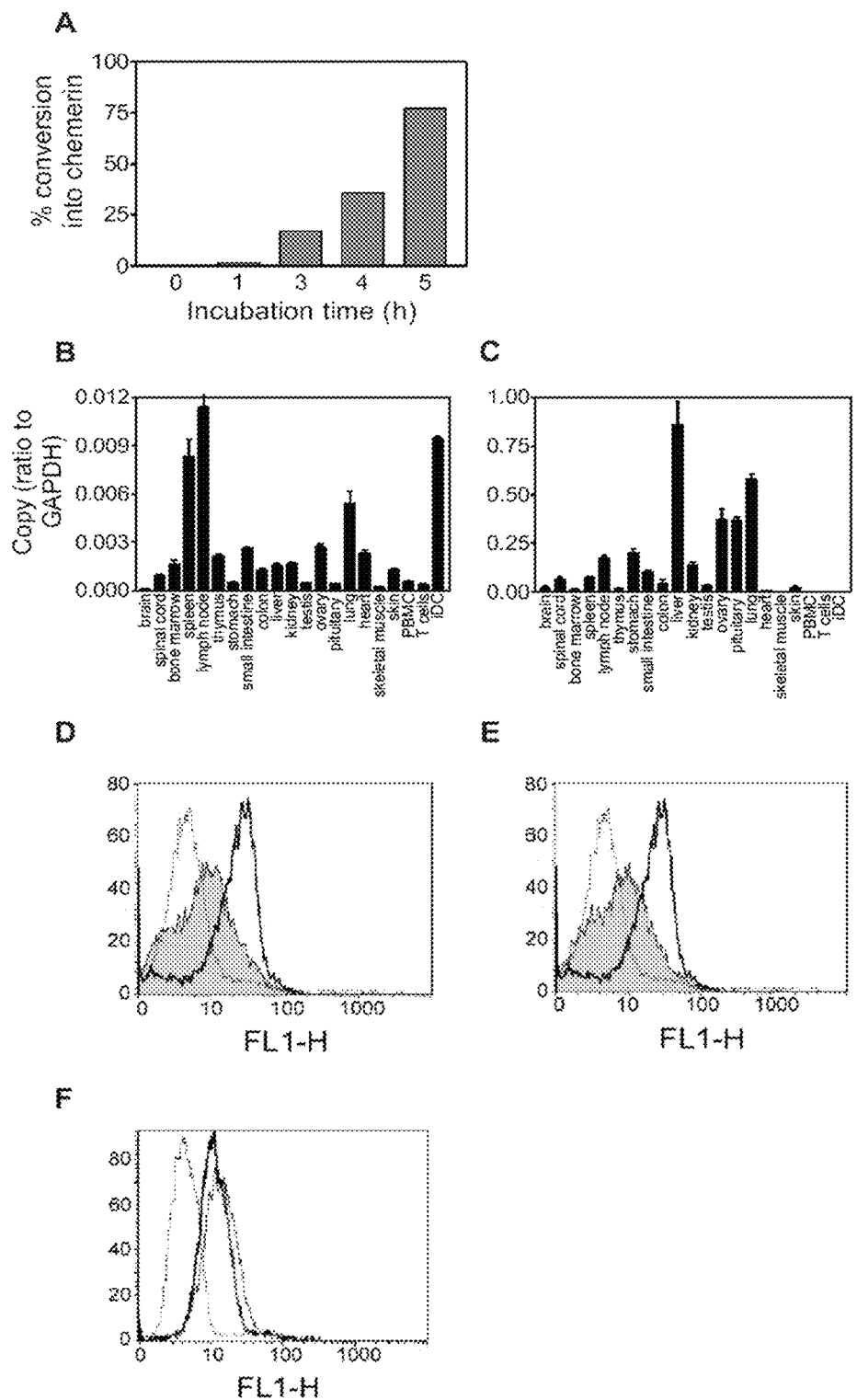
Figure 24. Expression of human Chemerin and its receptor.

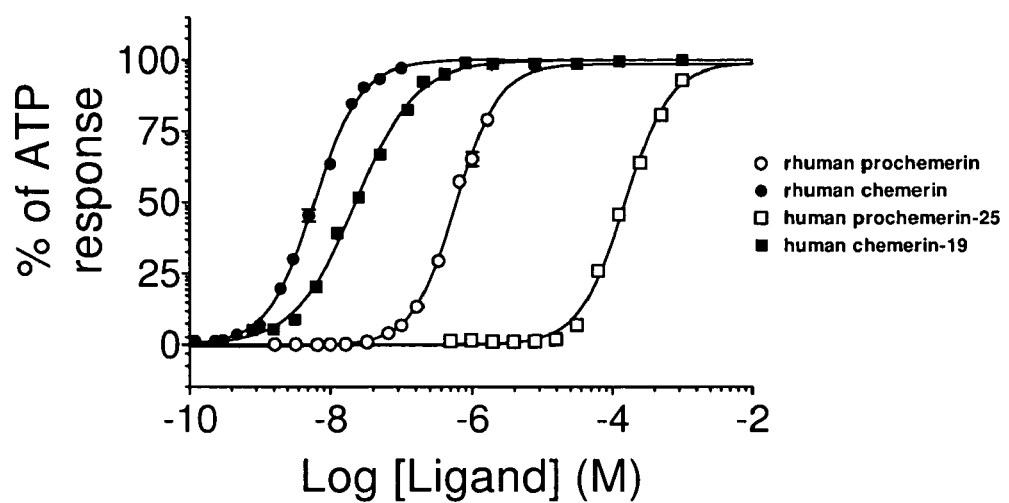
Figure 25A. Biological activity of Chemerin and C-terminal peptides on ChemR23.

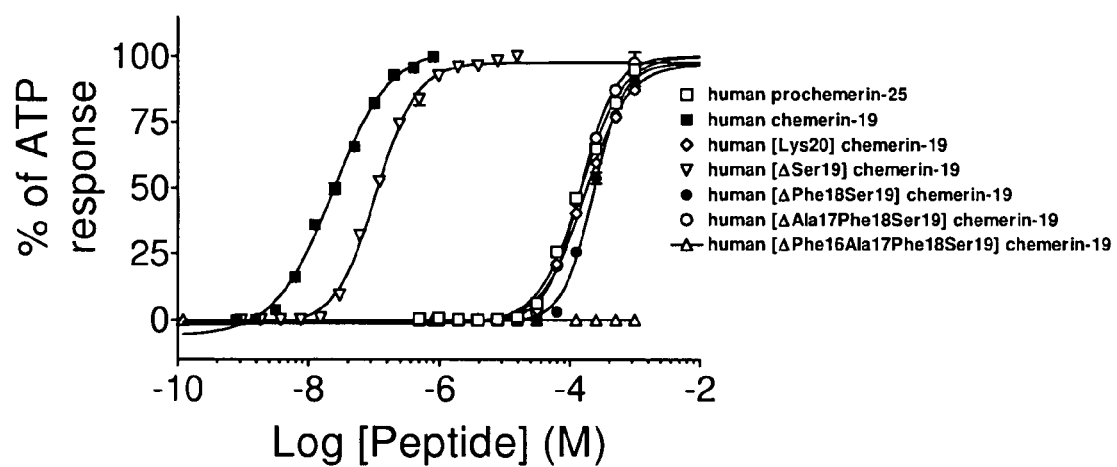
Figure 25B. Effect of C-terminal truncation on Chemerin biological activity.

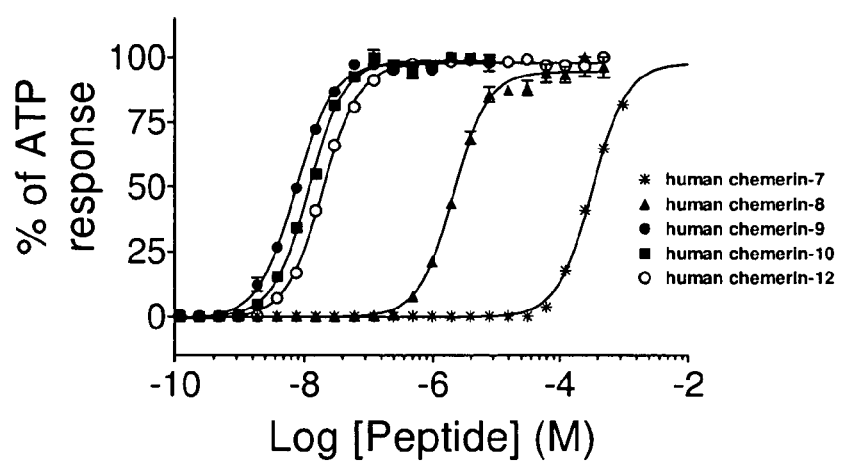
Figure 25C. Effect of N-terminal truncation on the biological activity of Chemerin-derived peptides.

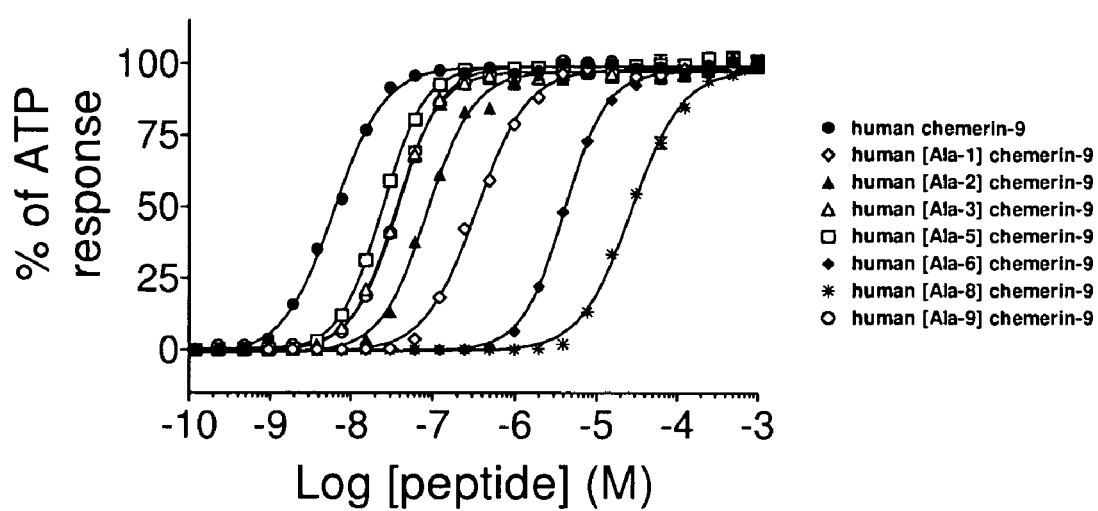
Figure 25D. Alanine scan of the Chemerin-9 peptide.

Figure 26. Biological activity of Chemerin on primary cells.
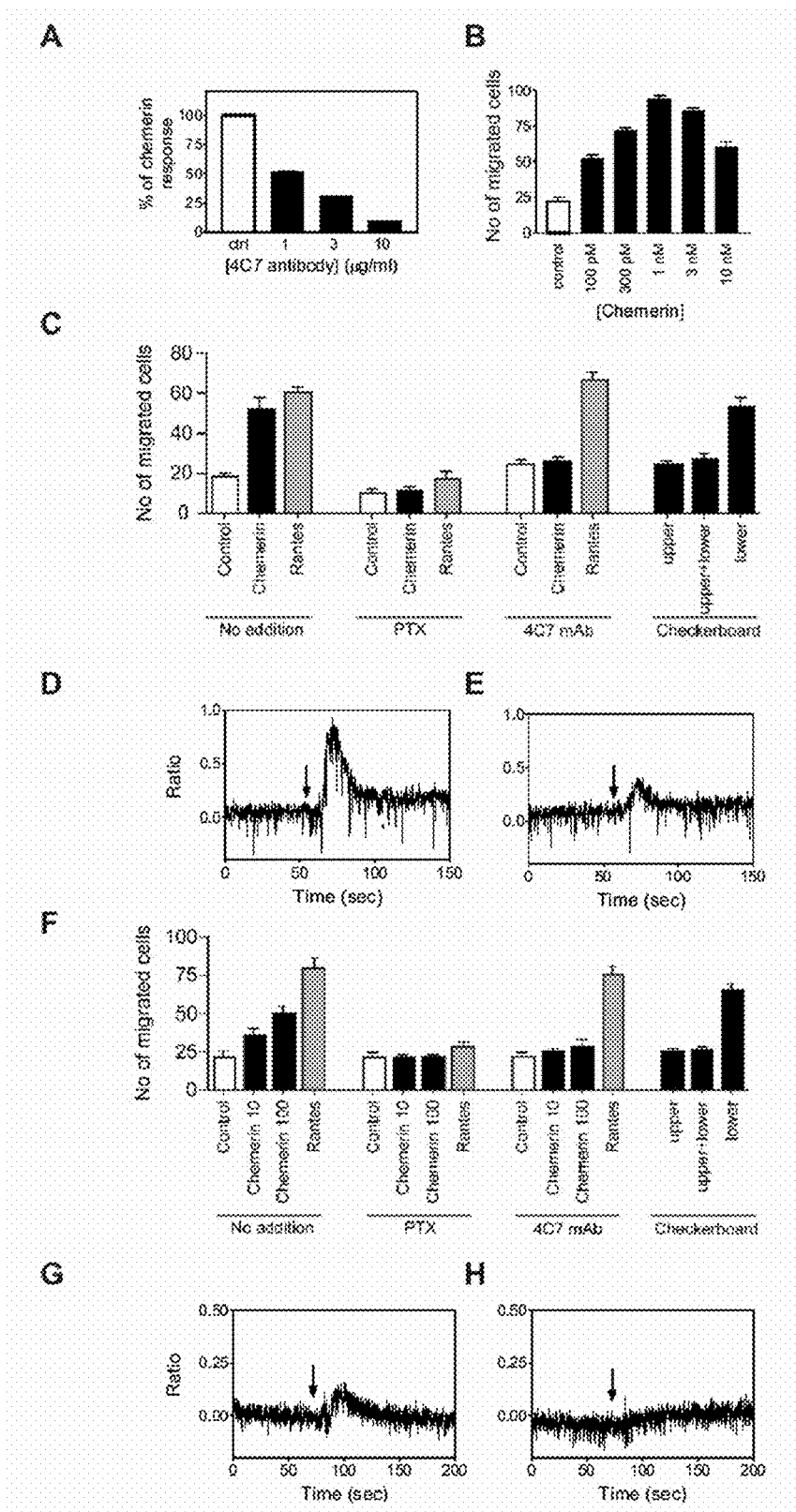

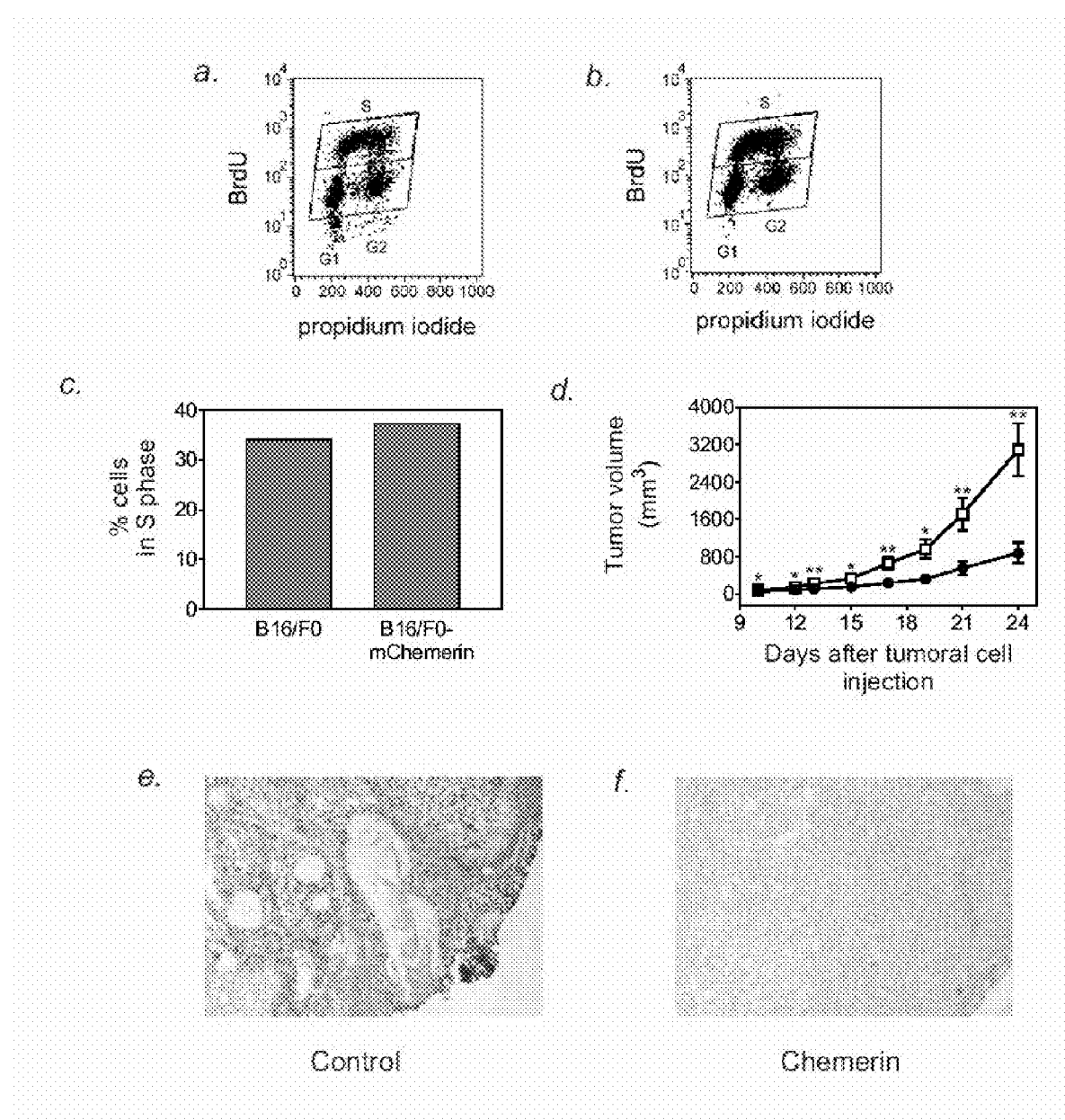
Figure 27. Anti-tumor activity of mouse Chemerin *in vivo*.

SEQUENCE LISTING

<160> NUMBER OF SEQ ID NOS: 102

<210> SEQ ID NO 1
<211> LENGTH: 1112
<212> TYPE: DNA
<213> ORGANISM: Homo sapiens

<400> SEQUENCE: 1

```
atggaggatg aagattacaa cacttccatc agttacggtg atgaataccc tgattattta      60
gactccattg tggttttgga ggacttatcc cccttggaag ccagggtgac caggatcttc     120
ctggtggtgg tctacagcat cgtctgcttc ctcgggattc tgggcaatgg tctggtgatc     180
atcattgcca ccttcaagat gaagaagaca gtgaacatgg tctggttcct caacctggca     240
gtggcagatt tcctgttcaa cgtcttcctc ccaatccata tcacctatgc cgccatggac     300
taccactggg ttttcgggac agccatgtgc aagatcagca acttccttct catccacaac     360
atgttcacca gcgtcttcct gctgaccatc atcagctctg accgctgcat ctctgtgctc     420
ctccctgtct ggtcccagaa ccaccgcagc gttcgcctgg cttacatggc ctgcatggtc     480
atctgggtcc tggctttctt cttgagttcc ccatctctcg tcttccggga cacagccaac     540
ctgcatggga aaatatcctg cttcaacaac ttcagcctgt ccacacctgg gtcttcctcg     600
tggcccactc actcccaaat ggaccctgtg gggtatagcc ggcacatggt ggtgactgtc     660
acccgcttcc tctgtggctt cctggtccca gtcctcatca tcacagcttg ctacctcacc     720
atcgtctgca aactgcagcg caaccgcctg gccaagacca gaagcccctt caagattatt     780
gtgaccatca tcattacctt cttcctctgc tggtgcccct accacacact caacctccta     840
gagctccacc acactgccat gcctggctct gtcttcagcc tgggtttgcc cctggccact     900
gcccttgcca ttgccaacag ctgcatgaac cccattctgt atgttttcat ggtcaggact     960
tcaagaagtt caaggtggcc ctcttctctc gcctggtcaa tgctctaagt gaagatacag    1020
gccactcttc ctaccccagc catagaagct ttaccaagat gtcaatgaat gagaggactt    1080
ctatgaatga gagggagacc ggcatgcttt ga                                  1112
```

<210> SEQ ID NO 2
<211> LENGTH: 371
<212> TYPE: PRT
<213> ORGANISM: Homo sapiens

<400> SEQUENCE: 2

```
Met Glu Asp Glu Asp Tyr Asn Thr Ser Ile Ser Tyr Gly Asp Glu Tyr
1               5                   10                  15

Pro Asp Tyr Leu Asp Ser Ile Val Val Leu Glu Asp Leu Ser Pro Leu
            20                  25                  30

Glu Ala Arg Val Thr Arg Ile Phe Leu Val Val Val Tyr Ser Ile Val
        35                  40                  45

Cys Phe Leu Gly Ile Leu Gly Asn Gly Leu Val Ile Ile Ile Ala Thr
    50                  55                  60

Phe Lys Met Lys Lys Thr Val Asn Met Val Trp Phe Leu Asn Leu Ala
65                  70                  75                  80

Val Ala Asp Phe Leu Phe Asn Val Phe Leu Pro Ile His Ile Thr Tyr
                85                  90                  95

Ala Ala Met Asp Tyr His Trp Val Phe Gly Thr Ala Met Cys Lys Ile
            100                 105                 110

Ser Asn Phe Leu Leu Ile His Asn Met Phe Thr Ser Val Phe Leu Leu
```

```
                    115                 120                 125
Thr Ile Ile Ser Ser Asp Arg Cys Ile Ser Val Leu Leu Pro Val Trp
130                 135                 140

Ser Gln Asn His Arg Ser Val Arg Leu Ala Tyr Met Ala Cys Met Val
145                 150                 155                 160

Ile Trp Val Leu Ala Phe Phe Leu Ser Ser Pro Ser Leu Val Phe Arg
                165                 170                 175

Asp Thr Ala Asn Leu His Gly Lys Ile Ser Cys Phe Asn Asn Phe Ser
                180                 185                 190

Leu Ser Thr Pro Gly Ser Ser Ser Trp Pro Thr His Ser Gln Met Asp
                195                 200                 205

Pro Val Gly Tyr Ser Arg His Met Val Val Thr Val Thr Arg Phe Leu
                210                 215                 220

Cys Gly Phe Leu Val Pro Val Leu Ile Ile Thr Ala Cys Tyr Leu Thr
225                 230                 235                 240

Ile Val Cys Lys Leu Gln Arg Asn Arg Leu Ala Lys Thr Lys Lys Pro
                245                 250                 255

Phe Lys Ile Ile Val Thr Ile Ile Thr Phe Phe Leu Cys Trp Cys
                260                 265                 270

Pro Tyr His Thr Leu Asn Leu Leu Glu Leu His His Thr Ala Met Pro
                275                 280                 285

Gly Ser Val Phe Ser Leu Gly Leu Pro Leu Ala Thr Ala Leu Ala Ile
                290                 295                 300

Ala Asn Ser Cys Met Asn Pro Ile Leu Tyr Val Phe Met Gly Gln Asp
305                 310                 315                 320

Phe Lys Lys Phe Lys Val Ala Leu Phe Ser Arg Leu Val Asn Ala Leu
                325                 330                 335

Ser Glu Asp Thr Gly His Ser Ser Tyr Pro Ser His Arg Ser Phe Thr
                340                 345                 350

Lys Met Ser Ser Met Asn Glu Arg Thr Ser Met Asn Glu Arg Glu Thr
                355                 360                 365

Gly Met Leu
      370

<210> SEQ ID NO 3
<211> LENGTH: 1116
<212> TYPE: DNA
<213> ORGANISM: Mus musculus

<400> SEQUENCE: 3
atggagtacg acgcttacaa cgactccggc atctatgatg atgagtactc tgatggcttt      60
ggctactttg tggacttgga ggaggcgagt ccgtgggagg ccaaggtggc cccggtcttc     120
ctggtggtga tctacagctt ggtgtgcttc tcggtctccc taggcaacgg cctggtgatt     180
gtcatcgcca ccttcaagat gaagaagacc gtgaacactg tgtggtttgt caacctggct     240
gtggccgact tcctgttcaa catcttttg ccgatgcaca tcacctacgc ggccatggac     300
taccactggg tgttcgggaa ggccatgtgc aagatcagca acttcttgct cagccacaac     360
atgtacacca gcgtcttcct gctgactgtc atcagctttg accgctgcat ctccgtgctg     420
ctccccgtct ggtcccagaa ccaccgcagc atcgcgctgg cctacatgac ctgctcggcc     480
gtctgggtcc tggctttctt cttgagctcc ccgtcccttg tcttccggga caccgccaac     540
attcatggga gataaccctg cttcaacaac ttcagcttgg ccgcgcctga gtcctcccca     600
catcccgccc actcgcaagt agtttccaca gggtacagca gacacgtggc ggtcactgtc     660
```

```
acccgcttcc tttgcggctt cctgatcccc gtcttcatca tcacggcctg ctaccttacc    720
atcgtcttca agctgcagcg caaccgcctg gccaagaaca agaagccctt caagatcatc    780
atcaccatca tcatcacctt cttcctctgc tggtgcccct accacaccct ctacctgctg    840
gagctccacc acacagctgt gccaagctct gtcttcagcc tggggctacc cctggccacg    900
gccgtcgcca tcgccaacag ctgcatgaac cccattctgt acgtcttcat gggccacgac    960
ttcagaaaat tcaaggtggc cctcttctcc cgcctggcca acgccctgag tgaggacaca   1020
ggcccctcct cctaccccag tcacaggagc ttcaccaaga tgtcgtcttt gaatgagaag   1080
gcttcggtga atgagaagga gaccagtacc ctctga                              1116

<210> SEQ ID NO 4
<211> LENGTH: 371
<212> TYPE: PRT
<213> ORGANISM: Mus musculus

<400> SEQUENCE: 4

Met Glu Tyr Asp Ala Tyr Asn Asp Ser Gly Ile Tyr Asp Asp Glu Tyr
1               5                   10                  15

Ser Asp Gly Phe Gly Tyr Phe Val Asp Leu Glu Glu Ala Ser Pro Trp
            20                  25                  30

Glu Ala Lys Val Ala Pro Val Phe Leu Val Ile Tyr Ser Leu Val
        35                  40                  45

Cys Phe Leu Gly Leu Leu Gly Asn Gly Leu Val Ile Val Ile Ala Thr
    50                  55                  60

Phe Lys Met Lys Lys Thr Val Asn Thr Val Trp Phe Val Asn Leu Ala
65                  70                  75                  80

Val Ala Asp Phe Leu Phe Asn Ile Phe Leu Pro Met His Ile Thr Tyr
                85                  90                  95

Ala Ala Met Asp Tyr His Trp Val Phe Gly Lys Ala Met Cys Lys Ile
            100                 105                 110

Ser Asn Phe Leu Leu Ser His Asn Met Tyr Thr Ser Val Phe Leu Leu
        115                 120                 125

Thr Val Ile Ser Phe Asp Arg Cys Ile Ser Val Leu Leu Pro Val Trp
    130                 135                 140

Ser Gln Asn His Arg Ser Ile Arg Leu Ala Tyr Met Thr Cys Ser Ala
145                 150                 155                 160

Val Trp Val Leu Ala Phe Phe Leu Ser Ser Pro Ser Leu Val Phe Arg
                165                 170                 175

Asp Thr Ala Asn Ile His Gly Lys Ile Thr Cys Phe Asn Asn Phe Ser
            180                 185                 190

Leu Ala Ala Pro Glu Ser Ser Pro His Pro Ala His Ser Gln Val Val
        195                 200                 205

Ser Thr Gly Tyr Ser Arg His Val Ala Val Thr Val Thr Arg Phe Leu
    210                 215                 220

Cys Gly Phe Leu Ile Pro Val Phe Ile Ile Thr Ala Cys Tyr Leu Thr
225                 230                 235                 240

Ile Val Phe Lys Leu Gln Arg Asn Arg Leu Ala Lys Asn Lys Lys Pro
                245                 250                 255

Phe Lys Ile Ile Ile Thr Ile Ile Ile Thr Phe Phe Leu Cys Trp Cys
            260                 265                 270

Pro Tyr His Thr Leu Tyr Leu Leu Glu Leu His His Thr Ala Val Pro
        275                 280                 285

Ser Ser Val Phe Ser Leu Gly Leu Pro Leu Ala Thr Ala Val Ala Ile
    290                 295                 300
```

```
Ala Asn Ser Cys Met Asn Pro Ile Leu Tyr Val Phe Met Gly His Asp
305                 310                 315                 320

Phe Arg Lys Phe Lys Val Ala Leu Phe Ser Arg Leu Ala Asn Ala Leu
            325                 330                 335

Ser Glu Asp Thr Gly Pro Ser Ser Tyr Pro Ser His Arg Ser Phe Thr
        340                 345                 350

Lys Met Ser Ser Leu Asn Glu Lys Ala Ser Val Asn Glu Lys Glu Thr
        355                 360                 365

Ser Thr Leu
    370

<210> SEQ ID NO 5
<211> LENGTH: 1116
<212> TYPE: DNA
<213> ORGANISM: Rattus norvegicus

<400> SEQUENCE: 5
atggagtacg agggttacaa cgactccagc atctacggtg aggagtattc tgacggctcg      60
gactacatcg tggacttgga ggaggcgggt ccactggagg ccaaggtggc cgaggtcttc     120
ctggtggtaa tctacagctt ggtgtgcttc ctcgggatcc taggcaatgg cctggtgatt     180
gtcatcgcca ccttcaagat gaagaagacg gtgaacaccg tgtggtttgt caacctggcc     240
gtggctgact tcctgttcaa catcttcttg cccatccaca tcacctatgc cgctatggac     300
taccactggg tgttcgggaa agccatgtgc aagattagta gctttctgct aagccacaac     360
atgtacacca gcgtcttcct gctcactgtc atcagcttcg accgctgcat ctccgtgctc     420
ctccccgtct ggtcccagaa ccaccgcagc gtgcgtctgg cctacatgac ctgcgtggtt     480
gtctgggtct ggcttccttc tgagtctccc ccgtccctcg tcttcggaca cgtcagcacc     540
agccacggga agataacctg cttcaacaac ttcagcctgg cggcgcccga gcctttctct     600
cattccaccc accgcgaac agacccggta gggtacagca acatgtggc ggtcaccgtc     660 acccgcttcc tctgtggctt cctgatcccc gtcttcatca tcacggcctg ttacctcacc     720
atcgtcttca gttgcagcg caaccgccag gccaagacca gaagcccctt caagatcatc     780
atcaccatca tcatcacctt cttcctctgc tggtgccccc accacacact ctacctgctg     840
gagctccacc acacggctgt gccagcctct gtcttcagcc tgggactgcc cctggcaca     900 gccgtcgcca tcgccaacag ctgtatgaac cccatcctgt acgtcttcat gggccacgac    960
ttcaaaaaat tcaaggtggc ccttttctcc cgcctggtga atgccctgag cgaggacaca   1020
ggaccctcct cctaccccag tcacaggagc ttcaccaaga tgtcctcatt gattgagaag   1080
gcttcagtga atgagaaaga gaccagcacc ctctga                            1116

<210> SEQ ID NO 6
<211> LENGTH: 371
<212> TYPE: PRT
<213> ORGANISM: Rattus norvegicus

<400> SEQUENCE: 6

Met Glu Tyr Glu Gly Tyr Asn Asp Ser Ser Ile Tyr Gly Glu Glu Tyr
1               5                   10                  15

Ser Asp Gly Ser Asp Tyr Ile Val Asp Leu Glu Glu Ala Gly Pro Leu
            20                  25                  30

Glu Ala Lys Val Ala Glu Val Phe Leu Val Val Ile Tyr Ser Leu Val
        35                  40                  45

Cys Phe Leu Gly Ile Leu Gly Asn Gly Leu Val Ile Val Ile Ala Thr
```

Phe Lys Met Lys Lys Thr Val Asn Thr Val Trp Phe Val Asn Leu Ala
65                  70                  75                  80

Val Ala Asp Phe Leu Phe Asn Ile Phe Leu Pro Ile His Ile Thr Tyr
                85                  90                  95

Ala Ala Met Asp Tyr His Trp Val Phe Gly Lys Ala Met Cys Lys Ile
            100                 105                 110

Ser Ser Phe Leu Leu Ser His Asn Met Tyr Thr Ser Val Phe Leu Leu
        115                 120                 125

Thr Val Ile Ser Phe Asp Arg Cys Ile Ser Val Leu Leu Pro Val Trp
    130                 135                 140

Ser Gln Asn His Arg Ser Val Arg Leu Ala Tyr Met Thr Cys Val Val
145                 150                 155                 160

Val Trp Val Trp Leu Ser Ser Glu Ser Pro Pro Ser Leu Val Phe Gly
                165                 170                 175

His Val Ser Thr Ser His Gly Lys Ile Thr Cys Phe Asn Asn Phe Ser
            180                 185                 190

Leu Ala Ala Pro Glu Pro Phe Ser His Ser Thr His Pro Arg Thr Asp
        195                 200                 205

Pro Val Gly Tyr Ser Arg His Val Ala Val Thr Val Thr Arg Phe Leu
    210                 215                 220

Cys Gly Phe Leu Ile Pro Val Phe Ile Ile Thr Ala Cys Tyr Leu Thr
225                 230                 235                 240

Ile Val Phe Lys Leu Gln Arg Asn Arg Gln Ala Lys Thr Lys Lys Pro
                245                 250                 255

Phe Lys Ile Ile Ile Thr Ile Ile Ile Thr Phe Phe Leu Cys Trp Cys
            260                 265                 270

Pro Tyr His Thr Leu Tyr Leu Leu Glu Leu His His Thr Ala Val Pro
        275                 280                 285

Ala Ser Val Phe Ser Leu Gly Leu Pro Leu Ala Thr Ala Val Ala Ile
    290                 295                 300

Ala Asn Ser Cys Met Asn Pro Ile Leu Tyr Val Phe Met Gly His Asp
305                 310                 315                 320

Phe Lys Lys Phe Lys Val Ala Leu Phe Ser Arg Leu Val Asn Ala Leu
                325                 330                 335

Ser Glu Asp Thr Gly Pro Ser Ser Tyr Pro Ser His Arg Ser Phe Thr
            340                 345                 350

Lys Met Ser Ser Leu Ile Glu Lys Ala Ser Val Asn Glu Lys Glu Thr
        355                 360                 365

Ser Thr Leu
    370

<210> SEQ ID NO 7
<211> LENGTH: 492
<212> TYPE: DNA
<213> ORGANISM: Homo sapiens

<400> SEQUENCE: 7
atgcgacggc tgctgatccc tctggccctg tggctgggtg cggtgggcgt gggcgtcgcc      60
gagctcacgg aagcccagcg ccggggcctg caggtggccc tggaggaatt tcacaagcac     120
ccgcccgtgc agtgggcctt ccaggagacc agtgtggaga gcgccgtgga cacgcccttc     180
ccagctggaa tatttgtgag ctggaatttt aagctgcagc agacaagctg ccggaagagg     240
gactggaaga aacccgagtg caaagtcagg cccaatggga ggaaacggaa atgcctggcc     300

```
tgcatcaaac tgggctctga ggacaaagtt ctgggccggt tggtccactg ccccatagag    360
acccaagttc tgcgggaggc tgaggagcac caggagaccc agtgcctcag ggtgcagcgg    420
gctggtgagg accccacag cttctacttc cctggacagt tcgccttctc caaggccctg     480
ccccgcagct aa                                                        492
```

<210> SEQ ID NO 8
<211> LENGTH: 163
<212> TYPE: PRT
<213> ORGANISM: Homo sapiens

<400> SEQUENCE: 8

```
Met Arg Arg Leu Leu Ile Pro Leu Ala Leu Trp Leu Gly Ala Val Gly
1               5                   10                  15

Val Gly Val Ala Glu Leu Thr Glu Ala Gln Arg Gly Leu Gln Val
            20                  25                  30

Ala Leu Glu Glu Phe His Lys His Pro Pro Val Gln Trp Ala Phe Gln
        35                  40                  45

Glu Thr Ser Val Glu Ser Ala Val Asp Thr Pro Phe Pro Ala Gly Ile
    50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Glu Ala Glu
        115                 120                 125

Glu His Gln Glu Thr Gln Cys Leu Arg Val Gln Arg Ala Gly Glu Asp
    130                 135                 140

Pro His Ser Phe Tyr Phe Pro Gly Gln Phe Ala Phe Ser Lys Ala Leu
145                 150                 155                 160

Pro Arg Ser
```

<210> SEQ ID NO 9
<211> LENGTH: 489
<212> TYPE: DNA
<213> ORGANISM: Mus musculus

<400> SEQUENCE: 9

```
atgaagtgct tgctgatctc cctagcccta tggctgggca cagtgggcac acgtgggaca    60
gagcccgaac tcagcgagac ccagcgcagg agcctacagg tggctctgga ggagttccac   120
aaacacccac ctgtgcagtt ggccttccaa gagatcggtg tggacagagc tgaagaagtg   180
ctcttctcag ctggcacctt tgtgaggttg gaatttaagc tccagcagac caactgcccc   240
aagaaggact ggaaaaagcc ggagtgcaca atcaaaccaa cgggagaag gcggaaatgc    300 ctggcctgca ttaaaatgga ccccaagggt aaaattctag gccggatagt ccactgccca   360
attctgaagc aagggcctca ggatcctcag gagttgcaat gcattaagat agcacaggct   420
ggcgaagacc cccacggcta cttcctacct ggacagtttg ccttctccag ggccctgaga   480
accaaataa                                                            489
```

<210> SEQ ID NO 10
<211> LENGTH: 162
<212> TYPE: PRT
<213> ORGANISM: Mus musculus

```
<400> SEQUENCE: 10

Met Lys Cys Leu Leu Ile Ser Leu Ala Leu Trp Leu Gly Thr Val Gly
1               5                   10                  15

Thr Arg Gly Thr Glu Pro Glu Leu Ser Glu Thr Gln Arg Arg Ser Leu
            20                  25                  30

Gln Val Ala Leu Glu Glu Phe His Lys His Pro Val Gln Leu Ala
        35                  40                  45

Phe Gln Glu Ile Gly Val Asp Arg Ala Glu Glu Val Leu Phe Ser Ala
    50                  55                  60

Gly Thr Phe Val Arg Leu Glu Phe Lys Leu Gln Gln Thr Asn Cys Pro
65              70                  75                  80

Lys Lys Asp Trp Lys Lys Pro Glu Cys Thr Ile Lys Pro Asn Gly Arg
                85                  90                  95

Arg Arg Lys Cys Leu Ala Cys Ile Lys Met Asp Pro Lys Gly Lys Ile
            100                 105                 110

Leu Gly Arg Ile Val His Cys Pro Ile Leu Lys Gln Gly Pro Gln Asp
            115                 120                 125

Pro Gln Glu Leu Gln Cys Ile Lys Ile Ala Gln Ala Gly Glu Asp Pro
        130                 135                 140

His Gly Tyr Phe Leu Pro Gly Gln Phe Ala Phe Ser Arg Ala Leu Arg
145                 150                 155                 160

Thr Lys

<210> SEQ ID NO 11
<211> LENGTH: 429
<212> TYPE: DNA
<213> ORGANISM: Homo sapiens

<400> SEQUENCE: 11
gagctcacgg aagcccagcg ccggggcctg caggtggccc tggaggaatt tcacaagcac     60
ccgcccgtgc agtgggcctt ccaggagacc agtgtggaga gcgccgtgga cacgcccttc    120
ccagctggaa tatttgtgag gctggaattt aagctgcagc agacaagctg ccggaagagg    180
gactggaaga aacccgagtg caaagtcagg cccaatggga ggaaacggaa atgcctggcc    240
tgcatcaaac tgggctctga ggacaaagtt ctgggccggt tggtccactg ccccatagag    300
acccaagttc tgcgggaggc tgaggagcac caggagaccc agtgcctcag ggtgcagcgg    360
gctggtgagg accccacag cttctacttc cctggacagt tcgccttctc caaggccctg    420
ccccgcagc                                                             429

<210> SEQ ID NO 12
<211> LENGTH: 143
<212> TYPE: PRT
<213> ORGANISM: Homo sapiens

<400> SEQUENCE: 12

Glu Leu Thr Glu Ala Gln Arg Arg Gly Leu Gln Val Ala Leu Glu Glu
1               5                   10                  15

Phe His Lys His Pro Val Gln Trp Ala Phe Gln Glu Thr Ser Val
            20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
        50                  55                  60

Pro Glu Cys Lys Val Arg Pro Asn Gly Arg Lys Arg Lys Cys Leu Ala
65              70                  75                  80
```

Cys Ile Lys Leu Gly Ser Glu Asp Lys Val Leu Gly Arg Leu Val His
            85                  90                  95

Cys Pro Ile Glu Thr Gln Val Leu Arg Glu Ala Glu His Gln Glu
            100                 105                 110

Thr Gln Cys Leu Arg Val Gln Arg Ala Gly Glu Asp Pro His Ser Phe
            115                 120                 125

Tyr Phe Pro Gly Gln Phe Ala Phe Ser Lys Ala Leu Pro Arg Ser
            130                 135                 140

<210> SEQ ID NO 13
<211> LENGTH: 411
<212> TYPE: DNA
<213> ORGANISM: Homo sapiens

<400> SEQUENCE: 13
gagctcacgg aagcccagcg ccggggcctg caggtggccc tggaggaatt tcacaagcac      60
ccgcccgtgc agtgggcctt ccaggagacc agtgtggaga gcgccgtgga cacgcccttc     120
ccagctggaa tatttgtgag gctggaattt aagctgcagc agacaagctg ccggaagagg     180
gactggaaga aacccgagtg caaagtcagg cccaatggga ggaaacggaa atgcctggcc     240
tgcatcaaac tgggctctga ggacaaagtt ctgggccggt tggtccactg ccccatagag     300
acccaagttc tgcgggaggc tgaggagcac aggagaccc agtgcctcag ggtgcagcgg     360
gctggtgagg accccacag cttctacttc cctggacagt tcgccttctc c              411

<210> SEQ ID NO 14
<211> LENGTH: 137
<212> TYPE: PRT
<213> ORGANISM: Homo sapiens

<400> SEQUENCE: 14

Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
            20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
    50                  55                  60

Pro Glu Cys Lys Val Arg Pro Asn Gly Arg Lys Arg Lys Cys Leu Ala
65                  70                  75                  80

Cys Ile Lys Leu Gly Ser Glu Asp Lys Val Leu Gly Arg Leu Val His
            85                  90                  95

Cys Pro Ile Glu Thr Gln Val Leu Arg Glu Ala Glu Glu His Gln Glu
            100                 105                 110

Thr Gln Cys Leu Arg Val Gln Arg Ala Gly Glu Asp Pro His Ser Phe
            115                 120                 125

Tyr Phe Pro Gly Gln Phe Ala Phe Ser
            130                 135

<210> SEQ ID NO 15
<211> LENGTH: 9
<212> TYPE: PRT
<213> ORGANISM: Homo sapiens

<400> SEQUENCE: 15

Lys Leu Gln Gln Thr Ser Cys Arg Lys
1               5

```
<210> SEQ ID NO 16
<211> LENGTH: 10
<212> TYPE: PRT
<213> ORGANISM: Homo sapiens

<400> SEQUENCE: 16

Arg Asp Trp Lys Lys Pro Glu Cys Lys Val
1               5                   10

<210> SEQ ID NO 17
<211> LENGTH: 13
<212> TYPE: PRT
<213> ORGANISM: Homo sapiens

<400> SEQUENCE: 17

Arg Gly Leu Gln Val Ala Leu Glu Glu Phe His Lys His
1               5                   10

<210> SEQ ID NO 18
<211> LENGTH: 14
<212> TYPE: PRT
<213> ORGANISM: Homo sapiens

<400> SEQUENCE: 18

Lys Cys Leu Ala Cys Ile Lys Leu Gly Ser Glu Asp Lys Val
1               5                   10

<210> SEQ ID NO 19
<211> LENGTH: 14
<212> TYPE: PRT
<213> ORGANISM: Homo sapiens

<400> SEQUENCE: 19

Arg Leu Val His Cys Pro Ile Glu Thr Gln Leu Val Arg Glu
1               5                   10

<210> SEQ ID NO 20
<211> LENGTH: 14
<212> TYPE: PRT
<213> ORGANISM: Homo sapiens

<400> SEQUENCE: 20

Arg Arg Gly Leu Gln Val Ala Leu Glu Glu Phe His Lys His
1               5                   10

<210> SEQ ID NO 21
<211> LENGTH: 14
<212> TYPE: PRT
<213> ORGANISM: Homo sapiens

<400> SEQUENCE: 21

Arg Glu Ala Glu Glu His Gln Glu Thr Gln Cys Leu Arg Val
1               5                   10

<210> SEQ ID NO 22
<211> LENGTH: 19
<212> TYPE: PRT
<213> ORGANISM: Homo sapiens

<400> SEQUENCE: 22

Arg Ala Gly Glu Asp Pro His Ser Phe Tyr Phe Pro Gly Gln Phe Ala
1               5                   10                  15

Phe Ser Lys
```

```
<210> SEQ ID NO 23
<211> LENGTH: 28
<212> TYPE: DNA
<213> ORGANISM: Homo sapiens

<400> SEQUENCE: 23
caggaattca gcatgcgacg gctgctga                                          28

<210> SEQ ID NO 24
<211> LENGTH: 29
<212> TYPE: DNA
<213> ORGANISM: Homo sapiens

<400> SEQUENCE: 24
gctctagatt agctgcgggg cagggcctt                                         29

<210> SEQ ID NO 25
<211> LENGTH: 48
<212> TYPE: DNA
<213> ORGANISM: Mus musculus

<400> SEQUENCE: 25
tctctcgaga aaagagaggc tgaagctaca cgtgggacag agcccgaa                    48

<210> SEQ ID NO 26
<211> LENGTH: 48
<212> TYPE: DNA
<213> ORGANISM: Homo sapiens

<400> SEQUENCE: 26
tctctcgaga aaagagaggc tgaagctggc gtcgccgagc tcacggaa                    48

<210> SEQ ID NO 27
<211> LENGTH: 48
<212> TYPE: DNA
<213> ORGANISM: Homo sapiens

<400> SEQUENCE: 27
tctctcgaga aaagagaggc tgaagctgtg ggcgtcgccg agctcacg                    48

<210> SEQ ID NO 28
<211> LENGTH: 30
<212> TYPE: DNA
<213> ORGANISM: Mus musculus

<400> SEQUENCE: 28
agggaattct tatttggttc tcagggccct                                        30

<210> SEQ ID NO 29
<211> LENGTH: 30
<212> TYPE: DNA
<213> ORGANISM: Homo sapiens

<400> SEQUENCE: 29
agggaattct tagctgcggg gcagggcctt                                        30

<210> SEQ ID NO 30
<211> LENGTH: 28
<212> TYPE: DNA
<213> ORGANISM: Mus musculus

<400> SEQUENCE: 30
caggaattcg ccatgaagtg cttgctga                                          28
```

```
<210> SEQ ID NO 31
<211> LENGTH: 28
<212> TYPE: DNA
<213> ORGANISM: Homo sapiens

<400> SEQUENCE: 31
caggaattca gcatgcgacg gctgctga                                              28

<210> SEQ ID NO 32
<211> LENGTH: 29
<212> TYPE: DNA
<213> ORGANISM: Mus musculus

<400> SEQUENCE: 32
gctctagatt tggttctcag ggccctgga                                             29

<210> SEQ ID NO 33
<211> LENGTH: 29
<212> TYPE: DNA
<213> ORGANISM: Homo sapiens

<400> SEQUENCE: 33
gctctagagc tgcggggcag ggccttgga                                             29

<210> SEQ ID NO 34
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(17)
<223> OTHER INFORMATION: Synthetic primer

<400> SEQUENCE: 34
gcagacaagc tgccgga                                                          17

<210> SEQ ID NO 35
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(19)
<223> OTHER INFORMATION: Synthetic primer

<400> SEQUENCE: 35
agtttgatgc aggccaggc                                                        19

<210> SEQ ID NO 36
<211> LENGTH: 23
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(23)
<223> OTHER INFORMATION: Synthetic probe

<400> SEQUENCE: 36
aacccgagtg caaagtcagg ccc                                                   23

<210> SEQ ID NO 37
```

```
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(18)
<223> OTHER INFORMATION: Synthetic primer

<400> SEQUENCE: 37
gtcccagaac caccgcag                                                 18

<210> SEQ ID NO 38
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: Synthetic primer

<400> SEQUENCE: 38
aagaaagcca ggacccagat g                                             21

<210> SEQ ID NO 39
<211> LENGTH: 23
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<222> LOCATION: (1)..(23)
<223> OTHER INFORMATION: Synthetic probe

<400> SEQUENCE: 39
ttcgcctggc ttacatggcc tgc                                           23

<210> SEQ ID NO 40
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(19)
<223> OTHER INFORMATION: Synthetic primer

<400> SEQUENCE: 40
gaaggtgaag gtcggagtc                                                19

<210> SEQ ID NO 41
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(20)
<223> OTHER INFORMATION: Synthetic primer

<400> SEQUENCE: 41
gaagatggtg atgggatttc                                               20

<210> SEQ ID NO 42
```

```
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(20)
<223> OTHER INFORMATION: Synthetic primer

<400> SEQUENCE: 42
agctctcccg ccggcctctg                                               20

<210> SEQ ID NO 43
<211> LENGTH: 19
<212> TYPE: PRT
<213> ORGANISM: Mus musculus

<400> SEQUENCE: 43

Ala Gln Ala Gly Glu Asp Pro His Gly Tyr Phe Leu Pro Gly Gln Phe
1               5                   10                  15

Ala Phe Ser

<210> SEQ ID NO 44
<211> LENGTH: 12
<212> TYPE: PRT
<213> ORGANISM: Mus musculus

<400> SEQUENCE: 44

His Gly Tyr Phe Leu Pro Gly Gln Phe Ala Phe Ser
1               5                   10

<210> SEQ ID NO 45
<211> LENGTH: 11
<212> TYPE: PRT
<213> ORGANISM: Mus musculus

<400> SEQUENCE: 45

Gly Tyr Phe Leu Pro Gly Gln Phe Ala Phe Ser
1               5                   10

<210> SEQ ID NO 46
<211> LENGTH: 10
<212> TYPE: PRT
<213> ORGANISM: Mus musculus

<400> SEQUENCE: 46

Tyr Phe Leu Pro Gly Gln Phe Ala Phe Ser
1               5                   10

<210> SEQ ID NO 47
<211> LENGTH: 9
<212> TYPE: PRT
<213> ORGANISM: Mus musculus

<400> SEQUENCE: 47

Phe Leu Pro Gly Gln Phe Ala Phe Ser
1               5

<210> SEQ ID NO 48
<211> LENGTH: 8
<212> TYPE: PRT
<213> ORGANISM: Mus musculus

<400> SEQUENCE: 48

Leu Pro Gly Gln Phe Ala Phe Ser
```

-continued

<210> SEQ ID NO 49
<211> LENGTH: 26
<212> TYPE: PRT
<213> ORGANISM: Mus musculus

<400> SEQUENCE: 49

Ile Ala Gln Ala Gly Glu Asp Pro His Gly Tyr Phe Leu Pro Gly Gln
1               5                   10                  15

Phe Ala Phe Ser Arg Ala Leu Arg Thr Lys
            20                  25

<210> SEQ ID NO 50
<211> LENGTH: 21
<212> TYPE: PRT
<213> ORGANISM: Mus musculus

<400> SEQUENCE: 50

Ile Ala Gln Ala Gly Glu Asp Pro His Gly Tyr Phe Leu Pro Gly Gln
1               5                   10                  15

Phe Ala Phe Ser Arg
            20

<210> SEQ ID NO 51
<211> LENGTH: 170
<212> TYPE: PRT
<213> ORGANISM: Homo sapiens

<400> SEQUENCE: 51

Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

Arg Ser Ser Asp Ala Asn Leu Tyr Arg Leu Leu Asp Leu Asp Pro Arg
        50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 52
<211> LENGTH: 25
<212> TYPE: PRT
<213> ORGANISM: Homo sapiens

<400> SEQUENCE: 52

Gln Arg Ala Gly Glu Asp Pro His Ser Phe Tyr Phe Pro Gly Gln Phe

```
1               5                   10                  15
Ala Phe Ser Lys Ala Leu Pro Arg Ser
            20                  25
```

<210> SEQ ID NO 53
<211> LENGTH: 19
<212> TYPE: PRT
<213> ORGANISM: Homo sapiens

<400> SEQUENCE: 53

```
Gln Arg Ala Gly Glu Asp Pro His Ser Phe Tyr Phe Pro Gly Gln Phe
1               5                   10                  15

Ala Phe Ser
```

<210> SEQ ID NO 54
<211> LENGTH: 20
<212> TYPE: PRT
<213> ORGANISM: Homo sapiens

<400> SEQUENCE: 54

```
Gln Arg Ala Gly Glu Asp Pro His Ser Phe Tyr Phe Pro Gly Gln Phe
1               5                   10                  15

Ala Phe Ser Lys
            20
```

<210> SEQ ID NO 55
<211> LENGTH: 18
<212> TYPE: PRT
<213> ORGANISM: Homo sapiens

<400> SEQUENCE: 55

```
Gln Arg Ala Gly Glu Asp Pro His Ser Phe Tyr Phe Pro Gly Gln Phe
1               5                   10                  15

Ala Phe
```

<210> SEQ ID NO 56
<211> LENGTH: 17
<212> TYPE: PRT
<213> ORGANISM: Homo sapiens

<400> SEQUENCE: 56

```
Gln Arg Ala Gly Glu Asp Pro His Ser Phe Tyr Phe Pro Gly Gln Phe
1               5                   10                  15

Ala
```

<210> SEQ ID NO 57
<211> LENGTH: 16
<212> TYPE: PRT
<213> ORGANISM: Homo sapiens

<400> SEQUENCE: 57

```
Gln Arg Ala Gly Glu Asp Pro His Ser Phe Tyr Phe Pro Gly Gln Phe
1               5                   10                  15
```

<210> SEQ ID NO 58
<211> LENGTH: 15
<212> TYPE: PRT
<213> ORGANISM: Homo sapiens

<400> SEQUENCE: 58

```
Gln Arg Ala Gly Glu Asp Pro His Ser Phe Tyr Phe Pro Gly Gln
1               5                   10                  15
```

<210> SEQ ID NO 59
<211> LENGTH: 7
<212> TYPE: PRT
<213> ORGANISM: Homo sapiens

<400> SEQUENCE: 59

Pro Gly Gln Phe Ala Phe Ser
1               5

<210> SEQ ID NO 60
<211> LENGTH: 8
<212> TYPE: PRT
<213> ORGANISM: Homo sapiens

<400> SEQUENCE: 60

Phe Pro Gly Gln Phe Ala Phe Ser
1               5

<210> SEQ ID NO 61
<211> LENGTH: 9
<212> TYPE: PRT
<213> ORGANISM: Homo sapiens

<400> SEQUENCE: 61

Tyr Phe Pro Gly Gln Phe Ala Phe Ser
1               5

<210> SEQ ID NO 62
<211> LENGTH: 10
<212> TYPE: PRT
<213> ORGANISM: Homo sapiens

<400> SEQUENCE: 62

Phe Tyr Phe Pro Gly Gln Phe Ala Phe Ser
1               5                   10

<210> SEQ ID NO 63
<211> LENGTH: 12
<212> TYPE: PRT
<213> ORGANISM: Homo sapiens

<400> SEQUENCE: 63

His Ser Phe Tyr Phe Pro Gly Gln Phe Ala Phe Ser
1               5                   10

<210> SEQ ID NO 64
<211> LENGTH: 13
<212> TYPE: PRT
<213> ORGANISM: Homo sapiens

<400> SEQUENCE: 64

Pro His Ser Phe Tyr Phe Pro Gly Gln Phe Ala Phe Ser
1               5                   10

<210> SEQ ID NO 65
<211> LENGTH: 9
<212> TYPE: PRT
<213> ORGANISM: Homo sapiens

<400> SEQUENCE: 65

Ala Phe Pro Gly Gln Phe Ala Phe Ser
1               5

<210> SEQ ID NO 66
<211> LENGTH: 9

<212> TYPE: PRT
<213> ORGANISM: Homo sapiens

<400> SEQUENCE: 66

Tyr Ala Pro Gly Gln Phe Ala Phe Ser
1               5

<210> SEQ ID NO 67
<211> LENGTH: 9
<212> TYPE: PRT
<213> ORGANISM: Homo sapiens

<400> SEQUENCE: 67

Tyr Phe Ala Gly Gln Phe Ala Phe Ser
1               5

<210> SEQ ID NO 68
<211> LENGTH: 9
<212> TYPE: PRT
<213> ORGANISM: Homo sapiens

<400> SEQUENCE: 68

Tyr Phe Pro Gly Ala Phe Ala Phe Ser
1               5

<210> SEQ ID NO 69
<211> LENGTH: 9
<212> TYPE: PRT
<213> ORGANISM: Homo sapiens

<400> SEQUENCE: 69

Tyr Phe Pro Gly Gln Ala Ala Phe Ser
1               5

<210> SEQ ID NO 70
<211> LENGTH: 9
<212> TYPE: PRT
<213> ORGANISM: Homo sapiens

<400> SEQUENCE: 70

Tyr Phe Pro Gly Gln Phe Ala Ala Ser
1               5

<210> SEQ ID NO 71
<211> LENGTH: 9
<212> TYPE: PRT
<213> ORGANISM: Homo sapiens

<400> SEQUENCE: 71

Tyr Phe Pro Gly Gln Phe Ala Phe Ala
1               5

<210> SEQ ID NO 72
<211> LENGTH: 471
<212> TYPE: DNA
<213> ORGANISM: Homo sapiens

<400> SEQUENCE: 72
atgcgacggc tgctgatccc tctggccctg tggctgggtg cggtgggcgt gggcgtcgcc      60
gagctcacgg aagcccagcg ccggggcctg caggtggccc tggaggaatt tcacaagcac     120
ccgcccgtgc agtgggcctt ccaggagacc agtgtggaga gcgccgtgga cacgcccttc     180
ccagctggaa tatttgtgag gctggaattt aagctgcagc agacaagctg ccggaagagg     240
gactggaaga aacccgagtg caaagtcagg cccaatggga ggaaacggaa atgcctggcc     300

```
tgcatcaaac tgggctctga ggacaaagtt ctgggccggt tggtccactg ccccatagag    360
acccaagttc tgcgggaggc tgaggagcac caggagaccc agtgcctcag ggtgcagcgg    420
gctggtgagg accccacag cttctacttc cctggacagt tcgccttctc c             471
```

```
<210> SEQ ID NO 73
<211> LENGTH: 157
<212> TYPE: PRT
<213> ORGANISM: Homo sapiens

<400> SEQUENCE: 73
```

| Met | Arg | Arg | Leu | Leu | Ile | Pro | Leu | Ala | Leu | Trp | Leu | Gly | Ala | Val | Gly |
|---|---|---|---|---|---|---|---|---|---|---|---|---|---|---|---|
| 1 | | | | 5 | | | | | 10 | | | | | 15 | |

| Val | Gly | Val | Ala | Glu | Leu | Thr | Glu | Ala | Gln | Arg | Arg | Gly | Leu | Gln | Val |
|---|---|---|---|---|---|---|---|---|---|---|---|---|---|---|---|
| | | | 20 | | | | | 25 | | | | | 30 | | |

| Ala | Leu | Glu | Glu | Phe | His | Lys | His | Pro | Pro | Val | Gln | Trp | Ala | Phe | Gln |
|---|---|---|---|---|---|---|---|---|---|---|---|---|---|---|---|
| | | 35 | | | | | 40 | | | | | 45 | | | |

| Glu | Thr | Ser | Val | Glu | Ser | Ala | Val | Asp | Thr | Pro | Phe | Pro | Ala | Gly | Ile |
|---|---|---|---|---|---|---|---|---|---|---|---|---|---|---|---|
| | 50 | | | | | 55 | | | | | 60 | | | | |

| Phe | Val | Arg | Leu | Glu | Phe | Lys | Leu | Gln | Gln | Thr | Ser | Cys | Arg | Lys | Arg |
|---|---|---|---|---|---|---|---|---|---|---|---|---|---|---|---|
| 65 | | | | | 70 | | | | | 75 | | | | | 80 |

| Asp | Trp | Lys | Lys | Pro | Glu | Cys | Lys | Val | Arg | Pro | Asn | Gly | Arg | Lys | Arg |
|---|---|---|---|---|---|---|---|---|---|---|---|---|---|---|---|
| | | | | 85 | | | | | 90 | | | | | 95 | |

| Lys | Cys | Leu | Ala | Cys | Ile | Lys | Leu | Gly | Ser | Glu | Asp | Lys | Val | Leu | Gly |
|---|---|---|---|---|---|---|---|---|---|---|---|---|---|---|---|
| | | | 100 | | | | | 105 | | | | | 110 | | |

| Arg | Leu | Val | His | Cys | Pro | Ile | Glu | Thr | Gln | Val | Leu | Arg | Glu | Ala | Glu |
|---|---|---|---|---|---|---|---|---|---|---|---|---|---|---|---|
| | | | 115 | | | | | 120 | | | | | 125 | | |

| Glu | His | Gln | Glu | Thr | Gln | Cys | Leu | Arg | Val | Gln | Arg | Ala | Gly | Glu | Asp |
|---|---|---|---|---|---|---|---|---|---|---|---|---|---|---|---|
| | | 130 | | | | | 135 | | | | | 140 | | | |

| Pro | His | Ser | Phe | Tyr | Phe | Pro | Gly | Gln | Phe | Ala | Phe | Ser |
|---|---|---|---|---|---|---|---|---|---|---|---|---|
| 145 | | | | | 150 | | | | | 155 | | |

```
<210> SEQ ID NO 74
<211> LENGTH: 13
<212> TYPE: PRT
<213> ORGANISM: Artificial Sequence
<220> FEATURE:
<223> OTHER INFORMATION: Src-related peptide kinase substrate

<400> SEQUENCE: 74
```

| Arg | Arg | Leu | Ile | Glu | Asp | Ala | Glu | Tyr | Ala | Ala | Arg | Gly |
|---|---|---|---|---|---|---|---|---|---|---|---|---|
| 1 | | | | 5 | | | | | 10 | | | |

```
<210> SEQ ID NO 75
<211> LENGTH: 8
<212> TYPE: DNA
<213> ORGANISM: Artificial Sequence
<220> FEATURE:
<223> OTHER INFORMATION: CREB binding site

<400> SEQUENCE: 75 tgacgtca                                                              8
```

```
<210> SEQ ID NO 76
<211> LENGTH: 160
<212> TYPE: PRT
<213> ORGANISM: Rattus norvegicus

<400> SEQUENCE: 76
```

| Met | Lys | Cys | Leu | Leu | Ile | Ser | Leu | Ala | Leu | Trp | Leu | Gly | Thr | Ala | Asp |
|---|---|---|---|---|---|---|---|---|---|---|---|---|---|---|---|
| 1 | | | | 5 | | | | | 10 | | | | | 15 | |

```
Ile His Gly Thr Glu Leu Glu Leu Ser Glu Thr Gln Arg Arg Gly Leu
            20                  25                  30

Gln Val Ala Leu Glu Glu Phe His Arg His Pro Pro Val Gln Trp Ala
        35                  40                  45

Phe Gln Glu Ile Gly Val Asp Ser Ala Asp Asp Leu Phe Phe Ser Ala
    50                  55                  60

Gly Thr Phe Val Arg Leu Glu Phe Lys Leu Gln Gln Thr Ser Cys Leu
65                  70                  75                  80

Lys Lys Asp Trp Lys Lys Pro Glu Cys Thr Ile Lys Pro Asn Gly Arg
                85                  90                  95

Lys Arg Lys Cys Leu Ala Cys Ile Lys Leu Asp Pro Lys Gly Lys Val
            100                 105                 110

Leu Gly Arg Met Val His Cys Pro Ile Leu Lys Gln Gly Pro Gln Gln
        115                 120                 125

Glu Pro Gln Glu Ser Gln Cys Ser Lys Ile Ala Gln Ala Gly Glu Asp
    130                 135                 140

Ser Arg Ile Tyr Phe Phe Pro Gly Gln Phe Ala Phe Ser Arg Ala Leu
145                 150                 155                 160

<210> SEQ ID NO 77
<211> LENGTH: 163
<212> TYPE: PRT
<213> ORGANISM: Sus scrofa

<400> SEQUENCE: 77

Met Trp Gln Leu Leu Leu Pro Leu Ala Leu Trp Leu Gly Thr Met Gly
1               5                   10                  15

Leu Gly Arg Ala Glu Leu Thr Ala Ala Gln Leu Arg Gly Leu Gln Val
            20                  25                  30

Ala Leu Glu Glu Phe His Lys His Pro Pro Val Gln Trp Ala Phe Arg
        35                  40                  45

Glu Thr Gly Val Asn Ser Ala Met Asp Thr Pro Phe Pro Ala Gly Thr
    50                  55                  60

Phe Val Arg Leu Glu Phe Lys Leu Gln Gln Thr Ser Cys Arg Lys Arg
65                  70                  75                  80

Asp Trp Lys Lys Ala Glu Cys Lys Val Lys Pro Asn Gly Arg Lys Arg
                85                  90                  95

Lys Cys Leu Ala Cys Ile Lys Leu Asn Ser Glu Asp Lys Val Leu Gly
            100                 105                 110

Arg Met Val His Cys Pro Ile Glu Thr Gln Val Gln Arg Glu Pro Glu
        115                 120                 125

Glu Arg Gln Glu Ala Gln Cys Ser Arg Val Glu Arg Ala Gly Glu Asp
    130                 135                 140

Pro His Ser Tyr Tyr Phe Pro Gly Gln Phe Ala Phe Phe Lys Ala Leu
145                 150                 155                 160

Pro Pro Ser

<210> SEQ ID NO 78
<211> LENGTH: 160
<212> TYPE: PRT
<213> ORGANISM: Bos taurus

<400> SEQUENCE: 78

Met Trp Gln Leu Leu Leu Pro Leu Ala Leu Gly Leu Gly Thr Met Gly
1               5                   10                  15

Leu Gly Arg Ala Glu Leu Thr Thr Ala Gln His Arg Gly Leu Gln Val
```

```
            20                  25                  30
Ala Leu Glu Glu Phe His Lys His Pro Pro Val Leu Trp Ala Phe Gln
        35                  40                  45

Val Thr Ser Val Asp Asn Ala Ala Asp Thr Leu Phe Pro Ala Gly Gln
 50                  55                  60

Phe Val Arg Leu Glu Phe Lys Leu Gln Gln Thr Ser Cys Arg Lys Lys
 65                  70                  75                  80

Asp Trp Arg Lys Glu Asp Cys Lys Val Lys Pro Asn Gly Arg Lys Arg
                 85                  90                  95

Lys Cys Leu Ala Cys Ile Lys Leu Asp Ser Lys Asp Gln Val Leu Gly
                100                 105                 110

Arg Met Val His Cys Pro Ile Gln Thr Gln Val Gln Arg Glu Leu Asp
                115                 120                 125

Asp Ala Gln Asp Ala Gln Cys Ser Arg Val Glu Arg Ala Gly Glu Asp
            130                 135                 140

Pro His Ser Tyr Tyr Leu Pro Gly Gln Phe Ala Phe Ile Lys Ala Leu
145                 150                 155                 160

<210> SEQ ID NO 79
<211> LENGTH: 165
<212> TYPE: PRT
<213> ORGANISM: Gallus gallus

<400> SEQUENCE: 79

Arg Ala Val Gly Met Lys Leu Leu Gly Ile Ala Val Val Leu
1                5                  10                  15

Ala Leu Ala Asp Ala Gly Gln Ser Pro Leu Gln Arg Arg Val Val Lys
                 20                  25                  30

Asp Val Leu Asp Tyr Phe His Ser Arg Ser Asn Val Gln Phe Leu Phe
             35                  40                  45

Arg Glu Gln Ser Val Glu Gly Ala Val Glu Arg Val Asp Ser Ser Gly
 50                  55                  60

Thr Phe Val Gln Leu His Leu Asn Leu Ala Gln Thr Ala Cys Arg Lys
 65                  70                  75                  80

Gln Ala Gln Arg Lys Gln Asn Cys Arg Ile Met Glu Asn Arg Arg Lys
                 85                  90                  95

Pro Val Cys Leu Ala Cys Tyr Lys Phe Asp Ser Ser Ala Val Pro Lys
                100                 105                 110

Val Leu Asp Lys Tyr Tyr Asn Cys Gly Pro Ser His His Leu Ala Met
             115                 120                 125

Lys Asp Ile Lys His Arg Asp Glu Ala Glu Cys Arg Ala Val Glu Glu
            130                 135                 140

Ala Gly Lys Thr Ser Asp Val Leu Tyr Leu Pro Gly Met Phe Ala Phe
145                 150                 155                 160

Ser Lys Gly Leu Pro
                165

<210> SEQ ID NO 80
<211> LENGTH: 7
<212> TYPE: PRT
<213> ORGANISM: Artificial Sequence
<220> FEATURE:
<223> OTHER INFORMATION: Substrate peptide for Protein Kinase C
<220> FEATURE:
<221> NAME/KEY: PEPTIDE
<222> LOCATION: (1)..(7)
<223> OTHER INFORMATION: Substrate peptide

<400> SEQUENCE: 80
```

```
Phe Lys Lys Ser Phe Lys Leu
1               5

<210> SEQ ID NO 81
<211> LENGTH: 11
<212> TYPE: DNA
<213> ORGANISM: Artificial Sequence
<220> FEATURE:
<223> OTHER INFORMATION: Consensus NF-kappa B binding site
<220> FEATURE:
<221> NAME/KEY: misc_binding
<222> LOCATION: (1)..(11)
<223> OTHER INFORMATION: Consensus binding element sequence

<400> SEQUENCE: 81
ggggactttc c                                                          11

<210> SEQ ID NO 82
<211> LENGTH: 6
<212> TYPE: PRT
<213> ORGANISM: Homo sapiens

<400> SEQUENCE: 82

Lys Ala Leu Pro Arg Ser
1               5

<210> SEQ ID NO 83
<211> LENGTH: 17
<212> TYPE: PRT
<213> ORGANISM: Homo sapiens

<400> SEQUENCE: 83

Ala Gly Glu Asp Pro His Ser Phe Tyr Phe Pro Gly Gln Phe Ala Phe
1               5                   10                  15

Ser

<210> SEQ ID NO 84
<211> LENGTH: 15
<212> TYPE: PRT
<213> ORGANISM: Homo sapiens

<400> SEQUENCE: 84

Glu Asp Pro His Ser Phe Tyr Phe Pro Gly Gln Phe Ala Phe Ser
1               5                   10                  15

<210> SEQ ID NO 85
<211> LENGTH: 11
<212> TYPE: PRT
<213> ORGANISM: Homo sapiens

<400> SEQUENCE: 85

Ser Phe Tyr Phe Pro Gly Gln Phe Ala Phe Ser
1               5                   10

<210> SEQ ID NO 86
<211> LENGTH: 6
<212> TYPE: PRT
<213> ORGANISM: Homo sapiens

<400> SEQUENCE: 86

Gly Gln Phe Ala Phe Ser
1               5

<210> SEQ ID NO 87
<211> LENGTH: 5
```

```
<212> TYPE: PRT
<213> ORGANISM: Homo sapiens

<400> SEQUENCE: 87

Gln Phe Ala Phe Ser
1               5

<210> SEQ ID NO 88
<211> LENGTH: 9
<212> TYPE: PRT
<213> ORGANISM: Homo sapiens

<400> SEQUENCE: 88

Tyr Phe Pro Ala Gln Phe Ala Phe Ser
1               5

<210> SEQ ID NO 89
<211> LENGTH: 8
<212> TYPE: PRT
<213> ORGANISM: Homo sapiens

<400> SEQUENCE: 89

Phe Ser Lys Ala Leu Pro Arg Ser
1               5

<210> SEQ ID NO 90
<211> LENGTH: 7
<212> TYPE: PRT
<213> ORGANISM: Homo sapiens

<400> SEQUENCE: 90

Glu Leu Thr Glu Ala Gln Arg
1               5

<210> SEQ ID NO 91
<211> LENGTH: 13
<212> TYPE: PRT
<213> ORGANISM: Homo sapiens

<400> SEQUENCE: 91

Tyr His Ser Phe Phe Phe Pro Gly Gln Phe Ala Phe Ser
1               5                   10

<210> SEQ ID NO 92
<211> LENGTH: 9
<212> TYPE: PRT
<213> ORGANISM: Artificial Sequence
<220> FEATURE:
<223> OTHER INFORMATION: binds to a ChemerinR polypeptide
<220> FEATURE:
<221> NAME/KEY: MISC_FEATURE
<222> LOCATION: (3)..(5)
<223> OTHER INFORMATION: Each X is any amino acid
<220> FEATURE:
<221> NAME/KEY: MISC_FEATURE
<222> LOCATION: (7)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid

<400> SEQUENCE: 92

Tyr Phe Xaa Xaa Xaa Phe Xaa Phe Xaa
1               5

<210> SEQ ID NO 93
<211> LENGTH: 9
```

```
<212> TYPE: PRT
<213> ORGANISM: Artificial Sequence
<220> FEATURE:
<223> OTHER INFORMATION: Binds specifically to ChemerinR
<220> FEATURE:
<221> NAME/KEY: MISC_FEATURE
<222> LOCATION: (4)..(4)
<223> OTHER INFORMATION: X is selected from the group consisting of GLY,
      ALA, VAL, LEU, ILE, SER and  THR
<220> FEATURE:
<221> NAME/KEY: MISC_FEATURE
<222> LOCATION: (5)..(5)
<223> OTHER INFORMATION: X is either GLU or ASN
<220> FEATURE:
<221> NAME/KEY: MISC_FEATURE
<222> LOCATION: (7)..(7)
<223> OTHER INFORMATION: X is selected from the group consisting of GLY,
      ALA, VAL, LEU, ILE, SER and  THR
<220> FEATURE:
<221> NAME/KEY: MISC_FEATURE
<222> LOCATION: (9)..(9)
<223> OTHER INFORMATION: X is selected from the group consisting of GLY,
      ALA, VAL, LEU, ILE, SER and  THR

<400> SEQUENCE: 93

Tyr Phe Pro Xaa Xaa Phe Xaa Phe Xaa
1               5

<210> SEQ ID NO 94
<211> LENGTH: 9
<212> TYPE: PRT
<213> ORGANISM: Artificial Sequence
<220> FEATURE:
<223> OTHER INFORMATION: Binds specifically to ChemerinR
<220> FEATURE:
<221> NAME/KEY: MISC_FEATURE
<222> LOCATION: (1)..(2)
<223> OTHER INFORMATION: Each X is any aromatic amino acid
<220> FEATURE:
<221> NAME/KEY: MISC_FEATURE
<222> LOCATION: (3)..(5)
<223> OTHER INFORMATION: each X is any amino acid
<220> FEATURE:
<221> NAME/KEY: MISC_FEATURE
<222> LOCATION: (6)..(6)
<223> OTHER INFORMATION: X is any aromatic amino acid
<220> FEATURE:
<221> NAME/KEY: MISC_FEATURE
<222> LOCATION: (7)..(7)
<223> OTHER INFORMATION: X is any amino acid
<220> FEATURE:
<221> NAME/KEY: MISC_FEATURE
<222> LOCATION: (8)..(8)
<223> OTHER INFORMATION: X is any aromatic amino acid
<220> FEATURE:
<221> NAME/KEY: MISC_FEATURE
<222> LOCATION: (9)..(9)
<223> OTHER INFORMATION: X is any amino acid

<400> SEQUENCE: 94

Xaa Xaa Xaa Xaa Xaa Xaa Xaa Xaa Xaa
1               5

<210> SEQ ID NO 95
<211> LENGTH: 6
<212> TYPE: PRT
<213> ORGANISM: Homo sapiens

<400> SEQUENCE: 95

Lys Ala Leu Pro Arg Ser
1               5

<210> SEQ ID NO 96
<211> LENGTH: 15
```

```
<212> TYPE: PRT
<213> ORGANISM: Homo sapiens

<400> SEQUENCE: 96

Glu Asp Pro His Ser Phe Tyr Phe Pro Gly Gln Phe Ala Phe Ser
1               5                   10                  15

<210> SEQ ID NO 97
<211> LENGTH: 11
<212> TYPE: PRT
<213> ORGANISM: Homo sapiens

<400> SEQUENCE: 97

Ser Phe Tyr Phe Pro Gly Gln Phe Ala Phe Ser
1               5                   10

<210> SEQ ID NO 98
<211> LENGTH: 10
<212> TYPE: PRT
<213> ORGANISM: Homo sapiens

<400> SEQUENCE: 98

Phe Tyr Phe Pro Gly Gln Phe Ala Phe Ser
1               5                   10

<210> SEQ ID NO 99
<211> LENGTH: 7
<212> TYPE: PRT
<213> ORGANISM: Homo sapiens

<400> SEQUENCE: 99

Pro Gly Gln Phe Ala Phe Ser
1               5

<210> SEQ ID NO 100
<211> LENGTH: 6
<212> TYPE: PRT
<213> ORGANISM: Homo sapiens

<400> SEQUENCE: 100

Gly Gln Phe Ala Phe Ser
1               5

<210> SEQ ID NO 101
<211> LENGTH: 5
<212> TYPE: PRT
<213> ORGANISM: Homo sapiens

<400> SEQUENCE: 101

Gln Phe Ala Phe Ser
1               5

<210> SEQ ID NO 102
<211> LENGTH: 9
<212> TYPE: PRT
<213> ORGANISM: Homo sapiens

<400> SEQUENCE: 102

Tyr Phe Pro Ala Gln Phe Ala Phe Ser
1               5
```

NUCLEIC ACIDS ENCODING CHEMERINR LIGANDS

This application is a Divisional of U.S. Ser. No. 10/603,566, filed Jun. 25, 2003 now U.S. Pat. No. 7,419,658, which is a continuation in part of U.S. application Ser. No. 10/201,187, filed on Jul. 23, 2002 now abandoned, which is a continuation in part of U.S. application Ser. No. 09/905,253, filed Jul. 13, 2001 now abandoned, which claims priority under 35 U.S.C. §119(e) to U.S. Provisional application No. 60/303,858, filed Jul. 9, 2001.

FIELD OF THE INVENTION

The invention relates to the identification of the natural ligand for the orphan G-Protein Coupled Receptor (GPCR) ChemerinR and uses thereof in diagnosis and immuno therapy of a disease.

BACKGROUND OF THE INVENTION

G-protein coupled receptors (GPCRs) are proteins responsible for transducing a signal within a cell. GPCRs have usually seven transmembrane domains. Upon binding of a ligand to an extra-cellular portion or fragment of a GPCR, a signal is transduced within the cell that results in a change in a biological or physiological property or behaviour of the cell. GPCRs, along with G-proteins and effectors (intracellular enzymes and channels modulated by G-proteins), are the components of a modular signaling system that connects the state of intra-cellular second messengers to extra-cellular inputs.

GPCR genes and gene products can modulate various physiological processes and are potential causative agents of disease. The GPCRs seem to be of critical importance to both the central nervous system and peripheral physiological processes.

The GPCR protein superfamily is represented in five families: Family I, receptors typified by rhodopsin and the beta2-adrenergic receptor and currently represented by over 200 unique member; Family II, the parathyroid hormone/calcitonin/secretin receptor family; Family III, the metabotropic glutamate receptor family, Family IV, the CAMP receptor family, important in the chemotaxis and development of D. discoideum; and Family V, the fungal mating pheromone receptor such as STE2.

G proteins represent a family of heterotrimeric proteins composed of α, β and γ subunits, that bind guanine nucleotides. These proteins are usually linked to cell surface receptors (receptors containing seven transmembrane domains) for signal transduction. Indeed, following ligand binding to the GPCR, a conformational change is transmitted to the G protein, which causes the α-subunit to exchange a bound GDP molecule for a GTP molecule and to dissociate from the βγ-subunits.

The GTP-bound form of the α, β and γ-subunits typically functions as an effector-modulating moiety, leading to the production of second messengers, such as cAMP (e.g. by activation of adenyl cyclase), diacylglycerol or inositol phosphates.

Greater than 20 different types of α-subunits are known in humans. These subunits associate with a small pool of β and γ subunits. Examples of mammalian G proteins include Gi, Go, Gq, Gs and Gt. G proteins are described extensively in Lodish et al., *Molecular Cell Biology* (Scientific American Books Inc., New York, N.Y., 1995; and also by Downes and Gautam, 1999, The G-Protein Subunit Gene Families. *Genomics* 62:544-552), the contents of both of which are incorporated herein by reference.

Known and uncharacterized GPCRs currently constitute major targets for drug action and development. There are ongoing efforts to identify new G protein coupled receptors which can be used to screen for new agonists and antagonists having potential prophylactic and therapeutic properties.

More than 300 GPCRs have been cloned to date, excluding the family of olfactory receptors. Mechanistically, approximately 50-60% of all clinically relevant drugs act by modulating the functions of various GPCRs (Cudermann et al., *J. Mol. Med.*, 73:51-63, 1995).

ChemerinR, also called Dez [Sequence ID Nos:1 (human polynucleotide sequence, FIG. 1); 2 (human amino acid sequence, FIG. 2); 3 (mouse polynucleotide sequence, FIG. 3); 4 (mouse amino acid sequence, FIG. 3); 5 (rat polynucleotide sequence; FIG. 4); and 6 (rat amino acid sequence, FIG. 4)] has been described as an orphan G protein coupled receptor related to GPR-1 (38% overall amino acid identity), C3a receptor (38%), C5a anaphylatoxin receptor (36%) and formyl Met-Leu-Phe receptors (35%). ChemerinR is more distantly related to the chemokine receptors subfamily (Methner A, Hermey G, Schinke B, Hermans-Borgmeyer I. (1997) *Biochem Biophys Res Commun* 233:336-42; Samson M, Edinger A L, Stordeur P, Rucker J, Verhasselt V, Sharron M, Govaerts C, Mollereau C, Vassart G, Doms R W, Parmentier M. (1998) *Eur J Immunol* 28:1689-700). ChemerinR transcripts were found to be abundant in monocyte-derived dendritic cells and macrophages, with or without treatment with LPS. Low expression can also be detected by reverse transcription-PCR in CD4+ T lymphocytes. In situ hybridization experiments also showed that the receptor was differentially regulated during development, with a prominent expression in developing osseous and cartilaginous tissues. It was also detectable in the adult parathyroid glands, indicating a possible function in phosphocalic metabolism.

The gene encoding ChemerinR was assigned by radiation hybrid mapping to the q21.2-21.3 region of human chromosome 12, outside the gene clusters identified so far for chemoattractant receptors. ChemerinR was tested in fusion assays for potential coreceptor activity by a range of HIV-1, HIV-2 and SIV viral strains. Several SIV strains (SIVmac316, SIVmac239, SIVmacl7E-Fr and SIVsm62A), as well as a primary HIV-1 strain (92UG024-2) efficiently used ChemerinR as a co-receptor. This receptor therefore appears to be a coreceptor for immunodeficiency viruses that does not belong to the chemokine receptor family. It is also a putative chemoattractant receptor and it could play an important role in the recruitment or trafficking of leukocyte cell populations. ChemerinR, by its specific expression in macrophages and immature dendritic cells, appears as a particularly attractive candidate receptor involved in the initiation and early regulation of immune responses.

TIG2 (Tazarotene-induced gene 2, thereafter Preprochemerin [Sequence ID Nos: 7 (human Preprochemerin polynucleotide sequence, FIG. 6); 8 (human amino acid sequence, FIG. 6); 9 (mouse polynucleotide sequence, FIG. 7); and 10 (mouse amino acid sequence, FIG. 7)] was identified as a cDNA, the expression of which is up-regulated by the treatment of skin raft cultures by the retinoic acid receptor (RAR) beta/gamma-selective anti-psoriatic synthetic retinoid, tazarotene [AGN 190168/ethyl 6-[2-(4,4-dimethylthio-chroman-6-yl)-ethynyl]nicotinate] (Nagpal S, Patel S, Jacobe H, DiSepio D, Ghosn C, Malhotra M, Teng M, Duvic M, Chandraratna R A. (1997) *J Invest Dermatol* 109: 91-5). The retinoid-mediated up-regulation in the expression of Preprochemerin was confirmed by Northern blot analysis. The Preprochemerin is located at 17p13.3 position, a region associated with pancretic tumorigenesis. The Preprochemerin cDNA is 830 bp long and encodes a putative protein product of 163 amino acids. Preprochemerin is expressed and induced by tazarotene in culture only when keratinocytes and fibroblasts form a tissue-like 3-dimensional structure. RAR-specific retinoids were also shown to increase Preprochemerin mRNA levels. In contrast, neither RXR-specific retinoids nor 1,25-dihydroxyvitamin D3 increased Preprochemerin levels in these cells. Preprochemerin is also expresssed at high levels in nonlesional psoriatic skin but at lower levels in the psoriatic lesion and its expression is up-regulated in psoriatic lesions after topical application of tazarotene. In addition, Preprochemerin has been shown to be dramatically upregulated by 1,25 dihydroxyvitamin D3 and dexamethasone in osteoclast-supporting stromal cells (Adams A E, Abu-Amer Y, Chappel J, Stueckle S, Ross F P, Teitelbaum S L, Suva L J. (1999) *J Cell Biochem* 74: 587-95).

Dendritic cells (DCs) and macrophages are professional antigen-presenting cells that play key roles in both innate and adaptive immunity. DCs and macrophages are attracted to infection and inflammatory sites by a variety of factors, among which chemokines constitute the largest group so far (Caux, C. et al. (2002) *Transplantation* 73: S7-S11, Mellman, I. and Steinman, R M (2001) *Cell* 106:255-258). It has been shown that tremendous functional, morphological and metabolic diversity exists among these cell populations. One of these functional differences is the expression of differential sets of chemoattractant receptors, which is responsible for the selective recruitment of specific cell subpopulations, according to their lineage, origin and maturation state (Caux, C. et al. (2002) *Transplantation* 73: S7-S11). Many tumor types have been demonstrated to attract macrophages and DCs through the direct or indirect production of chemoattractant factors (Coussens, L M and Werb, Z. (2002) *Nature* 420:860-867, Vicari, A P and Caux, C. (2002) *Cytokine Growth Factors Rev.* 13:143-154). These include a number of CC-chemokines, such as MCP-1.

DCs are specialized antigen-presenting cells located throughout the human body. DCs function as sentinels of the immune system. They serve as essential link between innate and adaptive immune systems and induce both primary and secondary immune responses (Palucka, K A and Banchereau, J. (1999) *J. Clin. Immunol.* 19:12-25). They traffic from the blood to the tissues where, while immature, they capture antigens. They then leave the tissues and move to the draining lymphoid organs where, coverted into mature DCs, they initiate the immune response by activating naïve CD8$^+$ cells, which seek out and kill the antigen-expressing tumor cells. Chemokines are important effectors of the regulation of DCs recruitment, and depending on the chemokine gradient released at the site of injury, different DC populations will be recruited. It is expected that the type of resulting immune response will likely be dependent on the DC subpopulation recruited and thus on the chemokines secreted (Caux, C. et al. (2002) *Transplantation* 73: S7-S11).

SUMMARY OF THE INVENTION

The invention is based on the discovery that Chemerin, a polypeptide resulting from the proteolytic processing of the Proprechemerin precursor, is a natural ligand of the ChemerinR, and binds specifically to ChemerinR. The invention encompasses a class of polypeptide sequences issued from the C-terminal end of Chemerin containing a sequence motif N1N2X1X2X3N3X4N4X5 (SEQ ID NO: 94) wherein N1-N4 are aromatic amio acids and X1-X5 are any amino acid, as well as the nucleic acid sequences encoding this sequence motif. In one embodiment, the polypeptide comprises YFX1X2X3FX4FX5 (SEQ ID NO: 92). In another embodiment, the polypeptide comprises YFPGQFAFS (SEQ ID NO: 61). In another embodiment, the polypeptide comprises QRAGEDPHSFYFPGQFAFS (SEQ ID NO: 53).

The invention also encompasses the nucleic acid and polypeptide sequences of Chemerin from mammals. The invention further encompasses the polynucleic acid and peptide sequences of truncated Chemerin. The invention further encompasses the functionally-equivalent analogs of Chemerin nucleic acid and polypeptide sequences that contain various substitutions from the naturally-occurring sequences.

The invention further encompasses expressing vectors encoding polypeptides that specifically bind to a ChemerinR polypeptide. In one embodiment, the expressing vector encodes the polypeptide or peptide sequences comprising N1N2X1X2X3N3X4N4X5 (SEQ ID NO: 94), wherein N1-N3 are aromatic amino acids and X1-X5 are any amino acids. In another embodiment, the expressing vector encodes the polypeptide sequences comprising YFX1X2X3FX4FX5 (SEQ ID NO: 92). In another embodiment, the expressing vector encodes the polypeptides comprising YFPGQFAFS (SEQ ID NO: 61). In another embodiment, the expressing vector encodes the polypeptides comprising QRAGEDPHSFYFPGQFAFS (SEQ ID NO: 53). In another embodiment, the expressing vector encodes a Preprochemerin polypeptide as depicted in SEQ ID NO: 47.

The invention further encompasses antibodies to a Chemerin polypeptide. In one embodiment, the antibody is polyclonal antibody. In another embodiment, the antibody is monoclonal antibody. In another embodiment, the monoclonal antibody specifically binds to an epitope comprising FSKALPRS (SEQ ID NO 89).

The invention further encompasses a composition containing any one of the above identified polypeptides. The invention further encompasses a composition containing any one of the above identified nucleic acid sequences. In one embodiment, the composition is a therapeutic composition containing the polypeptide/nucleic acid sequences in a acceptable carrier.

The invention further encompasses the use of the interaction of ChemerinR polypeptides and Chemerin polypeptides as the basis of screening assays for agents that modulate the activity of the ChemerinR receptor.

The invention encompasses a method of identifying an agent that modulates the function of ChemerinR, the method comprising: a) contacting a ChemerinR polypeptide with a Chemerin polypeptide in the presence and absence of a candidate modulator under conditions permitting the binding of the Chemerin polypeptide to the ChemerinR polypeptide; and b) measuring the binding of the ChemerinR polypeptide to the Chemerin polypeptide, wherein a decrease in binding in the presence of the candidate modulator, relative to the binding in the absence of the candidate modulator, identifies the candidate modulator as an agent that modulates the function of ChemerinR.

The invention further encompasses a method of detecting the presence, in a sample, of an agent that modulates the function of ChemerinR in a sample, the method comprising a) contacting a ChemerinR polypeptide with a Chemerin polypeptide in the presence and absence of the sample under conditions permitting the binding of the Chemerin polypeptide to the ChemerinR polypeptide; and b) measuring the binding of the ChemerinR polypeptide to the Chemerin polypeptide, wherein a decrease in binding in the presence of the sample, relative to the binding in the absence of the candidate modulator, indicates the presence, in the sample of an agent that modulates the function of ChemerinR.

In a preferred embodiment of either of the preceding methods, the measuring is performed using a method selected from label displacement, surface plasmon resonance, fluorescence resonance energy transfer, fluorescence quenching, and fluorescence polarization.

The invention further encompasses a method of identifying an agent that modulates the function of ChemerinR, the method comprising: a) contacting a ChemerinR polypeptide with a Chemerin polypeptide in the presence and absence of a candidate modulator; and b) measuring a signaling activity of the ChemerinR polypeptide, wherein a change in the activity in the presence of the candidate modulator relative to the activity in the absence of the candidate modulator identifies the candidate modulator as an agent that modulates the function of ChemerinR.

The invention further encompasses a method of identifying an agent that modulates the function of ChemerinR, the method comprising: a) contacting a ChemerinR polypeptide with a candidate modulator; b) measuring a signaling activity of the ChemerinR polypeptide in the presence of the candidate modulator; and c) comparing the activity measured in the presence of the candidate modulator to the activity measured in a sample in which the ChemerinR polypeptide is contacted with a Chemerin polypeptide at its $EC_{50}$, wherein the candidate modulator is identified as an agent that modulates the function of ChemerinR when the amount of the activity measured in the presence of the candidate modulator is at least 50% of the amount induced by the Chemerin polypeptide present at its $EC_{50}$.

The invention further encompasses a method of detecting the presence, in a sample, of an agent that modulates the function of ChemerinR, the method comprising: a) contacting a ChemerinR polypeptide with Chemerin polypeptide in the presence and absence of the sample; b) measuring a signaling activity of the ChemerinR polypeptide; and c) comparing the amount of the activity measured in a reaction containing ChemerinR and Chemerin polypeptides without the sample to the amount of the activity measured in a reaction containing ChemerinR, Chemerin and the sample, wherein a change in the activity in the presence of the sample relative to the activity in the absence of the sample indicates the presence, in the sample, of an agent that modulates the function of ChemerinR.

The invention further encompasses a method of detecting the presence, in a sample, of an agent that modulates the function of ChemerinR, the method comprising: a) contacting a ChemerinR polypeptide with the sample; b) measuring a signaling activity of the ChemerinR polypeptide in the presence of the sample; and c) comparing the activity measured in the presence of the sample to the activity measured in a reaction in which the ChemerinR polypeptide is contacted with a Chemerin polypeptide present at its $EC_{50}$, wherein an agent that modulates the function of ChemerinR is detected if the amount of the activity measured in the presence of the sample is at least 50% of the amount induced by the Chemerin polypeptide present at its $EC_{50}$.

In a preferred embodiment of each of the preceding methods, the Chemerin polypeptide is detectably labeled. It is preferred that the Chemerin polypeptide is detectably labeled with a moiety selected from the group consisting of a radioisotope, a fluorophore, a quencher of fluorescence, an enzyme, an affinity tag, and an epitope tag.

In one embodiment of any of the preceding methods, the contacting is performed in or on a cell expressing the ChemerinR polypeptide.

In another embodiment of any of the preceding methods, the contacting is performed in or on synthetic liposomes (see Tajib et al., 2000, *Nature Biotechnology:* 649-654 which is incorporated herein by reference) or virus-induced budding membranes containing a ChemerinR polypeptide. (See WO0102551, 2001, incorporated herein by reference).

In another embodiment of any of the preceding methods, the method is performed using a membrane fraction from cells expressing the ChemerinR polypeptide.

In another embodiment, the agent is selected from the group consisting of a peptide, a polypeptide, an antibody or antigen-binding fragment thereof, a lipid, a carbohydrate, a nucleic acid, and a small organic molecule.

In another embodiment, the step of measuring a signaling activity of the ChemerinR polypeptide comprises detecting a change in the level of a second messenger.

In another embodiment, the step of measuring a signaling activity comprises measurement of guanine nucleotide binding or exchange, adenylate cyclase activity, cAMP, Protein Kinase C activity, phosphatidylinosotol breakdown, diacylglycerol, inositol triphosphate, intracellular calcium, arachinoid acid, MAP kinase activity, tyrosine kinase activity, or reporter gene expression.

In a preferred embodiment, the measuring a signaling activity comprises using an aequorin-based assay.

The invention further encompasses a method of modulating the activity of a ChemerinR polypeptide in a cell, the method comprising the step of delivering to the cell an agent that modulates the activity of a ChemerinR polypeptide, such that the activity of ChemerinR is modulated.

The invention further encompasses a method of diagnosing a disease or disorder characterized by dysregulation of ChemerinR signaling, the method comprising: a) contacting a tissue sample with an antibody specific for a ChemerinR polypeptide; b) detecting binding of the antibody to the tissue sample; and c) comparing the binding detected in step (b) with a standard, wherein a difference in binding relative to the standard is diagnostic of a disease or disorder characterized by dysregulation of ChemerinR.

The invention further encompasses a method of diagnosing a disease or disorder characterized by dysregulation of ChemerinR signaling, the method comprising: a) contacting a tissue sample with an antibody specific for a Chemerin polypeptide; b) detecting binding of the antibody to the tissue sample; and c) comparing the binding detected in step (b) with a standard, wherein a difference in binding relative to the standard is diagnostic of a disease or disorder characterized by dysregulation of ChemerinR.

The invention also encompasses diagnostic assays based upon the ChemerinR/Chemerin polypeptide interaction, as well as kits for performing diagnostic and screening assays.

The invention further encompasses a method of diagnosing a disease or disorder characterized by dysregulation of ChemerinR signaling, the method comprising: a) contacting a tissue sample with an antibody specific for a ChemerinR polypeptide and an antibody specific for a Chemerin polypeptide; b) detecting binding of the antibodies to the tissue sample; and c) comparing the binding detected in step (b) with a standard, wherein a difference in the binding of either antibody or both, relative to the standard, is diagnostic of a disease or disorder characterized by dysregulation of ChemerinR.

The invention further encompasses a method of diagnosing a disease or disorder characterized by dysregulation of ChemerinR signaling, the method comprising: a) isolating nucleic acid from a tissue sample; b) amplifying a ChemerinR polynucleotide, using the nucleic acid as a template; and c) comparing the amount of amplified ChemerinR polynucleotide produced in step (b) with a standard, wherein a difference in the amount of amplified ChemerinR polynucleotide relative to the standard is diagnostic of a disease or disorder characterized by dysregulation of ChemerinR. In a preferred embodiment, the step of amplifying comprises RT/PCR. In another preferred embodiment, the step of comparing the amount is performed on a micro array.

The invention further encompasses a method of diagnosing a disease or disorder characterized by dysregulation of ChemerinR signaling, the method comprising: a) isolating nucleic acid from a tissue sample; b) amplifying a ChemerinR polynucleotide, using the nucleic acid as a template; and c) comparing the sequence of the amplified ChemerinR polynucleotide produced in step (b) with a standard, wherein a difference in the sequence, relative to the standard is diagnostic of a disease or disorder characterized by dysregulation of ChemerinR. In a preferred embodiment, the step of amplifying comprises RT/PCR. In another preferred embodiment, the standard is SEQ ID NO: 1. In another preferred embodiment, the step of comparing the sequence comprises minisequencing. In another preferred embodiment, the step of comparing the sequence is performed on a microarray.

The invention further encompasses a method of diagnosing a disease or disorder characterized by dysregulation of ChemerinR signaling, the method comprising: a) isolating nucleic acid from a tissue sample; b) amplifying a Chemerin polynucleotide, using the nucleic acid as a template; and c) comparing the amount of amplified Chemerin polynucleotide produced in step (b) with a standard, wherein a difference in the amount of amplified Chemerin polynucleotide relative to the standard is diagnostic of a disease or disorder characterized by dysregulation of ChemerinR. In a preferred embodiment, the step of amplifying comprises RT/PCR. In another preferred embodiment, the step of comparing the amount is performed on a micro array.

The invention further encompasses a method of diagnosing a disease or disorder characterized by dysregulation of ChemerinR signaling, the method comprising: a) isolating nucleic acid from a tissue sample; b) amplifying a Chemerin polynucleotide, using the nucleic acid as a template; and c) comparing the sequence of the amplified Chemerin polynucleotide produced in step (b) with a standard, wherein a difference in the sequence, relative to the standard is diagnostic of a disease or disorder characterized by dysregulation of ChemerinR. In a preferred embodiment, the step of amplifying comprises RT/PCR. In another preferred embodiment, the standard is SEQ ID NO: 7. In another preferred embodiment, the step of comparing the sequence comprises minisequencing. In another preferred embodiment, the step of comparing the sequence is performed on a microarray.

The invention further encompasses a composition comprising an isolated ChemerinR polypeptide.

The invention further encompasses an antibody specific for a ChemerinR polypeptide.

The invention further encompasses a kit for screening for agents that modulate ChemerinR signaling, or for the diagnosis of a disease or disorder characterized by dysregulation of a ChemerinR polypeptide, the kit comprising an isolated ChemerinR polypeptide and packaging materials therefor. In a preferred embodiment, the kit further comprises a Chemerin polypeptide. Diagnostic kits according to the invention permit the determination of whether, for example, a tissue sample or an extract prepared from a tissue sample has an elevated level or activity of Chemerin or ChemerinR. The kits also permit the identification of mutations in genes encoding ChemerinR or Chemerin and detection of abnormal levels of nucleic acids encoding ChemerinR or Chemerin.

The invention further encompasses a kit for screening for agents that modulate ChemerinR signaling, or for the diagnosis of a disease or disorder characterized by dysregulation of a ChemerinR polypeptide, the kit comprising an isolated polynucleotide encoding a ChemerinR polypeptide and packaging materials therefor. In a preferred embodiment, the kit further comprises an isolated polynucleotide encoding a Chemerin polypeptide.

The invention further encompasses a kit for screening for agents that modulate ChemerinR signaling, or for the diagnosis of a disease or disorder characterized by dysregulation of a ChemerinR polypeptide, the kit comprising a cell transformed with a polynucleotide encoding a ChemerinR polypeptide and packaging materials therefor. In a preferred embodiment, the kit further comprises an isolated polynucleotide encoding a Chemerin polypeptide or a cell comprising a polynucleotide encoding a Chemerin polypeptide.

The invention further encompasses a non-human mammal having a homozygous null mutation in the gene encoding ChemerinR.

The invention further encompasses a non-human mammal transgenic for a ChemerinR polynucleotide.

The invention further encompasses a non-human mammal transgenic for a Chemerin polynucleotide.

The invention further encompasses a method for gene transfer of Preprochemerin (SEQ ID NO: 7) or a gene transfer of truncated Preprochemerin (SEQ ID NO: 72) into a cell. The invention further encompasses a method for gene transfer of Preprochemerin or a gene transfer of truncated Preprochemerin directly into tissues in vivo for treatment of a disease or disorder. The gene transfer may employ DNA expressing plasmid vectors, or viral vectors, or non-viral gene transfer tools such as liposomes, receptor-mediated endocytosis, and gene gun. In one particular embodiment, the vector is expressed in a tissue-specific and tumor-selective manner.

The invention further encompasses an ex vivo gene therapy with the gene encoding the Preprochemerin or the gene encoding truncated Preprochemerin.

The invention further encompasses an ex vivo gene transfection of Preprochemerin or truncated Preprochemerin into a disease cell and the subsequent graft of the transfected cell in vivo for assaying the anti-disease effect of Preprochemerin or truncated Preprochemerin in vivo.

The invention further encompasses an in vivo gene therapy with the gene encoding the Preprochemerin or truncated Preprochemerin. One embodiment of the invention includes administering the gene encoding Preprochemerin or truncated Preprochemerin polynucleotides into a subject for stimulating immuno response or therapeutic treatment of a disease.

BRIEF DESCRIPTION OF THE FIGURES

FIG. 1 shows the nucleotide (SEQ ID NO: 1) and deduced amino acid sequence of human ChemerinR/Dezb/CMKRL1.

FIG. 2 shows the amino acid sequence of human ChemerinR/Dezb/CMKRL1 (SEQ ID NO: 2). The seven predicted transmembrane domains are underlined. The consensus sequence for N-linked glycosylation (N-X-S/T) in the N terminus is bold, and the potential site of phosphorylation by PKC (S/T-X-R/K) in the C terminus is italicized.

FIG. 3 shows the nucleotide (SEQ ID NO:3) and deduced amino acid (SEQ ID NO: 4) sequences of mouse Dez, the mouse orthologue of ChemerinR.

FIG. 4 shows that nucleotide (SEQ ID NO: 5) and deduced amino acid (SEQ ID NO: 6) sequences of rat G-Protein-Coupled Chemoattractant-1, the rat orthologue of ChemerinR/Dezb/CMKRL1.

FIG. 5 shows the structural similarities between the amino acid sequences of ChemerinR/Dezb/CMKRL1 and the sequences of AT2, C3a, c5a, and fMLP receptors and selected chemokine receptor sequences performed using the ClustalX algorithm. The dendrogram shown was constructed using the TreeView Algorithm.

FIG. 6 shows the nucleotide (SEQ ID NO: 7) and deduced amino acid (SEQ ID NO: 8) sequences of human Preprochemerin.

FIG. 7 shows the nucleotide (SEQ ID NO: 9) and deduced amino acid (SEQ ID NO: 10) sequences of mouse Preprochemerin.

FIG. 8 shows the nucleotide (SEQ ID NO: 11) and deduced amino acid (SEQ ID NO: 12) sequences of human Prochemerin.

FIG. 9 shows the nucleotide (SEQ ID NO: 13) and deduced amino acid (SEQ ID NO: 14) sequences of human Chemerin.

FIG. 10 shows an alignment of the human and mouse Preprochemerin amino acid sequences. Identical amino acids are conservative substitutions are boxed.

FIG. 11 shows an alignment of human, mouse, rat, sus, bos and *Gallus* Preprochemerin sequences. The figure provides the percent amino acid identity across any two species listed.

FIG. 12 shows a partial chromatogram of the fifth step of purification of Chemerin from ascitic fluid. The active fractions (eluted with approximately 28% $CH_3CN$) of the previous step were diluted 6 fold with 0.1% TFA in $H_2O$ and directly loaded onto a C18 reverse phase column (1 mm×50 mm, Vydac) pre-equilibrated with 5% $CH_3CN$/0.1% TFA in $H_2O$ at a flow-rate of 0.1 ml/min. at room temperature. A 5-95% gradient of $CH_3CN$ in 0.1% TFA was applied with a 0.3%/min slope between 25 and 45%. The activity was eluted at 40% $CH_3CN$ (indicated by the black horizontal line).

FIG. 13 shows the identification of a specific response for ChemerinR following screening of HPLC fractions obtained from the fractionation of human ovary ascites. The different fractions obtained following fractionation of human ovary ascites were diluted fivefold in the assay buffer and tested in an aequorin assay using a cell line expressing ChemerinR (open circles) or cell lines expressing unrelated receptors (closed triangles and squares). The response obtained for each fraction was normalized using the ATP response of each cell line.

FIG. 14 shows the activation of ChemerinR by conditioned medium of 293T cells transiently transfected with Chemerin. 293T cells were transiently transfected with pcDNA3-Preprochemerin (TIG 2) or with pcDNA3 alone (mock transfected). Increasing volumes of the supernatant collected 4 days after transfection were analyzed using a Microlumat in an aequorin-based assay with CHO cells expressing ChemerinR. The assay was performed in triplicate, and SD is indicated. A representative experiment is shown.

FIG. 15 shows the characterization of antibodies directed against ChemerinR by flow cytometry.

FIG. 16 shows the polypeptide (SEQ ID NO: 73) and polynucleotide (SEQ ID NO: 72) of the truncated human Preprochemerin.

FIG. 20a shows the human polypeptides C-terminaltt extended or truncated from human chemerin-19 peptide.

FIG. 20b shows the mouse Chemerin polypeptides.

FIG. 21 shows the isolation of human Chemerin from human inflammatory fluid. A, First step HPLC fractionation (Poros column) of human ascetic fluid. The absorbance (AU) and biological activity on ChemR23 (luminescence in an aequorin-based assay, normalized to the ATP response, black bars) are shown. B, Third step (cation-exchange column). C, Fourth step (C18 column). D, Last step purification of the active compound (C18 column). The X axis is zoomed to focus on the region of interest.

FIGS. 22 A and B show fractions and sequences of major peaks from mass spectrometer spectrum. FIG. 22C shows Chemerin polypeptide sequence alignment. A, Monoisotopic peptide mass fingerprinting of the active fraction on a Maldi Q-TOF mass spectrometer following trypsin digestion. B, Sequences corresponding to selected major peaks of the Maldi Q-TOF mass spectrometer spectrum following trypsin digestion. Peptides 1-7 correspond to tryptic peptides derived from the TIG-2 gene product (prochemerin), while peptide 8 is not tryptic and corresponds to the C-terminal end of the purified protein. The position of the peptides within this sequence is given. The sequence of peptides in peaks 3, 5, 7 and 8 was confirmed by microsequencing. C, Amino acid sequence alignment of human (SEQ ID NO: 8) and mouse (accession number: AK002298, SEQ ID NO: 10) preprochemerin, and human cathelicidin FALL39 (SEQ ID NO: 51) precursor. Amino acid identities as compared to human preprochemerin are boxed. The signal peptides (predicted for mouse preprochemerin) are in bold lowercase characters, cysteines are in bold. Cleaved C-terminal peptides are in bold italics and underlined (predicted by analogy for mouse prochemerin). The location of introns (that interrupt the gene coding sequences between codons) are indicated by arrowheads.

FIG. 23 A shows SDS/PAGE of humanrecombinant Chemerin, expressed in CHO-K1 cells and purified by HPLC. The gel was silver stained and the major band corresponds to a protein of 18 kDa.Mass spectrometry analysis demonstrated the cleavage of the six C-terminal amino acids in this biologically active protein. FIGS. 23 B-F show the functional assays of human recombinant Chemerin. A, SDS/PAGE of human recombinant Chemerin, expressed in CHO-K1 cells and purified by HPLC. The gel was silver stained and the major band corresponds to a protein of 18 kDa.Mass spectrometry analysis demonstrated the cleavage of the six C-terminal amino acids in this biologically active protein. B, Biological Figure activity on ChemerinR of human recombinant Chemerin (filled circles) and prochemerin (open circles), using the aequorin assay. C, Competition binding assay using as tracer an iodinated peptide derived from the Chemerin C-terminus. Competition was performed with the unlabeled peptide (open squares) or human recombinant Chemerin (filled circles). D, Concentration-action curve of human Chemerin in a $GTP\gamma[_{35}S]$-binding assay, using membranes of CHO/ChemerinR cells. E, Immunodetection of phosphorylated ERK1/2 in CHO/ChemerinR cells, following stimulation by human recombinant Chemerin for 2 min. F, Kinetics of ERK1/ERK2 activation following stimulation by 10 nM human Chemerin. Each experiment was repeated at least three times.

FIGS. 24 A-F show expression and tissue distribution of human Chemerin and its receptor. A, Conversion of human recombinant prochemerin (100 nM) in conditioned medium from hamster CHO-K1 cells. Conversion rate was estimated by comparing the biological activity with that of the same molar amount of purified processed Chemerin. B and C, Transcripts encoding human ChemerinR (B) and prochemerin (C) were amplified by quantitative RT-PCR in a set of human tissues and cell populations. PBMC: peripheral blood mononuclear cells, iDC: immature dendritic cells. D and E, The expression of ChemerinR was analyzed by FACS in immature (solid line) and mature dendritic cells (gray area), following stimulation by LPS (D) or CD40L (E), using the 1H2 monoclonal antibody (IgG2A). Control labeling (dotted line) was made with an antibody of the same isotype. F, ChemerinR expression on macrophages was monitored using the 1H2 (thick solid line) and 4C7 (thin solid line) monoclonal antibodies. Control labeling (dotted line) was made with an antibody of the same isotype.

FIG. 25A-D show the biological activity of truncated Chemerin peptides as in aequorin assay. A, The biological activity of human recombinant prochemerin, human recombinant processed Chemerin, a 25 amino-acid C-terminal peptide of prochemerin, the corresponding 19 amino-acid C-terminal peptide of processed Chemerin, on human ChemR23 expressed in a CHO-K1 cell line, using the aequorin-based intracellular $Ca^{2+}$ release assay (aequorin assay). B, Biological activity of peptides C-terminally extended or truncated as compared to the C-terminus of processed Chemerin. (human Chemerin-19) on human ChemR23 expressed in a CHO-K1 cell line, using the aequorin-based intracellular $Ca^{2+}$ release assay (aequorin assay). C, Biological activity of peptides N-terminally truncated as compared to human Chemerin-19 on human ChemR23 expressed in a CHO-K1 cell line, using the aequorin-based intracellular $Ca^{2+}$ release assay (aequorin assay). D, Biological activity of peptides representing an ala-scan of the shorter C-terminal peptide (Chemerin-9) displaying an almost full activity on human ChemR23 expressed in a CHO-K1 cell line, using the aequorin-based intracellular $Ca^{2+}$ release assay (aequorin assay).

FIGS. 26A-H show the biological activity of Chemerin ex vivo on primary cells. A, Inhibition of the functional response of CHO-K1 cells expressing the ChemerinR (aequorin assay) by the 4C7 anti-ChemerinR monoclonal antibody. The cells were preincubated for 30 min at room temperature with various amounts of the 4C7 antibody before stimulation by 10 nM recombinant Chemerin. The data were normalized according to the response in the absence of antibody (100%) and in the absence of agonist (0%). B, Chemotaxis of human immature dendritic cells by recombinant Chemerin. Results are expressed as the mean±s.d. (n=3), and are representative of three donors. C, Chemerin-induced (10 pM) dendritic cell migration was inhibited by pertussis toxin (3 µg/ml) pretreatment of the cells, as well as by preincubation of the cells with the 4C7 monoclonal antibody (10 µg/ml). Checkerboard analysis investigates chemotactic versus chemokinetic effects of Chemerin on dendritic cells. Human Chemerin (10 pM) was added to the lower and/or upper chamber of the chemotaxis device. The chemokine RANTES (10 nM) was used as a positive control in the experiments. D, $Ca_{2+}$ flux in monocyte-derived dendritic cells in response to recombinant Chemerin (30 nM, arrow). E, The same experiment after 30 min preincubation of the cells with the 4C7 monoclonal antibody (10 µg/ml). F, Chemerin-induced macrophage migration (10 and 100 pM) and its inhibition by Pertussis toxin (3 µg/ml) pretreatment and 4C7 monoclonal antibody (10 µg/ml). Checkerboard analysis investigates chemotactic versus chemokinetic effects of Chemerin on macrophages. G, $Ca_{2+}$ flux in macrophages in response to recombinant Chemerin (30 nM, arrow). H, The same experiment after 30 min preincubation of the cells with the 4C7 monoclonal antibody (10 µg/ml).

FIG. 27 shows the anti-tumor activity of mouse Chemerin in vivo. A-C, Estimation of the proportion of cell population in G1, G2 and S phase following BrdU incorporation and propidium iodide staining. FACS analysis of control (A) and prochemerin-expressing B16/F0 (B) cells, and percentage of cells in S phase (C). D, Estimation size of tumors in mice, following the graft of B16/F0 cells expressing (filled circles) or not (open squares) mouse Chemerin. The data represent the mean±s.e.m. for n=11 in each group, and are representative of three experiments performed independently with similar results.:p<0.05,*: p<0.01, unpaired non parametric Mann-Whitney test. E and F, Hematoxylineosin staining of cryosections through control (E) and prochemerin-expressing (F) tumors, 18 days after the graft.

DETAILED DESCRIPTION OF THE INVENTION

Figure 17:
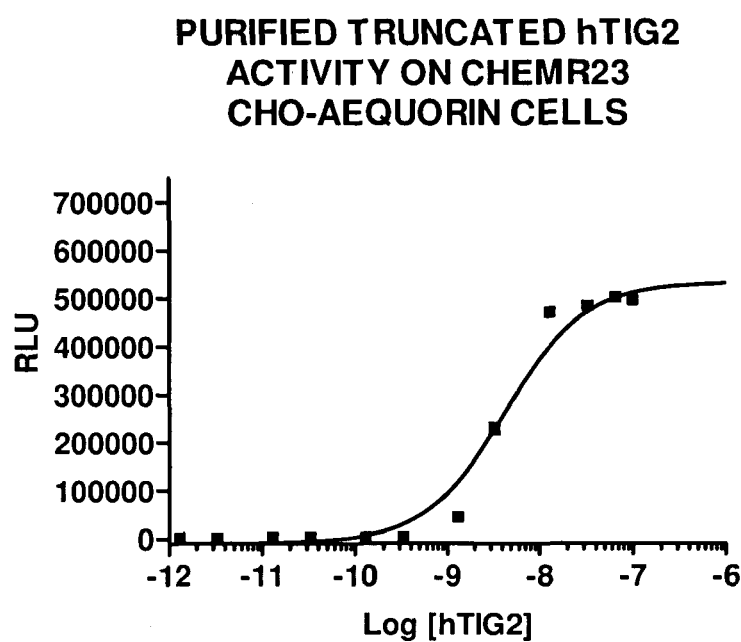
FIG. 17 shows the $EC_{50}$ for activation of ChemerinR by truncated human Preprochemerin (truncated hTIG2).

The invention relates to the discovery that Chemerin polypeptide is a natural ligand for ChemerinR and that the interaction between Chemerin and ChemerinR induces antidisease immuno-responses. The interaction is useful for screening assays for agents that modulate the interaction and thus the function of ChemerinR. The interaction between Chemerin and ChemerinR also provides for the diagnosis of conditions involving dysregulated receptor activity. The interaction also provides for therapeutic approaches for treatment of a disease or disorder.

Definitions

For convenience, the meaning of certain terms and phrases used in the specification, examples, and appended claims, are provided below.

The term "polypeptide" refers to a polymer in which the monomers are amino acids and are joined together through peptide or disulfide bonds. It also refers to either a full-length naturally-occurring amino acid sequence or a fragment thereof between about 8 and about 500 amino acids in length. Additionally, unnatural amino acids, for example, β-alanine, phenyl glycine and homoarginine may be included. Commonly-encountered amino acids which are not gene-encoded may also be used in the present invention. All of the amino acids used in the present invention may be either the D- or L-optical isomer. The L-isomers are preferred.

As used herein, the term "ChemerinR polypeptide" refers to a polypeptide having two essential properties: 1) a ChemerinR polypeptide has at least 70% amino acid identity, and preferably 80%, 90%, 95% or higher, including 100% amino acid identity, to SEQ ID NO: 2; and 2) a ChemerinR polypeptide has ChemerinR activity, i.e., the polypeptide binds a Chemerin polypeptide or a functional fragment thereof. Optimally, a "ChemerinR polypeptide" also has ChemerinR signaling activity as defined herein.

The term "a Chemerin polypeptide" refers to a polypeptide having at least 31% or higher identity to either SEQ ID NO: 14 or SEQ ID NO: 73, and the defined polypeptide specifically binds to and activates a signaling activity of a ChemerinR polypeptide. Preferably, the polypeptide is at least 50%, or higher identity to either SEQ ID NO: 14 or SEQ ID NO: 73. Preferably, the polypeptide is at least 60%, or 70%, or 80%, or 85%, or higher identity to either SEQ ID NO: 14 or SEQ ID NO: 73. The term "specifically binds" means that the Chemerin polypeptide has an $EC_{50}$, $IC_{50}$, or a $K_d$ of 100 nM or less. "Chemerin polypeptide" also refers to a fragment of a polypeptide meeting the preceding definition, wherein the fragment retains at least 50% of the binding activity and level of signaling activation of the full length polypeptide of SEQ ID NO: 14. A Chemerin also includes a analog, variant or some short polypeptide from C-terminal end of the Chemerin (SEQ ID NO 14) as depicted in FIGS. 8, and 16, 20a and 20b that binds specifically to a ChemerinR polypeptide. A Chemerin polypeptide can comprise additions, insertions, deletions or substitutions relative to SEQ ID NO: 14, as long as the resulting polypeptide retains at least 50% of the binding activity and level of signaling activation of the full length polypeptide represented by SEQ ID NO: 14. In one embodiment, a "Chemerin polypeptide" encompasses further the truncated Preprochemerin sequence of SEQ ID NO: 73 shown in FIG. 16 (the nucleotide sequence shown in FIG. 16, which encodes the truncated Preprochemerin polypeptide is SEQ ID NO: 72). In addition to the sequences necessary for binding to ChemerinR and activating a ChemerinR signaling activity, a Chemerin polypeptide, including the truncated Chemerin polypeptide can comprise additional sequences, as in for example, a Chemerin fusion protein. Non-limiting examples of fusion partners include glutathione-S-transferase (GST), maltose binding protein, alkaline phosphatase, thioredoxin, green fluorescent protein (GFP), histidine tags (e.g., 6× or greater His), or epitope tags (e.g., Myc tag, FLAG tag).

The term "a nucleic acid sequence" refers to a polynucleotides such DNA or RNA. The term should also include both single and doublestranded polynucleotides. The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

As used herein, the term "Chemerin polynucleotide" refers to a polynucleotide that encodes a Chemerin polypeptide as defined herein, or the complement thereof. In one embodiment, a "Chemerin polynucleotide" is a polynucleotide sequence which encodes a truncated Preprochemerin polypeptide (e.g., the truncated Preprochemerin polypeptide shown in FIG. 17), such as the polynucleotide sequence shown in FIG. 17 (SEQ ID NO: 49).

As used herein, the term "a ChemerinR polynucleotide" refers to a polynucleotide that encodes a ChemerinR polypeptide, or a ChemerinR polypeptide analog or variant as defined herein.

As used herein, the term "standard" refers to a sample taken from an individual who is not affected by a disease or disorder characterized by dysregulation of G-protein coupled receptor (i.e., ChemerinR) activity. The "standard" is used as a reference for the comparison of receptor mRNA or polypeptide levels and quality (i.e., mutant vs. wild type), as well as for the comparison of G-protein coupled receptor activities. A "standard" also encompasses a reference sequence, e.g., SEQ ID NO: 1, with which sequences of nucleic acids or their encoded polypeptides are compared.

As used herein, the term "dysregulation" refers to the signaling activity of ChemerinR in a sample wherein a) a 10% or greater increase or decrease in the amount of one or more of ChemerinR polypeptide, ligand or mRNA level is measured relative to a standard, as defined herein, in a given assay or; b) at least a single base pair change in the ChemerinR coding sequence is detected relative to SEQ ID NO: 1, and results in an alteration of ChemerinR ligand binding or signaling activity as defined in paragraphs a), c) or d) or; c) a 10% or greater increase or decrease in the amount of ChemerinR ligand binding activity is measured relative to a standard, as defined herein, in a given assay or; d) a 10% or greater increase or decrease in a second messenger, as defined herein, is measured relative to the standard, as defined herein, in a given assay.

The term "expression vector" refers to a nucleic acid construct capable of directing the expression of genes to which they are linked. The construct further includes regulatory sequences, including for example, a promoter, operably linked to the genes. In general, expressing vectors of utility in recombinant DNA techniques are often in the form of "plasmids" which refer generally to circular double stranded DNA loops which, in their vector form are not bound to chromosome.

The term "plasmid DNA expression vector" refers generally to a circular double stranded DNA loop which in their vector form are not bound to the chromosome, and which are capable of autonomous replication and/or expression of nucleic acids to which it is linked.

The term "adenovirus expression vector" refers to an expression vector which is derived from human adenovirus serotype 5, lacks ability to self-replicate, is capable of delivering into a cell a gene, and is capable of autonomous replication and/or expression of the gene inside the cell.

The term "composition" refers to a compound that is made of one or more molecules, preferably a protein or a nucleic acid encoding a protein, or a mixture thereof. A composition can be naturally occurring, or derived by recombinant technology, or by other synthetic means known to one skill in the art.

The term "therapeutic composition" refers to a composition that upon delivered into a cell, acts upon the cell to correct or compensate for an underlying molecular deficit, or counteract a disease state or syndrome of the cell.

The term "antibody" refers to the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In preferred embodiments, the antibodies, the antibody further comprises a label attached thereto and able to be detected, (e.g., the label can be a radioisotope, fluorescent compound, chemiluminescent compound, enzyme, or enzyme co-factor).

The term "monoclonal antibody" refers to an antibody that recognizes only one type of antigen. This type of antibodies is produced by the daughter cells of a single antibody-producing hybridoma.

The term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and anti-sense techniques.

The term "therapeutically effective amount" refers to the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that results in the therapeutic effect, whether administered in combination, serially or simultaneously. Generally, a composition will be administered in a single dosage in the range of 100 µg-100 mg/kg body weight, preferably in the range of 1 µg-100 µg/kg body weight. This dosage may be repeated daily, weekly, monthly, yearly, or as considered appropriate by the treating physician.

As used herein, the term "ChemerinR activity" refers to specific binding of a Chemerin polypeptide or a functional fragment thereof by a ChemerinR polypeptide.

As used herein, the term "ChemerinR signaling activity" refers to the initiation or propagation of signaling by a ChemerinR polypeptide. ChemerinR signaling activity is monitored by measuring a detectable step in a signaling cascade by assaying one or more of the following: stimulation of GDP for GTP exchange on a G protein; alteration of adenylate cyclase activity; protein kinase C modulation; phosphatidylinositol breakdown (generating second messengers diacylglycerol, and inositol triphosphate); intracellular calcium flux; activation of MAP kinases; modulation of tyrosine kinases; or modulation of gene or reporter gene activity. A detectable step in a signaling cascade is considered initiated or mediated if the measurable activity is altered by 10% or more above or below a baseline established in the substantial absence of a Chemerin polypeptide relative to any of the ChemerinR activity assays described herein below. The measurable activity can be measured directly, as in, for example, measurement of cAMP or diacylglycerol levels. Alternatively, the measurable activity can be measured indirectly, as in, for example, a reporter gene assay.

As used herein, the term "detectable step" refers to a step that can be measured, either directly, e.g., by measurement of a second messenger or detection of a modified (e.g., phosphorylated) protein, or indirectly, e.g., by monitoring a downstream effect of that step. For example, adenylate cyclase activation results in the generation of cAMP. The activity of adenylate cyclase can be measured directly, e.g., by an assay that monitors the production of cAMP in the assay, or indirectly, by measurement of actual levels of cAMP.

As used herein, the term "isolated" refers to a population of molecules, e.g., polypeptides or polynucleotides, the composition of which is less than 50% (by weight), preferably less than 40% and most preferably 2% or less, contaminating molecules of an unlike nature. When the term "isolated" is applied to a ChemerinR polypeptide, it is specifically meant to encompass a ChemerinR polypeptide that is associated with or embedded in a lipid membrane.

As used herein, the terms "candidate compound" and "candidate modulator" refer to a composition being evaluated for the ability to modulate ligand binding to a ChemerinR polypeptide or the ability to modulate an activity of a ChemerinR polypeptide. Candidate modulators can be natural or synthetic compounds, including, for example, small molecules, compounds contained in extracts of animal, plant, bacterial or fungal cells, as well as conditioned medium from such cells.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises carbon.

As used herein, the term "change in binding" or "change in activity" and the equivalent terms "difference in binding" or "difference in activity" refer to an at least 10% increase or decrease in binding, or signaling activity in a given assay.

As used herein, the term "conditions permitting the binding of Chemerin to ChemerinR" refers to conditions of, for example, temperature, salt concentration, pH and protein concentration under which Chemerin binds ChemerinR. Exact binding conditions will vary depending upon the nature of the assay, for example, whether the assay uses viable cells or only membrane fraction of cells. However, because ChemerinR is a cell surface protein, and because Chemerin is a secreted polypeptide that interacts with ChemerinR on the cell surface, favored conditions will generally include physiological salt (90 mM) and pH (about 7.0 to 8.0). Temperatures for binding can vary from 15° C. to 37° C., but will preferably be between room temperature and about 30° C. The concentration of Chemerin and ChemerinR polypeptide in a binding reaction will also vary, but will preferably be about 0.1 pM (e.g., in a reaction with radiolabeled tracer Chemerin, where the concentration is generally below the $K_d$) to 1 µM (e.g., Chemerin as competitor). As an example, for a binding assay using ChemerinR-expressing cells and purified, recombinant, labeled Chemerin polypeptide, binding is performed using 0.1 nM labeled Chemerin, 100 nM cold Chemerin, and 25,000 cells at 27° C. in 250 µl of a binding buffer consisting of 50 mM HEPES (pH 7.4), 1 mM $CaCl_2$, and 0.5% Fatty acid free BSA.

As used herein, the term "sample" refers to the source of molecules being tested for the presence of an agent that modulates binding to or signaling activity of a ChemerinR polypeptide. A sample can be an environmental sample, a natural extract of animal, plant yeast or bacterial cells or tissues, a clinical sample, a synthetic sample, or a conditioned medium from recombinant cells or a fermentation process. The term "tissue sample" refers to a tissue that is tested for the presence, abundance, quality or an activity of a ChemerinR polypeptide, a Chemerin polypeptide, a nucleic acid encoding a ChemerinR or Chemerin polypeptide, or an agent that modifies the ligand binding or activity of a ChemerinR polypeptide.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a ChemerinR polypeptide. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the term "decrease in binding" refers to a decrease of at least 10% in the binding of a Chemerin polypeptide or other agonist to a ChemerinR polypeptide as measured in a binding assay as described herein.

As used herein, the term "second messenger" refers to a molecule, generated or caused to vary in concentration by the activation of a G-Protein Coupled Receptor, that participates in the transduction of a signal from that GPCR. Non-limiting examples of second messengers include cAMP, diacylglycerol, inositol triphosphates and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCr activity that measures intracellular calcium flux induced by activated GPCRs, wherein intracellular calcium flux is measured by the luminescence of aequorin expressed in the cell.

As used herein, the term "binding" refers to the physical association of a ligand (e.g., a Chemerin polypeptide) with a receptor (e.g., ChemerinR). As the term is used herein, binding is "specific" if it occurs with an $EC_{50}$ or a $K_d$ of 100 nM or less, generally in the range of 100 nM to 10 pM. For example, binding is specific if the $EC_{50}$ or $K_d$ is 100 nM, 50 nM, 10 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 75 pM, 50 pM, 25 pM or 10 pM or less.

As used herein, the term "$EC_{50}$," refers to that concentration of an agent at which a given activity, including binding of a Chemerin polypeptide or other ligand and a functional activity of a ChemerinR polypeptide, is 50% of the maximum for that ChemerinR activity measurable using the same assay. Stated differently, the "$EC_{50}$" is the concentration of agent that gives 50% activation, when 100% activation is set at the amount of activity that does not increase with the addition of more agonist. It should be noted that the "$EC_{50}$ of a Chemerin polypeptide" will vary with the identity of the Chemerin polypeptide; for example, variant Chemerin polypeptides (i.e., those containing insertions, deletions, substitutions or fusions with other polypeptides, including Chemerin molecules from species other than humans and variants of them that satisfy the definition of Chemerin polypeptide set forth above) can have $EC_{50}$ values higher than, lower than or the same as wild-type Chemerin. Therefore, where a Chemerin variant sequence differs from wild-type Chemerin of SEQ ID NO:8, one of the skill in the art can determine the $EC_{50}$ for that variant according to conventional methods. The $EC_{50}$ of a given Chemerin polypeptide is measured by performing an assay for an activity of a fixed amount of ChemerinR polypeptide in the presence of doses of the Chemerin polypeptide that increase at least until the ChemerinR response is saturated or maximal, and then plotting the measured ChemerinR activity versus the concentration of Chemerin polypeptide.

As used herein, the term "$IC_{50}$" is the concentration of an antagonist or inverse agonist that reduces the maximal activation of a ChemerinR receptor by 50%.

As used herein, the term "detectably labeled" refers to the property of a molecule, e.g., a Chemerin polypeptide or other ChemerinR ligand, that has a structural modification that incorporates a functional group (label) that can be readily detected. Detectable labels include but are not limited to fluorescent compounds, isotopic compounds, chemiluminescent compounds, quantum dot labels, biotin, enzymes, electron-dense reagents, and haptens or proteins for which antisera or monoclonal antibodies are available. The various means of detection include but are not limited to spectroscopic, photochemical, radiochemical, biochemical, immunochemical, or chemical means.

As used herein, the term "affinity tag" refers to a label, attached to a molecule of interest (e.g., a Chemerin polypeptide or other ChemerinR ligand), that confers upon the labeled molecule the ability to be specifically bound by a reagent that binds the label. Affinity tags include, but are not limited to an epitope for an antibody (known as "epitope tags"), biotin, 6× His, and GST. Affinity tags can be used for the detection, as well as for the purification of the labeled species.

As used herein, the term "decrease in binding" refers to a decrease of at least 10% in the amount of binding detected in a given assay with a known or suspected modulator of ChemerinR relative to binding detected in an assay lacking that known or suspected modulator.

As used herein, the term "delivering," when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "effective amount" refers to that amount of a drug or ChemerinR modulating agent that results in a change in a ChemerinR activity as defined herein (i.e., at least 10% increase or decrease in a ChemerinR activity).

As used herein, the term "amplifying," when applied to a nucleic acid sequence, refers to a process whereby one or more copies of a nucleic acid sequence is generated from a template nucleic acid. A preferred method of "amplifying" is PCR or RT/PCR.

As used herein, the term "substantial absence" refers to a level of an activating or inhibiting factor that is below the level necessary to activate or inhibit GPCR function by at least 10% as measured by a given assay disclosed herein or known in the art.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. ChemerinR is a GPCR.

As used herein, the term "agent that modulates the function of a ChemerinR polypeptide" is a molecule or compound that increases or decreases ChemerinR activity, including compounds that change the binding of Chemerin polypeptides or other agonists, and compounds that change ChemerinR downstream signaling activities.

As used herein, the term "null mutation" refers to an insertion, deletion, or substitution that modifies the chromosomal sequences encoding a polypeptide, such that the polypeptide is not expressed.

I. Assays for the Identification of Agents that Modulate the Activity of ChemerinR Agents that modulate the activity of ChemerinR can be identified in a number of ways that take advantage of the interaction of the receptor with Chemerin. For example, the ability to reconstitute ChemerinR/Chemerin binding either in vitro, on cultured cells or in vivo provides a target for the identification of agents that disrupt that binding. Assays based on disruption of binding can identify agents, such as small organic molecules, from libraries or collections of such molecules. Alternatively, such assays can identify agents in samples or extracts from natural sources, e.g., plant, fungal or bacterial extracts or even in human tissue samples (e.g., tumor tissue). In one aspect, the extracts can be made from cells expressing a library of variant nucleic acids, peptides or polypeptides, including, for example, variants of Chemerin polypeptide itself. Modulators of ChemerinR/Chemerin binding can then be screened using a binding assay or a functional assay that measures downstream signaling through the receptor. Both binding assays and functional assays are validated using Chemerin polypeptide.

Another approach that uses the ChemerinR/Chemerin interaction more directly to identify agents that modulate ChemerinR function measures changes in ChemerinR downstream signaling induced by candidate agents or candidate modulators. These functional assays can be performed in isolated cell membrane fractions or on cells expressing the receptor on their surfaces.

A. ChemerinR Polypeptides.

Assays using the interaction of ChemerinR and Chemerin require a source of ChemerinR polypeptide. The polynucleotide and polypeptide sequence of human ChemerinR are presented herein as SEQ ID NOs: 1 and 2. The human ChemerinR polynucleotide sequence is also available at GenBank Accession No. Y14838, and was reported in Samson et al., 1998, Eur. J. Immunol. 28: 1689-1700, incorporated herein by reference. ChemerinR polypeptide sequence is also recorded at accession Nos. 075748 and CAA75112 in the Swissprot database. Related sequences include those for CMKRL1 (GenBank Accession Nos. XM_006864 and NM004072 (nucleotide sequences) and Swissprot Accession No. Q99788 (polypeptide sequence)), human DEZb (GenBank Accession No. U79527 (nucleotide sequence)), human DEZa (GenBank Accession No. U79526 (nucleotide sequence), mouse DEZ (GenBank Accession No. U79525 (nucleotide sequence) and Swissprot Accession No. P97468 (polypeptide sequence)), and rat ChemerinR (GenBank Accession No. AJ002745 (nucleotide sequence) and Swissprot Accession No. 035786 (polypeptide sequence).

One skilled in the art can readily amplify a ChemerinR sequence from a sample containing mRNA encoding the protein through basic PCR and molecular cloning techniques using primers or probes designed from the known sequences.

The expression of recombinant polypeptides is well known in the art. Those skilled in the art can readily select vectors and expression control sequences for the expression of ChemerinR polypeptides useful according to the invention in eukaryotic or prokaryotic cells. ChemerinR must be associated with cell membrane or detergents like synthetic liposomes in order to have binding or signaling function. Methods for the preparation of cellular membrane fractions are well known in the art, e.g., the method reported by Hubbard & Cohn, 1975, J. Cell Biol. 64: 461-479, which is incorporated herein by reference. In order to produce membranes comprising ChemerinR, one need only apply such techniques to cells endogenously or recombinantly expressing ChemerinR. Alternatively, membrane-free ChemerinR can be integrated into membrane preparations by dilution of detergent solution of the polypeptide (see, e.g., Salamon et al., 1996, Biophys. J. 71:283-294, which is incorporated herein by reference).

B. Chemerin Polypeptides.

The present invention relates to a Chemerin polypeptide including the full-length active form and the truncated Chemerin polypeptides. The 163 amino acid full-length Preprochemerin polypeptide is first produced in a cell as inactive form (FIG. 6). This inactive form of Chemerin is converted into the active form of Chemerin (137 amino acids) by the following two steps: a) removing 20 amino acids at N-terminus (this form is called prochemerin, 143 amino acids, Fibure 8); b) removing 6 amino acids at C-terminus (137 amino acids, FIG. 9). Preferably, the C-terminus human truncated Preprochemerin and chemerin polypeptides are presented in FIGS. 16, 8 and 20a (human chemerin-9, -10, -11, -12, -13, -19) respectively. The Chemerin polypeptides of the invention may be a recombinant Chemerin polypeptide, a natural Chemerin polypeptide, or a synthetic Chemerin polypeptide, preferably a recombinant Chemerin polypeptide. The Chemerin polypeptide of the invention may also encompass the analogs or variants whose polypeptide sequences are different from the naturally-occurring ones, but retain substantially the same function or activity as a Chemerin polypeptide.

The full-length human inactive Preprochemerin polynucleotide and polypeptide sequences are presented herein as SEQ ID Nos 7 and 8, respectively (FIG. 6). Preprochemerin sequences are also available from GenBank (e.g., Human polynucleotide sequences include Accession Nos. XM 004765, U77594, NM 002889, human polypeptide sequence is available at Accession Nos. Q99969, BAA76499, AAB47975, NP002880, and XP004765; Gallus gallus polynucleotide sequences include Accession Nos. BG713704, BG713660 and BG713614; mouse polynucleotide sequences include BF020273, AW113641 and bf018000; rat polynucleotide sequences include AW915104; Sus scrofa polynucleotide sequences include BF078978 and BF713092 (overlapping ESTs, last 7 amino acids of Preprochemerin sequence in BF713092); and Bos taurus polynucleotide sequences include BG691132). An alignment of Preprochemerin sequences is presented in FIG. 11.

The present invention also relates to a nucleic acid sequence that encodes a Chemerin polypeptide. The nucleic acid sequences of the invention may also contain the coding sequences fused in frame to a marker sequence for purification of the polypeptides of the present invention. The nucleic acid sequences of the present invention may be employed for producing polypeptides of the present invention by recombinant techniques. The nucleic acid sequences of the invention may be included in any one of the expressing vectors such as plasmid DNA, phage DNA, or Viral DNA vectors etc, all vectors are well known in the art.

As with ChemerinR, Chemerin polynucleotides can be cloned through standard PCR and molecular cloning techniques using the known sequences as a source of amplification primers or probes. Similarly, cloned Chemerin polypeptides can be expressed in eukaryotic or prokaryotic cells as known in the art. As a non-limiting example, Chemerin may be cloned into an acceptable mammalian expression vector, such as pcDNA3 (Invitrogen) for expression in a host cell. A Chemerin expression construct for expression in yeast is described in Example 4.

Chemerin can also be expressed in vitro through in vitro transcription and translation. Further, if desired for a given assay or technique, Chemerin polypeptides useful according to the invention can be produced as fusion proteins or tagged proteins. For example, either full length Chemerin or a portion thereof (i.e., at least 10 amino acids, preferably at least 20 amino acids or more, up to one amino acid less than full length Chemerin) can be fused to Glutathione-S-Transferase (GST), secreted alkaline phosphatase (SEAP), a FLAG tag, a Myc tag, or a 6×-His peptide to facilitate the purification or detection of the Chemerin polypeptide. Methods and vectors for the production of tagged or fusion proteins are well known in the art, as are methods of isolating and detecting such fused or tagged proteins.

Recombinant Chemerin polypeptides can be used in purified form. Alternatively, conditioned medium from Chemerin transfected cells can be used. The amounts of Chemerin necessary in a given binding or functional assay according to the invention will vary depending upon the assay, but will generally use 1 pM to 1 nM of labeled and 10 pM to 1 µM of unlabeled Chemerin per assay. The affinities and $EC_{50}$s of tagged Chemerin polypeptides for ChemerinR may vary relative to those of full length wild type Chemerin polypeptide, and the amount necessary for a given assay can therefore be adjusted relative to the wild-type values. If necessary for a given assay, Chemerin can be labeled by incorporation of radiolabeled amino acids in the medium during synthesis, e.g., $^{35}$S-Met, $^{14}$C-Leu, tritium H3 or others as appropriate. Methods of chemical labeling with $^{125}$I are known in the art. Fluorescent labels can also be attached to Chemerin polypeptides or to other ChemerinR ligands using standard labeling techniques.

The Chemerin polypeptides may also be employed for treatment of a disease or disorder. For example, cells from a patient may be engineered with a polynucleotide (DNA or RNA) encoding a polypeptide ex vivo, with the engineered cells then being provided to a patient to be treated with the polypeptide. Such methods are well-known in the art. Similarly, cells may be engineered in vivo for expression of a polypeptide in vivo by, for example, procedures known in the art. These and other methods for administering a polypeptide of the present invention by such method should be apparent to those skilled in the art from the teachings of the present invention. For example, the expression vector for engineering cells in vivo may be a retrovirus, an adenovirus, or a non-viral vectors.

C. Assays to Identify Modulators of ChemerinR Activity

The discovery that Chemerin is a ligand of the ChemerinR receptor permits screening assays to identify agonists, antagonists and inverse agonists of receptor activity. The screening assays will have two general approaches.

1) Ligand binding assays, in which cells expressing ChemerinR, membrane extracts from such cells, or immobilized lipid membranes comprising ChemerinR are exposed to a labeled Chemerin polypeptide and candidate compound. Following incubation, the reaction mixture is measured for specific binding of the labeled Chemerin polypeptide to the ChemerinR receptor. Compounds that interfere with or displace labeled Chemerin polypeptide can be agonists, antagonists or inverse agonists of ChemerinR activity. Functional analysis can be performed on positive compounds to determine which of these categories they fit.

2) Functional assays, in which a signaling activity of ChemerinR is measured.

a) For agonist screening, cells expressing ChemerinR or membranes prepared from them are incubated with candidate compound, and a signaling activity of ChemerinR is measured. The assays are validated using a Chemerin polypeptide as agonist, and the activity induced by compounds that modulate receptor activity is compared to that induced by Chemerin. An agonist or partial agonist will have a maximal biological activity corresponding to at least 10% of the maximal activity of wild type human Chemerin when the agonist or partial agonist is present at 10 µM or less, and preferably will have 50%, 75%, 100% or more, including 2-fold, 5-fold, 10-fold or more activity than wild-type human Chemerin.

b) For antagonist or inverse agonist screening, cells expressing ChemerinR or membranes isolated from them are assayed for signaling activity in the presence of a Chemerin polypeptide with or without a candidate compound. Antagonists or inverse agonists will reduce the level of Chemerin-stimulated receptor activity by at least 10%, relative to reactions lacking the antagonist or inverse agonist.

c) For inverse agonist screening, cells expressing constitutive ChemerinR activity or membranes isolated from them are used in a functional assay that measures an activity of the receptor in the presence and absence of a candidate compound. Inverse agonists are those compounds that reduce the constitutive activity of the receptor by at least 10%. Overexpression of ChemerinR (i.e., expression of 5-fold or higher excess of ChemerinR polypeptide relative to the level naturally expressed in macro phages in vivo) may lead to constitutive activation. ChememerinR can be overexpressed by placing it under the control of a strong constitutive promoter, e.g., the CMV early promoter. Alternatively, certain mutations of conserved GPCR amino acids or amino acid domains tend to lead to constitutive activity. See for example: Kjelsberg et al., 1992, *J. Biol. Chem.* 267:1430; McWhinney et al., 2000. *J. Biol. Chem.* 275:2087; Ren et al., 1993, *J. Biol. Chem.* 268:16483; Samama et al., 1993, *J. Biol. Chem.* 268: 4625; Parma et al., 1993, *Nature* 365:649; Parma et al., 1998, *J. Pharmacol. Exp. Ther.* 286:85; and Parent et al., 1996, *J. Biol. Chem.* 271:7949.

Ligand Binding and Displacement Assays:

One can use ChemerinR polypeptides expressed on a cell, or isolated membranes containing receptor polypeptides, along with a Chemerin polypeptide in order to screen for compounds that inhibit the binding of Chemerin to ChemerinR. When identified in an assay that measures binding or Chemerin polypeptide displacement alone, compounds will have to be subjected to functional testing to determine whether they act as agonists, antagonists or inverse agonists.

For displacement experiments, cells expressing a ChemerinR polypeptide (generally 25,000 cells per assay or 1 to 100 µg of membrane extracts) are incubated in binding buffer (e.g., 50 mM Hepes pH 7.4; 1 mM $CaCl_2$; 0.5% Bovine Serum Albumin (BSA) Fatty Acid-Free; and 0 5 mM $MgCl_2$) for 1.5 hrs (at, for example, 27° C.) with labeled Chemerin polypeptide in the presence or absence of increasing concentrations of a candidate modulator. To validate and calibrate the assay, control competition reactions using increasing concentrations of unlabeled Chemerin polypeptide can be performed. After incubation, cells are washed extensively, and bound, labeled Chemerin is measured as appropriate for the given label (e.g., scintillation counting, enzyme assay, fluorescence, etc.). A decrease of at least 10% in the amount of labeled Chemerin polypeptide bound in the presence of candidate modulator indicates displacement of binding by the candidate modulator. Candidate modulators are considered to bind specifically in this or other assays described herein if they displace 50% of labeled Chemerin (sub-saturating Chemerin dose) at a concentration of 10 µM or less (i.e., $EC_{50}$ is 10 µM or less).

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of a Chemerin polypeptide from the aqueous phase to a ChemerinR polypeptide immobilized in a membrane on the sensor. This change in mass is measured as resonance units versus time after injection or removal of the Chemerin polypeptide or candidate modulator and is measured using a Biacore Biosensor (Biacore AB). ChemerinR can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for Chemerin binding to ChemerinR in an SPR assay can be fine-tuned by one of skill in the art using the conditions reported by Sarrio et al. as a starting point.

SPR can assay for modulators of binding in at least two ways. First, a Chemerin polypeptide can be pre-bound to immobilized ChemerinR polypeptide, followed by injection of candidate modulator at approximately 10 μl/min flow rate and a concentration ranging from 1 nM to 100 μM, preferably about 1 μM. Displacement of the bound Chemerin can be quantitated, permitting detection of modulator binding. Alternatively, the membrane-bound ChemerinR polypeptide can be pre-incubated with candidate modulator and challenged with a Chemerin polypeptide. A difference in Chemerin binding to the ChemerinR exposed to modulator relative to that on a chip not pre-exposed to modulator will demonstrate binding. In either assay, a decrease of 10% or more in the amount of a Chemerin polypeptide bound is in the presence of candidate modulator, relative to the amount of a Chemerin polypeptide bound in the absence of candidate modulator indicates that the candidate modulator inhibits the interaction of ChemerinR and Chemerin.

Another method of measuring inhibition of binding of a Chemerin polypeptide to ChemerinR uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g., a Chemerin polypeptide and a ChemerinR polypeptide, are labeled with a complementary pair of donor and acceptor fluorophores. While bound closely together by the ChemerinR:Chemerin interaction, the fluorescence emitted upon excitation of the donor fluorophore will have a different wavelength than that emitted in response to that excitation wavelength when the polypeptides are not bound, providing for quantitation of bound versus unbound polypeptides by measurement of emission intensity at each wavelength. Donor:Acceptor pairs of fluorophores with which to label the polypeptides are well known in the art. Of particular interest are variants of the *A. victoria* GFP known as Cyan FP (CFP, Donor(D)) and Yellow FP (YFP, Acceptor (A)). The GFP variants can be made as fusion proteins with the respective members of the binding pair to serve as D-A pairs in a FRET scheme to measure protein-protein interaction. Vectors for the expression of GFP variants as fusions are known in the art. As an example, a CFP-Chemerin fusion and a YFP-ChemerinR fusion can be made. The addition of a candidate modulator to the mixture of labeled Chemerin and ChemerinR proteins will result in an inhibition of energy transfer evidenced by, for example, a decrease in YFP fluorescence relative to a sample without the candidate modulator. In an assay using FRET for the detection of ChemerinR: Chemerin interaction, a 10% or greater decrease in the intensity of fluorescent emission at the acceptor wavelength in samples containing a candidate modulator, relative to samples without the candidate modulator, indicates that the candidate modulator inhibits ChemerinR:Chemerin interaction.

A variation on FRET uses fluorescence quenching to monitor molecular interactions. One molecule in the interacting pair can be labeled with a fluorophore, and the other with a molecule that quenches the fluorescence of the fluorophore when brought into close apposition with it. A change in fluorescence upon excitation is indicative of a change in the association of the molecules tagged with the fluorophore: quencher pair. Generally, an increase in fluorescence of the labeled ChemerinR polypeptide is indicative that the Chemerin polypeptide bearing the quencher has been displaced. For quenching assays, a 10% or greater increase in the intensity of fluorescent emission in samples containing a candidate modulator, relative to samples without the candidate modulator, indicates that the candidate modulator inhibits ChemerinR:Chemerin interaction.

In addition to the surface plasmon resonance and FRET methods, fluorescence polarization measurement is useful to quantitate protein-protein binding. The fluorescence polarization value for a fluorescently-tagged molecule depends on the rotational correlation time or tumbling rate. Protein complexes, such as those formed by ChemerinR associating with a fluorescently labeled Chemerin polypeptide, have higher polarization values than uncomplexed, labeled Chemerin. The inclusion of a candidate inhibitor of the ChemerinR: Chemerin interaction results in a decrease in fluorescence polarization, relative to a mixture without the candidate inhibitor, if the candidate inhibitor disrupts or inhibits the interaction of ChemerinR with Chemerin. Fluorescence polarization is well suited for the identification of small molecules that disrupt the formation of polypeptide or protein complexes. A decrease of 10% or more in fluorescence polarization in samples containing a candidate modulator, relative to fluorescence polarization in a sample lacking the candidate modulator, indicates that the candidate modulator inhibits ChemerinR:Chemerin interaction.

Another alternative for monitoring ChemerinR:Chemerin interactions uses a biosensor assay. ICS biosensors have been described by AMBRI (Australian Membrane Biotechnology Research Institute; http//www.ambri.com.au/). In this technology, the association of macromolecules such as ChemerinR and Chemerin, is coupled to the closing of gramacidin-facilitated ion channels in suspended membrane bilayers and thus to a measurable change in the admittance (similar to impedence) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of ChemerinR and Chemerin.

It is important to note that in assays of protein-protein interaction, it is possible that a modulator of the interaction need not necessarily interact directly with the domain(s) of the proteins that physically interact. It is also possible that a modulator will interact at a location removed from the site of protein-protein interaction and cause, for example, a conformational change in the ChemerinR polypeptide. Modulators (inhibitors or agonists) that act in this manner are nonetheless of interest as agents to modulate the activity of ChemerinR.

It should be understood that any of the binding assays described herein can be performed with a non-Chemerin ligand (for example, agonist, antagonist, etc.) of ChemerinR, e.g., a small molecule identified as described herein. In practice, the use of a small molecule ligand or other non-Chemerin ligand has the benefit that non-polypeptide chemical compounds are generally cheaper and easier to produce in purified form than polypeptides such as Chemerin. Thus, a non-Chemerin ligand is better suited to high-throughput assays for the identification of agonists, antagonists or inverse agonists than full length Chemerin. This advantage in no way erodes the importance of assays using Chemerin, however, as such assays are well suited for the initial identification of non-Chemerin ligands.

Any of the binding assays described can be used to determine the presence of an agent in a sample, e.g., a tissue sample, that binds to the ChemerinR receptor molecule, or that affects the binding of Chemerin to the receptor. To do so, ChemerinR polypeptide is reacted with Chemerin polypeptide or another ligand in the presence or absence of the sample, and Chemerin or ligand binding is measured as appropriate for the binding assay being used. A decrease of 10% or more in the binding of Chemerin or other ligand indicates that the sample contains an agent that modulates Chemerin or ligand binding to the receptor polypeptide.

Functional Assays of Receptor Activity i. GTPase/GTP Binding Assays:

For GPCRs such as ChemerinR, a measure of receptor activity is the binding of GTP by cell membranes containing receptors. In the method described by Traynor and Nahorski, 1995, Mol. Pharmacol. 47: 848-854, incorporated herein by reference, one essentially measures G-protein coupling to membranes by measuring the binding of labeled GTP. For GTP binding assays, membranes isolated from cells expressing the receptor are incubated in a buffer containing 20 mM HEPES, pH 7.4, 100 mM NaCl, and 10 mM MgCl2, 80 pM $^{35}$S-GTPγS and 3 µM GDP. The assay mixture is incubated for 60 minutes at 30° C., after which unbound labeled GTP is removed by filtration onto GF/B filters. Bound, labeled GTP is measured by liquid scintillation counting. In order to assay for modulation of Chemerin-induced ChemerinR activity, membranes prepared from cells expressing a ChemerinR polypeptide are mixed with a Chemerin polypeptide, and the GTP binding assay is performed in the presence and absence of a candidate modulator of ChemerinR activity. A decrease of 10% or more in labeled GTP binding as measured by scintillation counting in an assay of this kind containing candidate modulator, relative to an assay without the modulator, indicates that the candidate modulator inhibits ChemerinR activity.

A similar GTP-binding assay can be performed without Chemerin to identify compounds that act as agonists. In this case, Chemerin-stimulated GTP binding is used as a standard. A compound is considered an agonist if it induces at least 50% of the level of GTP binding induced by full length wild-type Chemerin when the compound is present at 1 µM or less, and preferably will induce a level the same as or higher than that induced by Chemerin.

GTPase activity is measured by incubating the membranes containing a ChemerinR polypeptide with $γ^{32}$P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing ChemerinR (mock-transfected), in order to exclude possible non-specific effects of the candidate compound.

In order to assay for the effect of a candidate modulator on ChemerinR-regulated GTPase activity, membrane samples are incubated with a Chemerin polypeptide, with and without the modulator, followed by the GTPase assay. A change (increase or decrease) of 10% or more in the level of GTP binding or GTPase activity relative to samples without modulator is indicative of ChemerinR modulation by a candidate modulator.

ii. Downstream Pathway Activation Assays:

a. Calcium Flux—The Aequorin-Based Assay.

The aequorin assay takes advantage of the responsiveness of mitochondrial apoaequorin to intracellular calcium release induced by the activation of GPCRs (Stables et al., 1997, Anal. Biochem. 252:115-126; Detheux et al., 2000, J. Exp. Med., 192 1501-1508; both of which are incorporated herein by reference). Briefly, ChemerinR-expressing clones are transfected to coexpress mitochondrial apoaequorin and Gα16. Cells are incubated with 5 µM Coelenterazine H (Molecular Probes) for 4 hours at room temperature, washed in DMEM-F12 culture medium and resuspended at a concentration of $0.5 \times 10^6$ cells/ml. Cells are then mixed with test agonist peptides and light emission by the aequorin is recorded with a luminometer for 30 sec. Results are expressed as Relative Light Units (RLU). Controls include assays using membranes isolated from cells not expressing ChemerinR (mock-transfected), in order to exclude possible non-specific effects of the candidate compound.

Aequorin activity or intracellular calcium levels are "changed" if light intensity increases or decreases by 10% or more in a sample of cells, expressing a ChemerinR polypeptide and treated with a candidate modulator, relative to a sample of cells expressing the ChemerinR polypeptide but not treated with the candidate modulator or relative to a sample of cells not expressing the ChemerinR polypeptide (mock-transfected cells) but treated with the candidate modulator.

When performed in the absence of a Chemerin polypeptide, the assay can be used to identify an agonist of ChemerinR activity. When the assay is performed in the presence of a Chemerin polypeptide, it can be used to assay for an antagonist.

b. Adenylate Cyclase Assay:

Assays for adenylate cyclase activity are described by Kenimer & Nirenberg, 1981, Mol. Pharmacol. 20: 585-591, incorporated herein by reference. That assay is a modification of the assay taught by Solomon et al., 1974, Anal. Biochem. 58: 541-548, also incorporated herein by reference. Briefly, 100 µl reactions contain 50 mM Tris-Hcl (pH 7.5), 5 mM $MgCl_2$, 20 mM creatine phosphate (disodium salt), 10 units (71 µg of protein) of creatine phosphokinase, 1 mM α-$^{32}$P-ATP (tetrasodium salt, 2 µCi), 0.5 mM cyclic AMP, G-$^3$H-labeled cyclic AMP (approximately 10,000 cpm), 0.5 mM Ro20-1724, 0.25% ethanol, and 50-200 µg of protein homogenate to be tested (i.e., homogenate from cells expressing or not expressing a ChemerinR polypeptide, treated or not treated with a Chemerin polypeptide with or without a candidate modulator). Reaction mixtures are generally incubated at 37° C. for 6 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express a ChemerinR polypeptide.

According to the invention, adenylate cyclase activity is "changed" if it increases or decreases by 10% or more in a sample taken from cells treated with a candidate modulator of ChemerinR activity, relative to a similar sample of cells not treated with the candidate modulator or relative to a sample of cells not expressing the ChemerinR polypeptide (mock-transfected cells) but treated with the candidate modulator.

c. cAMP Assay:

Intracellular or extracellular cAMP is measured using a cAMP radioimmunoassay (RIA) or cAMP binding protein according to methods widely known in the art. For example, Horton & Baxendale, 1995, Methods Mol. Biol. 41: 91-105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

The level of cAMP is "changed" if the level of cAMP detected in cells, expressing a ChemerinR polypeptide and treated with a candidate modulator of ChemerinR activity (or in extracts of such cells), using the RIA-based assay of Horton & Baxendale, 1995, supra, increases or decreases by at least 10% relative to the cAMP level in similar cells not treated with the candidate modulator.

d. Phospholipid Breakdown, DAG Production and Inositol Triphosphate Levels:

Receptors that activate the breakdown of phospholipids can be monitored for changes due to the activity of known or suspected modulators of ChemerinR by monitoring phospholipid breakdown, and the resulting production of second messengers DAG and/or inositol triphosphate ($IP_3$). Methods of measuring each of these are described in *Phospholipid Signaling Protocols*, edited by Ian M. Bird. Totowa, N.J., Humana Press, 1998, which is incorporated herein by reference. See also Rudolph et al., 1999, J. Biol. Chem. 274: 11824-11831, incorporated herein by reference, which also describes an assay for phosphatidylinositol breakdown. Assays should be performed using cells or extracts of cells expressing ChemerinR, treated or not treated with a Chemerin polypeptide with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing a ChemerinR polypeptide and treated with a candidate modulator, relative to the level observed in a sample from cells expressing a ChemerinR polypeptide that is not treated with the candidate modulator.

e. PKC Activation Assays:

Growth factor receptor tyrosine kinases tend to signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-NH2 (SEQ ID NO: 80), derived from the myristoylated alanine-rich protein kinase C substrate protein (MARCKS). The $K_m$ of the enzyme for this peptide is approximately 50 μM. Other basic, protein kinase C-selective peptides known in the art can also be used, at a concentration of at least 2-3 times their $K_m$. Cofactors required for the assay include calcium, magnesium, ATP, phosphatidylserine and diacylglycerol. Depending upon the intent of the user, the assay can be performed to determine the amount of PKC present (activating conditions) or the amount of active PCK present (non-activating conditions). For most purposes according to the invention, non-activating conditions will be used, such that the PKC that is active in the sample when it is isolated is measured, rather than measuring the PKC that can be activated. For non-activating conditions, calcium is omitted in the assay in favor of EGTA.

The assay is performed in a mixture containing 20 mM HEPES, pH 7.4, 1-2 mM DTT, 5 mM $MgCl_2$, 100 μM ATP, ~1 μCi γ-$^{32}$P-ATP, 100 μg/ml peptide substrate (~100 μM), 140 μM/3.8 μM phosphatidylserine/diacylglycerol membranes, and 100 μM calcium (or 500 μM EGTA). 48 μl of sample, diluted in 20 mM HEPES, pH 7.4, 2 mM DTT is used in a final reaction volume of 80 μl. Reactions are performed at 30° C. for 5-10 minutes, followed by addition of 25 μl of 100 mM ATP, 100 mM EDTA, pH 8.0, which stops the reactions.

After the reaction is stopped, a portion (85 μl) of each reaction is spotted onto a Whatman P81 cellulose phosphate filter, followed by washes: four times 500 ml in 0.4% phosphoric acid, (5-10 min per wash); and a final wash in 500 ml 95% EtOH, for 2-5 min. Bound radioactivity is measured by scintillation counting. Specific activity (cpm/nmol) of the labeled ATP is determined by spotting a sample of the reaction onto P81 paper and counting without washing. Units of PKC activity, defined as nmol phosphate transferred per min, are calculated as follows:

$$\text{The activity, in UNITS (nmol/min) is:} = \frac{(cpm \text{ on paper}) \times \left(\frac{105 \text{ μl total}}{85 \text{ μl spotted}}\right)}{(\text{assay time, min})(\text{specific activity of } ATP \text{ cpm/nmol})}.$$

An alternative assay can be performed using a Protein Kinase C Assay Kit sold by PanVera (Cat. # P2747).

Assays are performed on extracts from cells expressing a ChemerinR polypeptide, treated or not treated with a Chemerin polypeptide with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing ChemerinR and treated with a candidate modulator, relative to a reaction performed on a similar sample from cells not treated with a candidate modulator.

f. Kinase Assays:

MAP kinase activity can be assayed using any of several kits available commercially, for example, the p38 MAP Kinase assay kit sold by New England Biolabs (Cat # 9820) or the FlashPlate™ MAP Kinase assays sold by Perkin-Elmer Life Sciences.

MAP Kinase activity is "changed" if the level of activity is increased or decreased by 10% or more in a sample from cells, expressing a ChemerinR polypeptide, treated with a candidate modulator relative to MAP kinase activity in a sample from similar cells not treated with the candidate modulator.

Direct assays for tyrosine kinase activity using known synthetic or natural tyrosine kinase substrates and labeled phosphate are well known, as are similar assays for other types of kinases (e.g., Ser/Thr kinases). Kinase assays can be performed with both purified kinases and crude extracts prepared from cells expressing a ChemerinR polypeptide, treated with or without a Chemerin polypeptide, with or without a candidate modulator. Control reactions should be performed using mock-transfected cells, or extracts from them in order to exclude possible non-specific effects of some candidate modulators. Substrates can be either full length protein or synthetic peptides representing the substrate. Pinna & Ruzzene (1996, Biochem. Biophys. Acta 1314: 191-225, incorporated herein by reference) list a number of phosphorylation substrate sites useful for measuring kinase activities. A number of kinase substrate peptides are commercially available. One that is particularly useful is the "Src-related peptide," RRLIEDAEYAARG (SEQ ID NO: 74; available from Sigma # A7433), which is a substrate for many receptor and nonreceptor tyrosine kinases. Because the assay described below requires binding of peptide substrates to filters, the peptide substrates should have a net positive charge to facilitate binding. Generally, peptide substrates should have at least 2 basic residues and a free amino terminus. Reactions generally use a peptide concentration of 0.7-1.5 mM.

Assays are generally carried out in a 25 µl volume comprising 5 µl of 5× kinase buffer (5 mg/mL BSA, 150 mM Tris-Cl (pH 7.5), 100 mM $MgCl_2$; depending upon the exact kinase assayed for, $MnCl_2$ can be used in place of or in addition to the $MgCl_2$), 5 µl of 1.0 mM ATP (0.2 mM final concentration), γ-32P-ATP (100-500 cpm/pmol), 3 µl of 10 mM peptide substrate (1.2 mM final concentration), cell extract containing kinase to be tested (cell extracts used for kinase assays should contain a phosphatase inhibitor (e.g. 0.1-1 mM sodium orthovanadate)), and $H_2O$ to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spun for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated 32P is measured by scintillation counting. The specific activity of ATP in the kinase reaction (e.g., in cpm/pmol) is determined by spotting a small sample (2-5 µl) of the reaction onto a P81 filter circle and counting directly, without washing. Counts per minute obtained in the kinase reaction (minus blank) are then divided by the specific activity to determine the moles of phosphate transferred in the reaction.

Tyrosine kinase activity is "changed" if the level of kinase activity is increased or decreased by 10% or more in a sample from cells, expressing a ChemerinR polypeptide, treated with a candidate modulator relative to kinase activity in a sample from similar cells not treated with the candidate modulator.

G. Transcriptional Reporters for Downstream Pathway Activation:

The intracellular signal initiated by binding of an agonist to a receptor, e.g., ChemerinR, sets in motion a cascade of intracellular events, the ultimate consequence of which is a rapid and detectable change in the transcription or translation of one or more genes. The activity of the receptor can therefore be monitored by measuring the expression of a reporter gene driven by control sequences responsive to ChemerinR activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, β-lactamase or β-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful to make reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The c-fos regulatory elements include (see, Verma et al., 1987, Cell 51: 513-514): a TATA box that is required for transcription initiation; two upstream elements for basal transcription, and an enhancer, which includes an element with dyad symmetry and which is required for induction by TPA, serum, EGF, and PMA.

The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is, as the name implies, responsive to levels of intracellular cAMP. Therefore, the activation of a receptor that signals via modulation of cAMP levels can be monitored by measuring either the binding of the transcription factor, or the expression of a reporter gene linked to a CREB-binding element (termed the CRE, or cAMP response element). The DNA sequence of the CRE is TGACGTCA (SEQ ID NO: 75). Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., 1988, Proc. Natl. Acad. Sci. 85:6662-6666); the somatostatin gene promoter (cAMP responsive; Montminy et al., 1986, Proc. Natl. Acad. Sci. 8.3:6682-6686); the proenkephalin promoter (responsive to cAMP, nicotinic agonists, and phorbol esters; Comb et al., 1986, Nature 323:353-356); the phosphoenolpyruvate carboxy-kinase (PEPCK) gene promoter (cAMP responsive; Short et al., 1986, J. Biol. Chem. 261:9721-9726).

Additional examples of transcriptional control elements that are responsive to changes in GPCR activity include, but are not limited to those responsive to the AP-1 transcription factor and those responsive to NF-κB activity. The consensus AP-1 binding site is the palindrome TGA(C/G)TCA (Lee et al., 1987, Nature 325: 368-372; Lee et al., 1987, *Cell* 49: 741-752). The AP-1 site is also responsible for mediating induction by tumor promoters such as the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include, but are not limited to the genes for Fos and Jun (which proteins themselves make up AP-1 activity), Fos-related antigens (Fra) 1 and 2, IκBα, ornithine decarboxylase, and annexins I and II.

The NF-κB binding element has the consensus sequence GGGGACTTTCC (SEQ ID NO: 81). A large number of genes have been identified as NF-κB responsive, and their control elements can be linked to a reporter gene to monitor GPCR activity. A small sample of the genes responsive to NF-κB includes those encoding IL-1β (Hiscott et al., 1993, Mol. Cell. Biol. 13: 6231-6240), TNF-α (Shakhov et al., 1990, J. Exp. Med. 171: 35-47), CCR5 (Liu et al., 1998, AIDS Res. Hum. Retroviruses 14: 1509-1519), P-selectin (Pan & McEver, 1995, J. Biol. Chem. 270: 23077-23083), Fas ligand (Matsui et al., 1998, J. Immunol. 161: 3469-3473), GM-CSF (Schreck & Baeuerle, 1990, Mol. Cell. Biol. 10: 1281-1286) and IκBα (Haskill et al., 1991, Cell 65: 1281-1289). Each of these references is incorporated herein by reference. Vectors encoding NF-κB-responsive reporters are also known in the art or can be readily made by one of skill in the art using, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct should be tested by exposing ChemerinR-expressing cells, transfected with the construct, to a Chemerin polypeptide. An increase of at least two-fold in the expression of reporter in response to Chemerin polypeptide indicates that the reporter is an indicator of ChemerinR activity.

In order to assay ChemerinR activity with a Chemerin-responsive transcriptional reporter construct, cells that stably express a ChemerinR polypeptide are stably transfected with the reporter construct. To screen for agonists, the cells are left untreated, exposed to candidate modulators, or exposed to a Chemerin polypeptide, and expression of the reporter is measured. The Chemerin-treated cultures serve as a standard for the level of transcription induced by a known agonist. An increase of at least 50% in reporter expression in the presence of a candidate modulator indicates that the candidate is a modulator of ChemerinR activity. An agonist will induce at least as much, and preferably the same amount or more, reporter expression than the Chemerin polypeptide. This approach can also be used to screen for inverse agonists where cells express a ChemerinR polypeptide at levels such that there is an elevated basal activity of the reporter in the absence of Chemerin or another agonist. A decrease in reporter activity of 10% or more in the presence of a candidate modulator, relative to its absence, indicates that the compound is an inverse agonist.

To screen for antagonists, the cells expressing ChemerinR and carrying the reporter construct are exposed to a Chemerin polypeptide (or another agonist) in the presence and absence of candidate modulator. A decrease of 10% or more in reporter expression in the presence of candidate modulator, relative to the absence of the candidate modulator, indicates that the candidate is a modulator of ChemerinR activity.

Controls for transcription assays include cells not expressing ChemerinR but carrying the reporter construct, as well as cells with a promoterless reporter construct. Compounds that are identified as modulators of ChemerinR-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening expression libraries for proteins for those that modulate ChemerinR activity. The libraries can be, for example, cDNA libraries from natural sources, e.g., plants, animals, bacteria, etc., or they can be libraries expressing randomly or systematically mutated variants of one or more polypeptides. Genomic libraries in viral vectors can also be used to express the mRNA content of one cell or tissue, in the different libraries used for screening of ChemerinR.

Any of the assays of receptor activity, including the GTP-binding, GTPase, adenylate cyclase, cAMP, phospholipid-breakdown, diacylglycerol, inositol triphosphate, PKC, kinase and transcriptional reporter assays, can be used to determine the presence of an agent in a sample, e.g., a tissue sample, that affects the activity of the ChemerinR receptor molecule. To do so, ChemerinR polypeptide is assayed for activity in the presence and absence of the sample or an extract of the sample. An increase in ChemerinR activity in the presence of the sample or extract relative to the absence of the sample indicates that the sample contains an agonist of the receptor activity. A decrease in receptor activity in the presence of Chemerin or another agonist and the sample, relative to receptor activity in the presence of Chemerin polypeptide alone, indicates that the sample contains an antagonist of ChemerinR activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. One exception is the transcriptional reporter assay, in which at least a two-fold increase or 10% decrease in signal is necessary for a sample to be said to contain a modulator. It is preferred that an agonist stimulates at least 50%, and preferably 75% or 100% or more, e.g., 2-fold, 5-fold, 10-fold or greater receptor activation than wild-type Chemerin.

Other functional assays include, for example, microphysiometer or biosensor assays (see Hafner, 2000, Biosens. Bioelectron. 15: 149-158, incorporated herein by reference).

II. Diagnostic Assays Based Upon the Interaction of ChemerinR and Chemerin:

Signaling through GPCRs is instrumental in the pathology of a large number of diseases and disorders. ChemerinR, which is expressed in cells of the lymphocyte lineages and which has been shown to act as a co-receptor for immunodeficiency viruses can have a role in immune processes, disorders or diseases. The ChemerinR expression pattern also includes bone and cartilage, indicating that this receptor can play a role in diseases, disorders or processes (e.g., fracture healing) affecting these tissues. Expression in adult parathyroid suggests possible importance in phosphocalic metabolism.

Because of its expression in cells of the lymphocyte lineages, ChemerinR can be involved in the body's response to viral infections or in diseases induced by various viruses, including HIV types I and II, or bacteria. The expression pattern of ChemerinR and the knowledge with respect to disorders generally mediated by GPCRs suggests that ChemerinR can be involved in disturbances of cell migration, cancer, development of tumors and tumor metastasis, inflammatory and neo-plastic processes, wound and bone healing and dysfunction of regulatory growth functions, diabetes, obesity, anorexia, bulimia, acute heart failure, hypotension, hypertension, urinary retention, osteoporosis, angina pectoris, myocardial infarction, restenosis, atherosclerosis, diseases characterised by excessive smooth muscle cell proliferation, aneurysms, diseases characterised by loss of smooth muscle cells or reduced smooth muscle cell proliferation, stroke, ischemia, ulcers, allergies, benign prostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourette's syndrome and other related diseases.

The interaction of ChemerinR with Chemerin can be used as the basis of assays for the diagnosis or monitoring of diseases, disorders or processes involving ChemerinR signaling. Diagnostic assays for ChemerinR-related diseases or disorders can have several different forms. First, diagnostic assays can measure the amount of ChemerinR and/or Chemerin polypeptide, genes or mRNA in a sample of tissue. Assays that measure the amount of mRNA encoding either or both of these polypeptides also fit in this category. Second, assays can evaluate the qualities of the receptor or the ligand. For example, assays that determine whether an individual expresses a mutant or variant form of either ChemerinR or Chemerin, or both, can be used diagnostically. Third, assays that measure one or more activities of ChemerinR polypeptide can be used diagnostically.

A. Assays that Measure the Amount of ChemerinR or Chemerin

ChemerinR and Chemerin levels can be measured and compared to standards in order to determine whether an abnormal level of the receptor or its ligand is present in a sample, either of which indicate probable dysregulation of ChemerinR signaling. Polypeptide levels are measured, for example, by immunohistochemistry using antibodies specific for the polypeptide. A sample isolated from an individual suspected of suffering from a disease or disorder characterized by ChemerinR activity is contacted with an antibody for ChemerinR or Chemerin, and binding of the antibody is measured as known in the art (e.g., by measurement of the activity of an enzyme conjugated to a secondary antibody).

Another approach to the measurement of ChemerinR and/or Chemerin polypeptide levels uses flow cytometry analysis of cells from an affected tissue. Methods of flow cytometry, including the fluorescent labeling of antibodies specific for ChemerinR or Chemerin, are well known in the art. Other approaches include radioimmunoassay or ELISA. Methods for each of these are also well known in the art.

The amount of binding detected is compared to the binding in a sample of similar tissue from a healthy individual, or from a site on the affected individual that is not so affected. An increase of 10% or more relative to the standard is diagnostic for a disease or disorder characterized by ChemerinR dysregulation.

ChemerinR and Chemerin expression can also be measured by determining the amount of mRNA encoding either or both of the polypeptides in a sample of tissue. mRNA can be quantitated by quantitative or semi-quantitative PCR. Methods of "quantitative" amplification are well known to those of skill in the art, and primer sequences for the amplification of both ChemerinR and Chemerin are disclosed herein. A common method of quantitative PCR involves simultaneously co-amplifying a known quantity of a control sequence using the same primers. This provides an internal standard that can be used to calibrate the PCR reaction. Detailed protocols for quantitative PCR are provided in *PCR Protocols, A Guide to Methods and Applications*, Innis et al., Academic Press, Inc. N.Y., (1990), which is incorporated herein by reference. An increase of 10% or more in the amount of mRNA encoding ChemerinR or Chemerin in a sample, relative to the amount expressed in a sample of like tissue from a healthy individual or in a sample of tissue from an unaffected location in an affected individual is diagnostic for a disease or disorder characterized by dysregulation of ChemerinR signaling.

B. Qualitative Assays

Assays that evaluate whether or not the ChemerinR polypeptide or the mRNA encoding it are wild-type or not can be used diagnostically. In order to diagnose a disease or disorder characterized by ChemerinR or Chemerin dysregulation in this manner, RNA isolated from a sample is used as a template for PCR amplification of Chemerin and/or ChemerinR. The amplified sequences are then either directly sequenced using standard methods, or are first cloned into a vector, followed by sequencing. A difference in the sequence that changes one or more encoded amino acids relative to the sequence of wild-type ChemerinR or Chemerin can be diagnostic of a disease or disorder characterized by dysregulation of ChemerinR signaling. It can be useful, when a change in coding sequence is identified in a sample, to express the variant receptor or ligand and compare its activity to that of wild type ChemerinR or Chemerin. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild-type and variant sequences. Hybridization assays that discriminate on the basis of changes as small as one nucleotide are well known in the art. Alternatively, any of a number of "minisequencing" assays can be performed, including, those described, for example, in U.S. Pat. Nos. 5,888,819, 6,004,744 and 6,013,431 (incorporated herein by reference). These assays and others known in the art can determine the presence, in a given sample, of a nucleic acid with a known polymorphism.

If desired, array or microarray-based methods can be used to analyze the expression or the presence of mutation, in ChemerinR or Chemerin sequences. Array-based methods for minisequencing and for quantitation of nucleic acid expression are well known in the art.

C. Functional Assays.

Diagnosis of a disease or disorder characterized by the dysregulation of ChemerinR signaling can also be performed using functional assays. To do so, cell membranes or cell extracts prepared from a tissue sample are used in an assay of ChemerinR activity as described herein (e.g., ligand binding assays, the GTP-binding assay, GTPase assay, adenylate cyclase assay, cAMP assay, phospholipid breakdown, diacyl glycerol or inositol triphosphate assays, PKC activation assay, or kinase assay). The activity detected is compared to that in a standard sample taken from a healthy individual or from an unaffected site on the affected individual. As an alternative, a sample or extract of a sample can be applied to cells expressing ChemerinR, followed by measurement of ChemerinR signaling activity relative to a standard sample. A difference of 10% or more in the activity measured in any of these assays, relative to the activity of the standard, is diagnostic for a disease or disorder characterized by dysregulation of ChemerinR signaling.

Modulation of ChemerinR Activity in a Cell According to the Invention

The discovery of Chemerin as a ligand of ChemerinR provides methods of modulating the activity of a ChemerinR polypeptide in a cell. ChemerinR activity is modulated in a cell by delivering to that cell an agent that modulates the function of a ChemerinR polypeptide. This modulation can be performed in cultured cells as part of an assay for the identification of additional modulating agents, or, for example, in an animal, including a human. Agents include Chemerin polypeptides as defined herein, as well as additional modulators identified using the screening methods described herein.

An agent can be delivered to a cell by adding it to culture medium. The amount to deliver will vary with the identity of the agent and with the purpose for which it is delivered. For example, in a culture assay to identify antagonists of ChemerinR activity, one will preferably add an amount of Chemerin polypeptide that half-maximally activates the receptors (e.g., approximately $EC_{50}$), preferably without exceeding the dose required for receptor saturation. This dose can be determined by titrating the amount of Chemerin polypeptide to determine the point at which further addition of Chemerin has no additional effect on ChemerinR activity.

When a modulator of ChemerinR activity is administered to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells) is changed by at least 10% relative to the value for that aspect prior to treatment.

Candidate Modulators Useful According to the Invention

Candidate modulators can be screened from large libraries of synthetic or natural compounds. Numerous means are currently used for random and directed synthesis of saccharide, peptide, lipid, carbohydrate, and nucleic acid based compounds. Synthetic compound libraries are commercially available from a number of companies including, for example, Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries of small organic molecules are available and can be prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

As noted previously herein, candidate modulators can also be variants of known polypeptides (e.g., Chemerin, antibodies) or nucleic acids (e.g., aptamers) encoded in a nucleic acid library. Cells (e.g., bacteria, yeast or higher eukaryotic cells) transformed with the library can be grown and prepared as extracts, which are then applied in ChemerinR binding assays or functional assays of ChemerinR activity.

III. Antibodies Useful According to the Invention

The invention provides for antibodies to ChemerinR and Chemerin. Antibodies of the invention include, but are not limited to, polyclonal, monoclonal, multispecific, human, humanized or chimeric antibodies, single-chain antibodies, Fab fragments, F(ab') fragments, etc. The antibodies of the invention can be any type (e.g., IgG, IgE, IgM, IgD, IgA, and IgY), class (e.g., IgG1-4, IgA1-2), or subclass of immunoglobulin molecule. In a preferred embodiment, the antibody is an IgG isotype. In another preferred embodiment, the antibody is an IgG1 isotype. In another preferred embodiment, the antibody is an IgG2 isotype. In another preferred embodiment, the antibody is an IgG4 isotype.

The antibodies of the invention may bind specifically to a polypeptide or polypeptide fragment or variant of Chemerin. Preferably, the antibodies of the invention bind specifically to the full-length Chemerin polypeptide. Also preferably, the antibodies of the invention bind specifically to the 157 amino acid truncated Preprochemerin polypeptide (SEQ ID NO: 73). Also preferably, the antibodies of the invention bind specifically to the 19 amino acid Chemerin polypeptide (SEQ ID NO: 53). Also preferably, the antibodies of the invention bind specifically to the 9 amino acid Chemerin polypeptide (SEQ ID NO: 59). Also preferably, the antibodies of the invention bind specifically to the Chemerin fragment FSKALPRS (SEQ ID NO: 89).

The antibodies of the invention may act as agonists or antagonists of the polypeptides of the invention. For example, the antibodies of the invention disrupt the Chemerin/ChemerinR interactions. The invention also features the antibodies that do not disrupt the Chemerin/ChemerinR interactions but disrupt the ChemerinR activation.

The antibodies of the invention may be used, for example, but not limited to, to purify, detect, and target the polypeptides of the invention, including both in vitro and in vivo diagnostic and therapeutic methods. For example, the antibodies of the invention can be used in immunoassays for qualitatively and quantitatively measuring levels of the polypeptides of the present invention in biological samples (*Antibodies: A Laboratory Manual*, Ed. by Harlow and Lane (Cold Spring Harbor Press: 1988)). The antibodies of the invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. The antibodies of the invention may also be modified by the covalent attachment of any type of molecule to the antibodies, including by glycosylation, acetylation, pegylation, phosphylation, phosphorylation, amidation, derivatization by known protecting/blocking groups, proteolytic cleavage, linkage to a cellular ligand or other protein, etc.

Antibodies can be made using standard protocols known in the art (See, for example, *Antibodies: A Laboratory Manual*, Ed. by Harlow and Lane (Cold Spring Harbor Press: 1988)). A mammal, such as a mouse, hamster, or rabbit can be immunized with an immunogenic form of the peptide (e.g., a ChemerinR or Chemerin polypeptide or an antigenic fragment which is capable of eliciting an antibody response, or a fusion protein as described herein above). Immunogens for raising antibodies are prepared by mixing the polypeptides (e.g., isolated recombinant polypeptides or synthetic peptides) with adjuvant. Alternatively, ChemerinR or Chemerin polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding ChemerinR or Chemerin, or a fragment of these proteins, can be used to express the polypeptides and generate an immune response in an animal as described in Costagliola et al., 2000, *J. Clin. Invest.* 105:803-811, which is incorporated herein by reference. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256: 495-497), the human B cell hybridoma technique (Kozbar et al., (1983) *Immunology Today*, 4:72), and the EBV-hybridoma technique to produce human monoclonal antibodies (Cole et al., (1985) *Monoclonal Antibodies and Cancer Therapy*, Alan R. Liss, Inc. pp. 77-96). Hybridoma cells can be screened immunochemically for production of antibodies specifically reactive with a Chemerin or ChemerinR peptide or polypeptide, and monoclonal antibodies isolated from the media of a culture comprising such hybridoma cells.

Antibody fragments of the invention may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments).

IV. Therapeutic Approaches Based on the Interaction of Chemerin and ChemerinR

Composition or Therapeutic Composition and Administration Thereof

The invention provides composition or therapeutic compositions that contain a Chemerin polypeptide or a Chemerin nucleic acid sequence as described above. The therapeutic compositions comprise a therapeutically effective amount of a compound including a Chemerin, and a pharmaceutically acceptable carrier. In a preferred embodiment, the composition is formulated in accordance with routine procedures as a pharmaceutical composition adapted for intravenous administration to human beings.

In another preferred embodiment, the composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, a composition will be administered in a single dosage in the range of 100 µg-100 mg/kg body weight, preferably in the range of 1 µg-100 µg/kg body weight. This dosage may be repeated daily, weekly, monthly, yearly, or as considered appropriate by the treating physician. Alternatively, the therapeutically effective amount of the composition of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

The invention also provides methods of treatment and inhibition for a disease or disorder by administration to a subject of an effective amount of a composition or therapeutic composition of the invention, preferably a nucleic acid or a polypeptide Chemerin molecule. In one aspect, the composition is substantially free from substances that limit effect or produce undesired side-effects of Chemerin. The subject can be any animal, and is preferably a mammal, and preferably a human.

Various delivery systems known in the art can be used to administer a composition of the invention, e.g., encapsulation in liposomes, microparticles, microcapsules, recombinant cells capable of expressing the composition of the invention, receptor-mediated endocytosis, etc, which are incorporated by reference herein. Methods of introduction include but are not limited to intradermal, intramuscular, intraperitoneal, intravenous, subcutaneous, intranasal, epidural, and oral routes. The compositions of the invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the compositions or the therapeutic compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

The invention also provides a pharmaceutical pack or kit comprising one or more containers filled with one or more of the ingredients of the pharmaceutical compositions of the invention.

Various diseases or disorders can be treated with the compositions or therapeutic compositions of the invention. They include, but are not limited to, neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital, as well as hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease.

Transgenic Animals Useful According to the Invention

Transgenic animals expressing ChemerinR or Chemerin or variants thereof are useful to study the signaling through ChemerinR, as well as for the study of drugs or agents that modulate the activity of ChemerinR. A transgenic animal is a non-human animal containing at least one foreign gene, called a transgene, which is part of its genetic material. Preferably, the transgene is contained in the animal's germ line such that it can be transmitted to the animal's offspring. A number of techniques may be used to introduce the transgene into an animal's genetic material, including, but not limited to, microinjection of the transgene into pronuclei of fertilized eggs and manipulation of embryonic stem cells (U.S. Pat. No. 4,873,191 by Wagner and Hoppe; Palmiter and Brinster, 1986, Ann. Rev. Genet., 20:465-499; French Patent Application 2593827 published Aug. 7, 1987, all of which are incorporated herein by reference). Transgenic animals can carry the transgene in all their cells or can be genetically mosaic.

According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains. Transgenes can be constitutively expressed or can be tissue specific or even responsive to an exogenous drug, e.g., Tetracycline. A transgenic animal expressing one transgene can be crossed to a second transgenic animal expressing a second transgene such that their offspring will carry and express both transgenes.

Knock-Out Animals

Animals bearing a homozygous deletion in the chromosomal sequences encoding either ChemerinR or Chemerin or variants can be used to study the function of the receptor and ligand. Of particular interest is whether a Chemerin knockout has a distinct phenotype, which may point to whether Chemerin is the only ligand that binds ChemerinR or if it is a member of a family. Of further particular interest is the identification of identification of ChemerinR/Chemerin in specific physiological and/or pathological processes.

i. Standard Knock Out Animals

Knock out animals are produced by the method of creating gene deletions with homologous recombination. This technique is based on the development of embryonic stem (ES) cells that are derived from embryos, are maintained in culture and have the capacity to participate in the development of every tissue in the animals when introduced into a host blastocyst. A knock out animal is produced by directing homologous recombination to a specific target gene in the ES cells, thereby producing a null allele of the gene. The technology for making knock-out animals is well described (see, for example, Huszar et al., 1997, Cell, 88:131; and Ohki-Hamazaki et al., 1997, Nature, 390:165, both of which are incorporated herein by reference). One of skill in the art can generate a homozygous ChemerinR or Chemerin knock-out animal (e.g., a mouse) using the sequences for ChemerinR and Chemerin (disclosed herein and known in the art) to make the gene targeting construct.

ii. Tissue Specific Knock Out

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue (Marth, 1996, Clin. Invest. 97: 1999). In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function (Sauer, 1998, Methods, 14:381). There are now many in vivo examples of this method, including, for instance, the inducible inactivation of mammary tissue specific genes (Wagner et al., 1997, Nucleic Acids Res., 25:4323). One of skill in the art can therefore generate a tissue-specific knock-out animal in which ChemerinR or Chemerin is homozygously eliminated in a chosen tissue or cell type.

Kits Useful According to the Invention

The invention provides for kits useful for screening for modulators of ChemerinR activity, as well as kits useful for diagnosis of diseases or disorders characterized by dysregulation of ChemerinR signaling. Kits useful according to the invention can include an isolated ChemerinR polypeptide (including a membrane- or cell-associated ChemerinR polypeptide, e.g., on isolated membranes, cells expressing ChemerinR, or, on an SPR chip) and an isolated Chemerin polypeptide. A kit can also comprise an antibody specific for ChemerinR and/or an antibody for Chemerin. Alternatively, or in addition, a kit can contain cells transformed to express a ChemerinR polypeptide and/or cells transformed to express a Chemerin polypeptide. In a further embodiment, a kit according to the invention can contain a polynucleotide encoding a ChemerinR polypeptide and/or a polynucleotide encoding a Chemerin polypeptide. In a still further embodiment, a kit according to the invention may comprise the specific primers useful for amplification of ChemerinR or Chemerin as described below. All kits according to the invention will comprise the stated items or combinations of items and packaging materials therefor. Kits will also include instructions for use.

Expression Vectors

The present invention also relates to vectors containing the Chemerin and host cells, as well as the production of the Chemerin polypeptide by recombinant techniques. The vector may be a phage, plasmid, viral, or retroviral vector. The Chemerin polynucleotides may be joined to a vector containing a selectable marker propagation in a host. The Chemerin polynucleotide should be operatively linked to an appropriate promoter, as the phage lambda PL promoter, the E. coli lac, trp, phoA and tac promoters, the SV40 early and late promoters and promoters of retroviral LTRs. The expression vectors will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated. The expressing vectors will also include one or more promoters. Suitable promoters which may be employed include, but are not limited to, retroviral LTR, the SV40 promoter, adenoviral promoters; heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the .beta.-actin promoter; and human growth hormone promoters. The promoter also may be the native promoter which controls the genes encoding the polypeptides.

As indicated, the expression vectors will preferably include at least one selectable marker. Such markers include dihydrofolate reductase, G418, glutamine synthase or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, NSO, COS, 293, and Bowes melanoma cells; and plant cells. Appropriate culture mediums and conditions for the above-described host cells are known in the art.

Gene Transfer Methods

Gene therapy has been studied and used for treating various types of diseases. Generally, gene therapy comprises delivering a gene of interest to cells affected with diseases for correction of abnormal conditions. The invention provides for gene transfer methods of the Chemerin gene for treatment of diseases including tumors/cancers such as cancers in lung, prostate, oesophagus, Pharynx, Colon-rectum, liver-bilary tract, stomach, larynx, pancreas, bladder, breast, colon-rectum, ovary, stomach, womb-leasing, pancreas, lung, liver, lymphoma, leukemia. Gene transfer of the Chemerin gene in accordance with the present invention can be accomplished through many means, including by both viral vectors and by non-viral methods.

The non-viral gene transfer methods include plasmid DNA expression vectors, liposomes, receptor-mediated endocytosis, and particle-mediated (gene gun) methods etc. All these methods are well known in the art and are incorporated by reference herein.

The viral gene transfer methods include retrovirus (including lentivirus), adenovirus, adeno-associated virus, herpes simplex virus, vaccinia, fowlpox, canarypox virus, Sindbis virus etc, which are well known in the art. In one embodiment, the gene transfer relates to recombinant retrovirus vectors such as the virus based on Mouse Moloney Leukemia virus, the chimeric Moloney-Human lentiviral (HIV) vector etc.

In another embodiment, the gene transfer relates to human adenoviruses. The human adenovirus is a 36 kb double-stranded DNA virus containing genes that express more than 50 gene products throughout its life cycle. By eliminating the E1 region of the vector, the virus lacks ability to self-replicate and space is made for placing therapeutic expression sequences. The adenovirus vectors have been shown to be especially efficient at transferring genes into most tissues after in vivo administration. In another particular embodiment, the adenovirus vector can be modified to exhibit tissue-specific, tumor-selective expression (Doronin, K et al. (2001) *J. Virology,* 75:3314-3324). In one example, the adenovirus promoter E1A region is deleted and replaced with a modified promoter for α-fectoprotein (AFP). The expression of this modified adenovirus vector is limited to hepatocellular carcinoma cells (Hallenbeck, P L et al. (1999) *Human Gene Ther.* 10:1721-1733). In another example, the adenovirus E4 promoter region is deleted and replaced with the promoter for surfactant protein B (SPB). The expression of the modified adenovirus is limited to lung carcinoma cells (Doronin, K et al. (2001) *J. Virology,* 75:3314-3324).

In another embodiment, the gene transfer relates to recombinant adeno-associated virus (AAV) vectors. The AAV vectors contain small, single-stranded DNA genomes and have been shown to transduce brain, skeletal muscle, and liver tissues.

The cells targeted for gene transfer include any cells to which the delivery of the Chemerin gene is desired. Generally, the cells are those affected with diseases such as but not limited to tumoric cells. Various mammalian cell lines can also be employed for gene transfer, examples includes, but not limited to, COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. In particular, the cells are cell lines derived from tissues affected by diseases, such as cancer cell lines.

Ex Vivo Therapeutic Approaches Based on the Interaction of Chemerin and ChemerinR The ex vivo gene therapy involves removing cells from the blood or tissues of a subject, genetically modifying in vitro, and subsequently transplanting back into the same recipient. In one embodiment, a nucleic acid sequence is introduced into a cell prior to administration in vivo of the resulting recombination cell. Such introduction can be carried out by any method known in the art, including but not limited to transfection, electroporation, microinjection, infection with a viral or bacteriophage vector containing the nucleic acid sequence, cell fusion, chromosome-mediated gene transfer, microcell-mediated gene transfer, spheroplast fusion, etc, all are known in the art. The gene transfer methods should provide for stable transfer of the nucleic acid sequence to the cell, so that the nucleic acid sequence is expressible in the cell and preferably heritable and expressible by its cell progeny. The resulting recombinant blood cells are preferably administered intravenously. The amount of cells envisioned for use depends on the desired effect, patient state, etc., and can be determined by one skilled in the art. Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the nucleic acid sequence encodes a Chemerin polypeptide including the polypeptides ranging from the truncated to the full-length and the variants of the Chemerin polypeptide that bind specifically to a ChemerinR polypeptide. In a preferred embodiment, the cell used for ex vivo gene therapy is autologous to the recipient.

In another preferred embodiment, cells used are dendritic cells. For example, dendritic cells can be derived from hematopoietic progenitors or from adherent peripheral blood monocytes. The cultured dendritic cells are then loaded with tumor-associated antigens. Tumor antigen loading can be accomplished by a variety of techniques including (1) pulsing with purified defined peptides or modified tumor lysate, (2) co-culture with apoptotic tumor cells, (3) transfection with RNA, (4) fusion with tumor cells, or (5) gene transfer with viral or non-viral gene transfer systems as described above. The loaded dendritic cells are injected into a subject for stimulating immune response of the subject.

In another embodiment, cells can be pulsed with different types of compositions, preferably proteins or peptides. Such technique is known to one skilled in the art and is described in Nestle et al. (1998) *Nat. Med.* 4:328-332. Briefly, cells are transferred into a suitable medium and incubated in vitro for an appropriate time with the composition. The cells are then washed and resuspended in a suitable volume of medium for in vivo transfer. In a preferred embodiment, the cells used for peptide pulsing are of the same species as the individual to whom the composition should be applied. In a particularly preferred embodiment, the cells are autologous to the recipient. In another particularly preferred embodiment, the cells are dendritic cells.

Particular examples of ex vivo dendritic cell gene therapy include those that have been assessed in melanoma (Nestle et al. (1998) *Nat. Med.* 4:328-332), renal cancer (Kurokawa et al. (2001), *Int. J. Cancer,* 91:749-756), glioma (Yu et al (2001), *Cancer Res.,* 61:842-847), breast and ovarian (Brossart et al. (2000), *Blood,* 96:3102-3108), prostate (Burch et al. (2000), *Clin. Cancer Res.,* 6:2175-2182), gastrointestinal, colon and lung (Fong et al. (2001) *J. Immunl.,* 166:4254-4259).

In Vivo Gene Therapy

The present invention provides in vivo gene therapy methods. Such methods involve the direct administration of nucleic acid or a nucleic acid/protein complex into the individual being treated. For example, successful examples of animal models with in vivo gene therapy can be found in treatment of lung cancer (Zhang and Roth (1994), *In Vivo,* 8(5):755-769) and cutaneous melanoma (Gary et al. (1993), *PNAS USA,* 90:11307-11311), etc.

The nucleic acid or protein is preferably Preprochemerin or ChemerinR (SEQ ID NO: 7), truncated Preprochemerin (SEQ ID NO: 72) or ChemerinR (SEQ ID NO: 1) of the invention. In vivo administration can be accomplished according to a number of established techniques including, but not limited to, injection of naked nucleic acid, viral infection, transport via liposomes and transport by endocytosis as described above. Suitable viral vectors include, for example, adenovirus, adeno-associated virus and retrovirus vectors etc as described in detail above.

The Preprochemerin or truncated Preprochemerin polynucleotides in a vector can be delivered to the interstitial space of tissues with a subject, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue.

In one embodiment of the invention, the Preprochemerin polynucleotides or truncated Preprochemerin/Chemerin or truncated Preprochemerin polypeptides are complexed in a liposome preparation. Liposomal preparations for use in the present invention include cationic, anionic, and neutral preparations, all are well known in the art.

In one embodiment, a retroviral vector containing a Preprochemerin or truncated Preprochemerin RNA sequence is used for in vivo gene therapy. In another embodiment of the invention, an adenovirus-associated virus vector containing a preprochemerin or truncated Preprochemerin polynucleotides is used. In another embodiment, an adenovirus vector containing a Preprochemerin polypeptide is used.

In one embodiment of the invention, the viral vectors for gene transfer are adenovirus vectors whose promoters are modified so that the expression of the vectors is limited to a specific tumor or a particular tissue. This type of vectors have the advantages of delivering the gene of interest to the targeted location, thus reducing the chance of harm due to the unspecific delivery of the viral vector to a variety of tissues including the normal cell tissues.

In a particular embodiment of the invention, the in vivo gene therapy includes administering the gene that encodes a Preprochemerin or truncated Preprochemerin polypeptide into a subject for stimulating immune response of the subject or therapeutic treatment of a disease. Preferably, the gene encoding a Preprochemerin or truncated Preprochemerin polypeptide is administered by a plasmid vector, or a viral vector, or non-viral methods. Preferably, the gene encoding a Preprochemerin or truncated Preprochemerin polypeptide is administered by a adenovirus vector whose expression is tissue-specific and/or tumor-selective.

The polynucleotides encoding Preprochemerin or truncated Preprochemerin may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

EXAMPLES

In the following examples, all chemicals are obtained from Sigma, unless stated. The cell culture media are from Gibco BRL and the peptides are from Bachem.

Example 1

Cloning of Human ChemerinR Receptor

Human ChemerinR was cloned as described in Samson et al. (1998) (SEQ ID NOS: 1 and 2). As an example of one set of steps one could use to clone other ChemerinR polypeptides useful according to the invention, the method is described here. In order to clone the ChemerinR sequence, a classical cloning procedure was performed on human genomic DNA.

A clone, designated HOP 102 (ChemerinR), was amplified from human genomic DNA by using degenerate oligonucleotides. HOP 102 shared 45-50% identity with fMLP and C5a receptors and somewhat lower similarities with the family of chemokine receptors (FIG. 5). This partial clone was used as a probe to screen a human genomic library and three overlapping lambda clones were isolated. A restriction map of the clones was established and a 1.7 kb XbaI fragment was subcloned in pBS SK+ (Stratagene) and sequenced on both strands. The sequence was found to include the HOP 102 probe entirely, with 100% identity. This novel gene was named ChemerinR (GenBank Accession No. Y14838).

Amplification of coding sequence of ChemerinR resulted in a fragment of 1.1 kb. This fragment was subcloned into the pcDNA3 (Invitrogen) vector and sequenced on both strands (FIGS. 1 and 2).

The mouse and rat ortholog genes are disclosed in FIGS. 3 and 4 respectively.

Example 2a

Purification of the Natural Ligand of ChemerinR and Identification of Chemerin

Approximately one liter of a human ascitic fluid from a patient with ovarian cancer was prefiltered and then filtered successively through 0.45 and 0.22 μm Millex filters (Millipore).

In step 1, the ascite was directly loaded onto a C18 reverse-phase column (10 mm×100 mm POROS 20 R2 beads, Applied Biosystems) pre-equilibrated with 5% $CH_3CN$/0.1% TFA at a flow-rate of 20 ml/min at room temperature. A 5-95% gradient of $CH_3CN$ in 0.1% TFA was then applied with a slope of 6%/min. 5-milliliter fractions were collected, and 20 μl of each fraction was set aside and assayed for $[Ca^{2+}]$ transients in ChemerinR-expressing CHO cells.

In step 2, the active fractions (approx. 10 fractions eluting between 25 and 40% $CH_3CN$) were pooled, adjusted at pH 5, filtered through a 20 μm Millex filter (Millipore), diluted 3-fold in acetate buffer at pH 4.8 and then applied to a cation-exchange HPLC column (Polycat 9.6 mm×250 mm, Vydac) pre-equilibrated with acetate buffer at pH 4.8 and 4° C. A 0-1M gradient of NaCl in acetate buffer at pH 4.8 was applied with 10%/min at a flow-rate of 4 ml/min. 1-milliliter fractions were collected and a 25 μl-aliquot from each fraction was used for the $[Ca^{2+}]$ assay after desalting on a 10 kDa-cut-off membrane (Ultrafree, Millipore).

In step 3, the active fractions (eluted with approx. 700 mM NaCl) were pooled and desalted onto a 10 kDa-cut-off Ultrafree membrane to approx. 10 mM NaCl concentration. The eluates from distinct cation-exchange HPLC runs were pooled and loaded onto a second cation-exchange HPLC column (Polycat 2.1 mm×250 mm, Vydac) pre-equilibrated with acetate buffer at pH 4.8 and 4° C. A 0-1 M gradient of NaCl in acetate buffer at pH 4.8 was applied at a flow-rate of 1 ml/min. with a slope of 2%/min. 0.5-milliliter fractions were collected and a 20 μl-aliquot from each fraction was used for intracellular calcium assay after desalting onto a 10 kDa-cut-off Ultrafree membrane.

In step 4, the active fractions were pooled, diluted 8-fold with $H_2O$/0.1% $H_3PO_4$ and loaded onto an analytical C18 reverse-phase column (4.6 mm×250 mm, Vydac) pre-equilibrated with 5% $CH_3CN$/0.1% $H_3PO_4$ at a flow-rate of 1 ml/min at room temperature. A 5-95% gradient of $CH_3CN$ in 0.1% $H_3PO_4$ was applied with a 0.3%/min. gradient between 25 and 40% of $CH_3CN$. Individual UV absorption peaks (214 nm) were collected manually, and approx. 5% from each fraction volume was assayed for biological activity.

In step 5, the active peaks (approximatively 28% $CH_3CN$) were diluted 6-fold with $H_2O$/0.1% TFA and directly loaded onto a second C18 reverse-phase column (1 mm×50 mm, Vydac) pre-equilibrated with 5% $CH_3CN$/0.1% TFA at a flow-rate of 0.1 ml/min. at room temperature. A 5-95% gradient of $CH_3CN$ in 0.1% TFA was applied with a 0.3%/min. gradient between 30 and 45% of $CH_3CN$. The final peak was collected manually at 40% $CH_3CN$ and analysed by mass spectrometry. 800 ml of ovarian cancer ascites fluid yielded 50 fmoles of Chemerin.

The active fraction was completely dried in a speed-vac and resuspended in 10 μl of 0.1M Tris at pH 8.7. After boiling the sample during 15 min at 95° C., the sample was incubated at 37° C. overnight in the presence of 250 ng of modified trypsin (Promega). The digested sample was then purified by solid-phase extraction onto a C18 ZipTip (Millipore). The eluted sample (1.5 μl in 70% $CH_3CN$/0.1% TFA) was applied onto a MALDI target in the presence of 120 mg/ml dihydroxy-benzoic acid matrix and then analysed on a MALDI-Q-TOF prototype (Micromass). Eight peptides were predicted to derive from the product of the human tazarotene-induced gene (Tig)-2 (FIG. 20), covering 91 aminoacids out of the 143 aminoacid-long sequence of the Tig-2 gene product (after removal of the predicted signal peptide). However, the C-terminal peptide (peptide 8) was not tryptic, lacking the last six amino acids of the predicted protein. This observation indicated that the active compound might result from the proteolytic processing of the encoded precursor (FIGS. 12 and 13).

Example 2b

Purification of Human Native Chemerin (FIG. 21)

One liter of ascitic fluid was filtered and loaded (50 ml per run) onto a reverse-phase column (10×100 mm, Poros 20 R2 beads, Applied Biosystems). A 5-95% $CH_3CN$ gradient (6%/min) in 0.1% TFA was applied, 5 ml fractions were collected and assayed for ChemR23 activation. Active fractions were adjusted to pH 4.8 and applied to a cation-exchange HPLC column (Polycat 9.6×250 mm, Vydac) in the presence of 10% $CH_3CN$, eluted with a 0-1 M NaCl gradient (10%/min) in acetate buffer pH 5. Active fractions were desalted (Ultrafree, cut-off: 10 kDa, Millipore), loaded onto a second cation-exchange column (Polycat 2.1×250 mm, Vydac) and eluted with the same buffer (2%/min NaCl gradient). Active fractions (0.5 ml, desalted) were pooled, diluted 8-fold with 0.1% $H_3PO_4$ and loaded onto a C18 column (4.6×250 mm, Vydac). A 5-95% $CH_3CN$ gradient (0.3%/min) in 0.1% $H_3PO_4$ was applied and individual UV absorption peaks (214 nm) were collected manually and assayed. The active fractions were loaded onto a second C18 column (2.1×250 mm, Vydac, 5-95% $CH_3CN$ in 0.1% TFA, 0.3%/min). The peaks were collected manually and analyzed by mass spectrometry. The use of human material collected for diagnostic or therapeutic purposes was approved by the ethical committee of the Medical School of the Université Libre de Bruxelles.

Example 2c

Mass Spectrometry Analysis

The active fractions were vacuum dried, resuspended in 10 μl of 100 mM Tris-HCl pH 8.7, heated for 15 min at 95° C., incubated overnight at 37° C. with 250 ng of trypsin (Promega) and purified by solid-phase extraction (C18 Zip-Tip, Millipore). The digested peptides were eluted in 1.5 µl of 70% CH$_3$CN/0.1% TFA onto a metallic MALDI target, dried and then mixed in 1.5 µl of matrix mix (2 mg/ml 2,5-dihydroxybenzoic acid and 10 mg/ml (-cyano-4-hydroxycinnamic acid, 2 mM fucose, 5 mM ammonium acetate). For proteic samples excised from SDS/acrylamide gels, the samples were processed as described (14). For determination of the N-terminus of the recombinant protein, the digested peptides were first separated onto a C18 column (1×250 mm, Vydac, 5-95% CH$_3$CN in 0.1% TFA, 2%/min) and each HPLC fraction was analyzed separately. Mass spectrometry analysis was performed on a Q-TOF Ultima Global mass spectrometer equipped with a MALDI source (Micromass), and calibrated using the monoisotopic masses of tryptic and chymotryptic peptides from bovine serum albumin. Ionization was achieved using a nitrogen laser (337 nm beam, 10 Hz) and acquisitions were performed in a V mode reflectron position. Microsequencing was performed by argon-induced fragmentation after selection of the parent ion.

Eight peptides were predicted to derive from the product of the human tazarotene-induced gene (TIG)-2 (FIG. 22), covering 91 aminoacids out of the 143 aminoacid-long sequence of the TIG-2 gene product (after removal of the predicted signal peptide). However, the C-terminal peptide (peptide 8) was not tryptic lacking the last six amino acids of the predicted protein. This observation indicated that the active compound might result from the proteolytic processing of the encoded precursor (Table 1 and FIG. 22).

TABLE 1

Sequences of Peptides found in monoisotopic mass fingerprinting
The two peptides indicated with an asterisk were microsequenced by MS/MS fragmentation.
The position of the peptides is defined in comparison with Preprochemerin amino acid sequence (SEQ ID NO: 8)

| Residues # | Sequence | M + H |
|---|---|---|
| 72-78 | (K) LQQTSCR (K) [SEQ. ID. NO: 15] | 835.41 |
| 81-88 | (R) DWKKPECK (V) [SEQ. ID. NO: 16] | 1033.51 |
| 29-39* | (R) GLQVALEEFHK (H) [SEQ. ID. NO: 17] | 1270.68 |
| 98-109 | (K) CLACIKLGSEDK (V) [SEQ. ID. NO: 18] | 1279.64 |
| 114-125* | (R) LVHCPIETQVLR (E) [SEQ. ID. NO: 19] | 1407.78 |
| 28-39 | (R) RGLQVALEEFHK (H) [SEQ. ID. NO: 20] | 1426.78 |
| 126-137 | (R) EAEEHQETQCLR (V) [SEQ. ID. NO: 21] | 1472.64 |
| 141-157 | (R) AGEDPHSFYFPGQFAFS (K) [SEQ. ID. NO: 22] | 1904.02 |

Example 3

Cloning and Recombinant Expression of Human Chemerin

In order to clone the Chemerin sequence (FIG. 6, GenBank Accession No. Q99969) a polymerase chain reaction (PCR) was performed on kidney cDNA (Clontech Laboratories). Primers were synthesized based upon the human Chemerin sequence and were as follows:

```
hChemerin fw:
5' CAGGAATTCAGCATGCGACGGCTGCTGA 3'   SEQ ID NO: 23 hChemerin rv:
5' GCTCTAGATTAGCTGCGGGGCAGGGCCTT 3'  SEQ ID NO: 24
```

Amplification was performed with Qiagen Taq polymerase in the conditions described by the supplier and with the following cycles: 3 min at 94° C., 35 cycles of 1 min at 94° C., 90 sec at 58° C. and 90 sec at 72° C., followed by a final incubation of 10 min at 72° C. The amplification resulted in a fragment of 500 bp containing the entire coding sequence of the Chemerin gene. This fragment was subcloned into the vector pcDNA3 (Invitrogen) for DNA sequencing analysis.

Maxiprep (Quiagen) DNA was used in transient transfections of HEK293 cells expressing large T antigen (293T) and COS-7 cells using Fugene6 in 10 cm plates. In parallel, transfections were performed in the same cell lines with the expression vector alone (Mock transfected). 24 hours after transfection, the medium was replaced by 9 ml DMEM-F12, 1% BSA, and 3 ml of supernatant were collected each 24 h for three days (48, 72 and 96 h post transfection). CHO cells were transfected with the same plasmid and transfected cells were selected with G418. The activity of the conditioned medium was verified on ChemerinR expressing cells using the aequorin assay.

Example 4

Recombinant Expression of Chemerin in Yeasts

The coding sequences of human and mouse Chemerin are amplified by PCR using the following primers (Two different primers are used for amplification of 5' end of human Chemerin to take into account the different predictions of the signal peptide of this protein):

```
mChemerinf:  5' TCTCTCGAGAAAAGAGAGGCTGAAGCTACACGTGGGACAGAGCCCGAA 3'  SEQ ID NO: 25 hChemerinaf: 5' TCTCTCGAGAAAAGAGAGGCTGAAGCTGGCGTCGCCGAGCTCACGGAA 3'  SEQ ID NO: 26 hChemerinbf: 5' TCTCTCGAGAAAAGAGAGGCTGAAGCTGTGGGCGTCGCCGAGCTCACG 3'  SEQ ID NO: 27
```

```
mChemerinr:   5' AGGGAATTCTTATTTGGTTCTCAGGGCCCT 3'        SEQ ID NO: 28 hChemerinr:   5' AGGGAATTCTTAGCTGCGGGGCAGGGCCTT 3'        SEQ ID NO: 29
```

The amplified Chemerin sequences are cloned, sequenced and inserted in pPIC9K, a multicopy *Pichia* expression plasmid (InVitrogen) containing the signals directing secretion of expressed proteins. Following transformation, *Pichia pastoris* cells are selected using G418 antibiotic. After selection, 20 clones are analyzed for their expression and the clone with the highest expression is amplified for large scale expression in shaker flasks. The medium is collected, centrifuged and used for partial purification with a protocol derived from the one used for Chemerin initial purification (see above).

Example 5

Recombinant Expression of Chimaeric Chemerin Fused with Secreted Alkaline Phosphatase (SEAP)

The coding sequences of mouse and human Chemerin are amplified by PCR, cloned and sequenced. PCR and sequencing primers are as follows:

```
mChemerinf:
CAGGAATTCGCCATGAAGTGCTTGCTGA          (SEQ ID NO: 30)

hChemerinf:
CAGGAATTCAGCATGCGACGGCTGCTGA          (SEQ ID NO: 31)

mChemerinr:
GCTCTAGATTTGGTTCTCAGGGCCCTGGA         (SEQ ID NO: 32)

hChemerinr:
GCTCTAGAGCTGCGGGGCAGGGCCTTGGA         (SEQ ID NO: 33)
```

The cloned Chemerin sequences are then subcloned into the mammalian bicistronic expression vector, pcDNA3, to obtain a fusion protein with Chemerin linked at its carboxy terminal end to secreted alkaline phosphatase, tagged with six histidine residues (His6). Mammalian cells, including COS-7, HEK-293 expressing the large T antigen (293 T) and CHO-K1 cells, are transfected with this plasmid using Fugene 6™ and incubated for 3-4 days in complete Ham's F12 medium (Nutrient Mixture Ham's F12 (Life Technologies) containing 10% fetal bovine serum; 100 IU/ml penicillin, 100 μg/ml streptomycin and 2.5 μg/ml fungizone (Amphotericin B). The supernatant containing Chemerin-SEAP-His6 is collected after centrifugation, filtered (0.45 μm) and stored at 4° C. after adding 20 mM Hepes (pH 7.4) and 0.02% sodium azide.

For one-step affinity purification of the Chemerin fusion protein, the supernatant is applied to 1 ml of Hisbond resin (Qiagen). After washing, bound Chemerin-SEAP-His6 is eluted with a gradient of imidazol. The concentration of isolated Chemerin-SEAP-His6 is determined by a sandwich type enzyme-linked immunosorbent assay. Briefly microtiter plates are coated with anti-placental alkaline phosphatase antibody. After blocking with 1 mg/ml bovine serum albumin (BSA) in phosphate buffered saline, the samples are titrated and incubated for 1 h at room temperature. After washing, plates are incubated with biotinylated rabbit anti-placental alkaline phosphatase diluted 1:500 for 1 h at room temperature, washed again, and incubated with peroxidase-conjugated streptavidin for 30 min. After washing, bound peroxidase is reacted with 3,3',5,5'-tetramethylbenzidine. The reaction is stopped by adding 1 N $H_2SO_4$, and absorbance at 450 nm is measured. Alkaline phosphatase activity is determined by a chemiluminescent assay using the Great Escape™ detection kit (Clontech). Purified placental alkaline phosphatase is used to generate a standard curve. The enzymatic activity is expressed as relative light units/sec.

Example 6

Quantitative RT-PCR

ChemerinR and Chemerin transcripts were detected by quantitative RT-PCR (TaqMan) in total or polyA+ RNA samples from human tissues and blood cell populations obtained commercially (Clontech and Ambion) or prepared locally (RNeasy Mini Kit, Qiagen). Primers were 5'-GCAGACAAGCTGCCGGA-3' (SEQ ID NO: 34) as forward, 5'-AGTTTGATGCAGGCCAGGC-3' (SEQ ID NO: 35) as reverse and 5'-AACCCGAGTGCAAAGTCAGGCCC-3' (SEQ ID NO: 36) as probe for Chemerin, 5'-GTCCCAGAACCACCGCAG-3' (SEQ ID NO: 37) as forward, 5'-AAGAAAGCCAGGACCCAGATG-3' (SEQ ID NO: 38) as reverse and 5'-TTCGCCTGGCTTACAT GGCCTGC-3' (SEQ ID NO: 39) as probe for ChemerinR and 5'-GAAGGTGAAGGTCGGAGTC-3' (SEQ ID NO: 40) as forward, 5'-GAAGATGGTGATGGGATTTC-3' (SEQ ID NO: 41) as reverse and 5'-AGCTCTCCCGCCGGCCTCTG-3' (SEQ ID NO: 42) as probe for the reference housekeeping gene glyceraldehyde-3-phosphate dehydrogenase (GAPDH). Standard curves were run systematically for the three genes, and the transcript copy number of proChemerin and ChemerinR was normalized to the GAPDH transcript copy number for each sample.

We investigated the presence of prochemerin and chemerinR transcripts in various human tissues and leukocyte populations by real-time RT-PCR (Taqman). In addition to immature dendritic cells, chemerinR transcripts were found primarily in spleen, lymph nodes and lung, and at lower levels in a number of other tissues (FIG. 24B). Abundant chemerin transcripts were found in liver, lung, pituitary and ovary (FIG. 24C), and lower levels could be detected in most tissues. Interestingly however, no expression of chemerin was found in peripheral blood leukocyte populations. Monoclonal antibodies generated against human chemerinR by genetic immunization (as described in Costagliola et al., 1998), and characterized by FACS on CHO-K1 cell lines expressing the receptor (data not shown) were used to confirm the presence of the receptor at the surface of dendritic cells and macrophages. High levels of chemerinR immunoreactivity were found on monocyte-derived immature dendritic cells, and chemerinR was downmodulated following maturation of the cells as a result of LPS or CD40L stimulation (FIGS. 24, D and E). Similarly, chemerinR immunoreactivity was observed at the surface of monocyte-derived human macrophages (FIG. 24F).

Example 7

Functional Assay for ChemerinR

ChemerinR-expressing clones have been obtained by transfection of CHO-K1 cells to coexpressing mitochondrial apoaequorin and Gα16, limiting dilution and selection by northern blotting. Positive clones were used for screening with human ovarian cancer ascites extracts prepared as described above. A functional assay based on the luminescence of mitochondrial aequorin intracellular $Ca^{2+}$ release (Stables et al., 1997, *Anal. Biochem.* 252:115-126; incorporated herein by reference) was performed as described (Detheux et al., 2000, *J. Exp. Med.,* 192 1501-1508; incorporated herein by reference). Briefly, cells were collected from plates in PBS containing 5 mM EDTA, pelleted and resuspended at $5 \times 10^6$ cells/ml in DMEM-F12 medium. Cells were incubated with 5 μM Coelenterazine H (Molecular Probes) for 4 hours at room temperature. Cells were then washed in DMEM-F12 medium and resuspended at a concentration of $0.5 \times 10^6$ cells/ml. Cells were then mixed with test agonist peptides or plates containing tissue extracts and the light emission was recorded for 30 sec using a Microlumat luminometer (Perkin Elmer). Results are expressed as Relative Light Units (RLU).

FIG. 17 shows the concentration response curve for the truncated PreprocHEMERIN peptide (SEQ ID NO: 73, FIG. 16) to ChemerinR expressed in CHO cells. The assay was carried out as described in the preceeding paragraph. As shown in the figure, the truncated PreprocHEMERIN molecule activates ChemerinR with an $EC_{50}$ of 4.27 nM. Results are expressed as Relative Light Units (RLU).

Example 8

Activation of Cells Expressing ChemerinR by Recombinant Chemerin

The conditioned medium of COS-7, CHO-K1 and 293 T cells transfected with pcDNA3 encoding Chemerin or pcDNA3 alone, was collected and used for aequorin assays on CHO cells expressing ChemerinR. Results are shown in FIG. 14. Increasing amounts of conditioned supernatant resulted in an increase in luminescence in aequorin system cells expressing ChemerinR.

Example 9

Production of Antibodies Specific for Chemerin and ChemerinR

Antibodies directed against Chemerin or ChemerinR were produced by repeated injections of plasmids encoding Chemerin or ChemerinR into mice. Sera were collected starting after the second injection and the titre and specificity of the antibodies was assessed by flow cytofluorometry with CHO-K1 cells transfected with the Chemerin or ChemerinR cDNA and CHO-K1 cells transfected with the cDNA of unrelated GPCR cDNA. Several sera were positive and were used for immunohistochemistry and other related applications, including flow cytometry analysis of human primary cells.

Monoclonal antibodies were obtained from immune mice by standard hybridoma technology using the NSO murine myeloma cell line as immortal partner. Supernatants were tested for anti ChemerinR antibody activity using the test used for assessing the antisera. Cells from the positive wells were expanded and frozen and the supernatants collected.

In particular, BALB/c mice were injected with 100 μg pcDNA-ChemerinR, or with the Chemerin C-terminal octapeptide FSKALPRS. Sera were tested by FACS on the CHO-ChemerinR cell line, or by ELISA for the Chemerin peptide, and immune mice were used to generate monoclonal antibodies by standard hybridoma technology, using the NSO myeloma cell line. The Ig class of selected hybridomas was determined with a mouse mAB isotyping kit (IsoStrip, Boehringer Mannheim).

FIG. 15 shows the results of experiments to characterize the antibodies raised against ChemerinR. A mixture of recombinant cells made up of ⅔ recombinant ChemerinR CHO cells and ⅓ mock-transfected CHO cells (negative control) was reacted with either a supernatant of cells expressing the anti ChemerinR 5 C1H2 monoclonal antibody (thick line) or a supernatant from cells with no known antibody activity (thin line, grey filling). After staining with FITC labeled anti mouse Ig these preparations were analyzed by flow cytofluorometry. Results are displayed as a histogram of the number of cells (Events axis) expressing a given fluorescence (FL1-H axis). Monoclonal 5C 1H2 allowed the discrimination of the ChemerinR recombinant sub-population of cells from the negative control cells, as evidenced by the relative proportions of both types of cells. The background fluorescence of the assay is given by the second staining (grey filling).

The ability of anti-chemerinR antibodies to block receptor activation by chemerin was investigated using the aequorin assay on chemerinR-expressing CHO-K1 cells. We found that two antibodies (4C7 and 1H2) were able to efficiently inhibit calcium mobilization promoted by recombinant chemerin, in a concentration-dependent manner (FIG. 26A).

Example 10

Binding Displacement Assay

For displacement experiments, ChemerinR-CHO-K1 cells (25,000 cells/tube) are incubated for 90 min. at 27° C. with 1 nM of SEAP-HIS6 or Chemerin-SEAP-HIS6 in the presence of increasing concentrations of unlabeled Chemerin in 250 μl of binding buffer (50 mM Hepes pH 7.4; 1 mM Ca $Cl_2$; 0.5% Bovine Serum Albumin (BSA) Fatty Acid-Free; 5 mM $MgCl_2$). For saturation experiments, ChemerinR-CHO-K1 cells (25,000 cells/tube) are incubated for 90 min at 27° C. with increasing concentrations of Chemerin-SEAP-HIS6 in the presence or absence of 1 μM unlabeled Chemerin. After incubation, cells are washed 5 times and lysed in 50 μl of 10 mM Tris-HCl (pH 8.0), 1% triton X100, Samples are heated at 65° C. for 10 min to inactivate cellular phosphatases. Lysates are collected by centrifugation, and alkaline phosphatase activity in 25 μl of lysate is determined by the chemiluminescence assay described above.

Example 11

Competition Binding Assay

ChemerinR expressing CHO-K1 cells were collected from plates with PBS supplemented with 5 mM EDTA, gently pelleted for 2 min at 1000×g, and resuspended in binding buffer (50 mM HEPES, pH 7.4, 1 mM $CaCl_2$, 5 mM $MgCl_2$, 0.5% BSA). Competition binding assays were performed in Minisorb tubes (Nunc), using the $^{125}$I-YHSFFFPGQFAFS (SEQ ID NO: 91) peptide as tracer (specific activity: 600 Ci/mmol, 50,000 cpm per tube), variable concentrations of competitors, and 500,000 cells in a final volume of 0.1 ml. Total binding was measured in the absence of competitor, and nonspecific binding was measured in the presence of a 100-fold excess of unlabeled ligand. Samples were incubated for 90 min at 27° C. and then bound tracer was separated by filtration through GF/B filters presoaked in 0.5% BSA. Filters were counted in a ®-scintillation counter. Binding parameters were determined with the PRISM software (Graphpad Software) using nonlinear regression applied to a one-site competition model.

The structure-function analysis of peptides derived from the C-terminus of chemerin allowed to design a bioactive peptide (YHSFFFPGQFAFS (SEQ ID NO: 91), $EC_{50}$ of 28 nM on chemerinR-expressing CHO-K1 cells, using the aequorin-based assay) that could be labeled on its N-terminus tyrosine for binding studies. This iodinated peptide was used in a competition binding assay, using the unlabeled peptide or recombinant chemerin as competitors. As shown in FIG. 23C, the Ki values were estimated to 2.5±1.2 nM (pKi: 8.82±0.38) for recombinant Chemerin (filled circles) and 12.1±4.97 nM (pKi: 7.95±0.18) for the unlabel peptide (open square) (mean±s.e.m for 3 independent experiments).

Example 12

Intracellular Cascade Assays $GTP\gamma^{35}S$ binding to membranes of cells expressing human ChemR23 was performed as described previously (Kotani et al. 2000). Briefly, membranes (10 µg) from CHO-hChemR23 cells, pretreated or not with PTX) were incubated for 15 min at room temperature in GTPγS binding buffer (20 mM HEPES pH 7.4, 100 mM NaCl, 3 mM $MgCl_2$, 3 µM GDP, 10 µg/ml saponin) containing different concentrations of peptides in 96 well microplates (Basic FlashPlates, New England Nuclear). [$^{35}S$]-GTPγS (0.1 nM, Amersham-Pharmacia) was added, microplates were shaken for one minute and further incubated at 30° for 30 min. The incubation was stopped by centrifugation of the microplate for 10 min at 800 g and 4°, and aspiration of the supernatant. Microplates were counted in a TopCount (Packard, Downers, Ill.) for 1 min per well. Functional parameters were determined with the PRISM software (Graphpad Software) using nonlinear regression applied to a sigmoidal dose-response model.

The signaling pathways activated by chemerinR were investigated in CHO-K1 cells expressing the human receptor, but not $G_{\alpha 16}$ or apoaequorin (CHO/chemerinR cells). Receptor activation was tested in a GTPγ[$_{35}S$] binding assay, using membranes from CHO/chemerinR cells and human chemerin. The results show stimulation of ChemerinR expression CHO-K1 cells ($EC_{50}$: 7.8±0.4 nM, mean±s.e.m for 4 independent experiments, FIG. 23D). Furthermore, stimulation of these cells by human Chemerin at low nanomolar concentrations resulted in the release of intracellular calcium and inhibition of cAMP accumulation (not shown), as well as phosphorylation of the p42 and p44 MAP kinases (FIGS. 23 E and F). All these effects were inhibited by Pertussis toxin pretreatment, demonstrating the involvement of $G_i$ family members. No activity of recombinant Chemerin or prochemerin was obtained in any of these assays on wild-type CHO-K1 cells (data not shown).

Example 13

Tissue Distribution of Chemerin and ChemerinR

Figure 18:
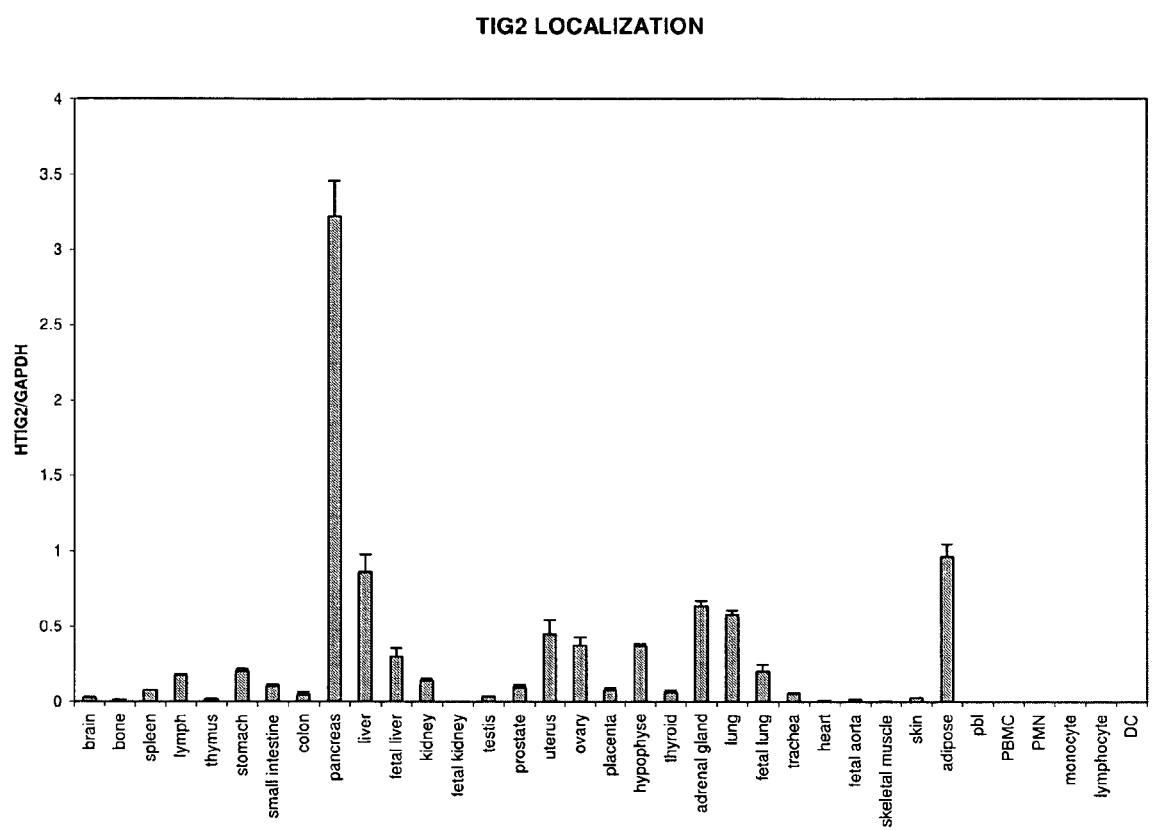
FIG. 18 shows the tissue distribution of hPreprochemerin mRNA.
Figure 19:
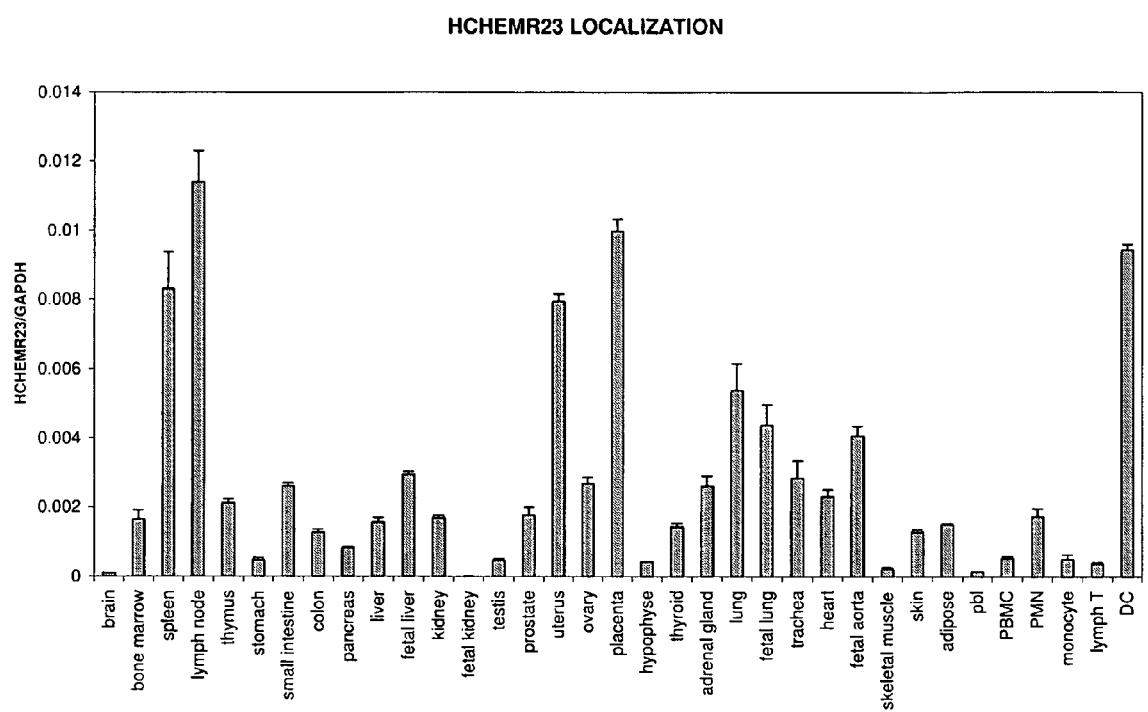
FIG. 19 shows the tissue distribution of ChemerinR mRNA.
Figure 28:
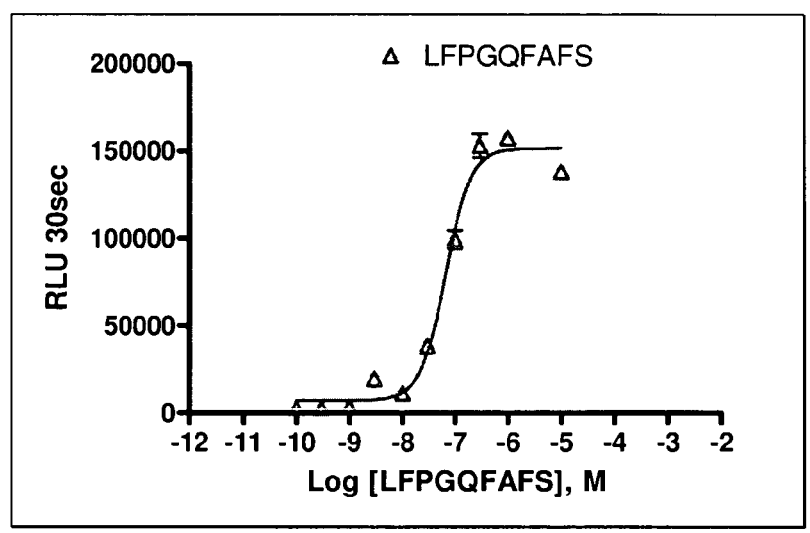
Figure 29:
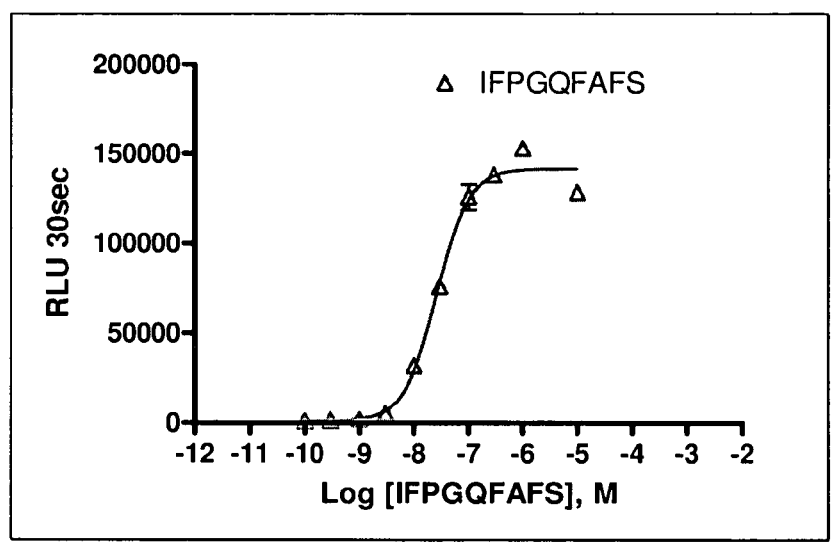
Figure 30:
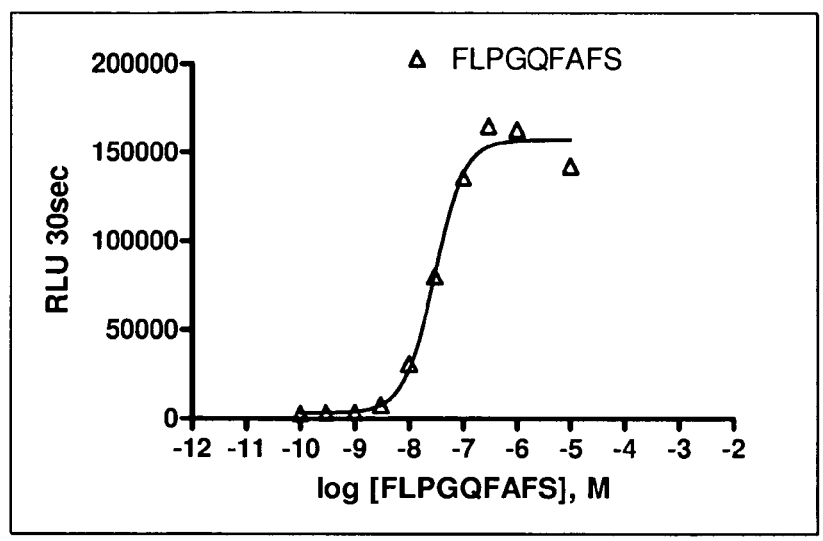
Figure 31:
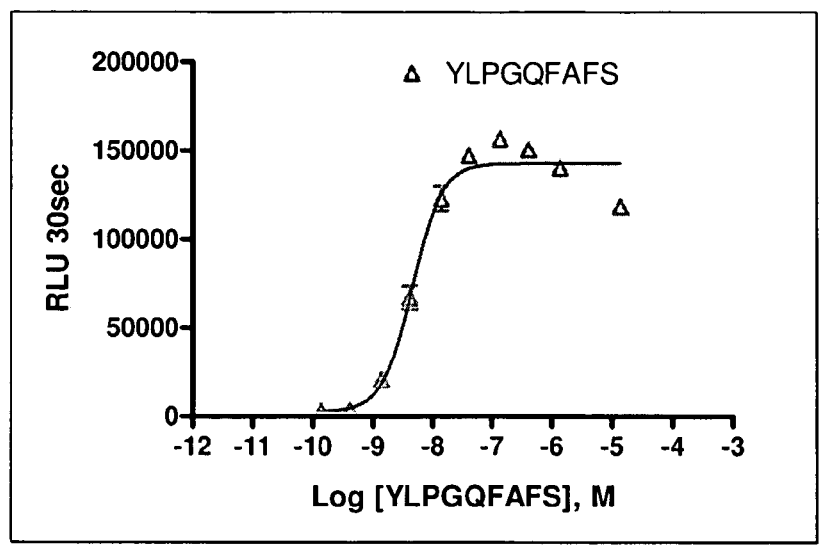
Figure 32:
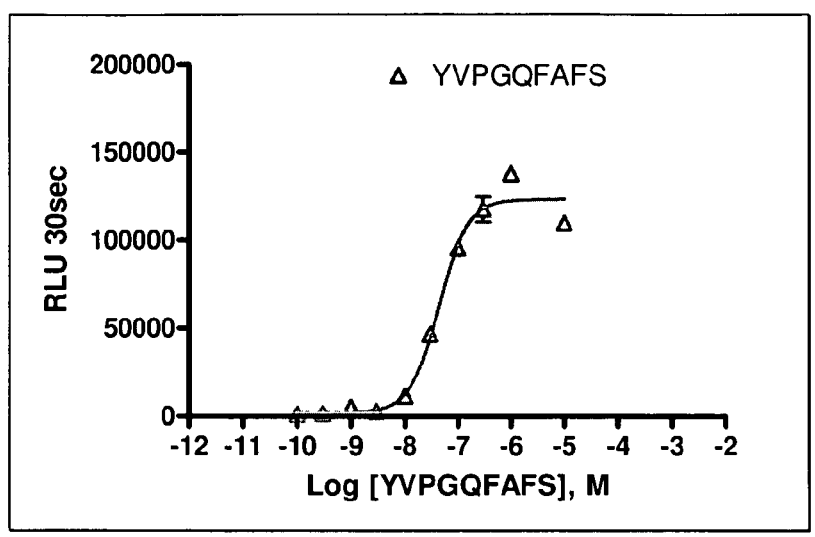
Figure 33:
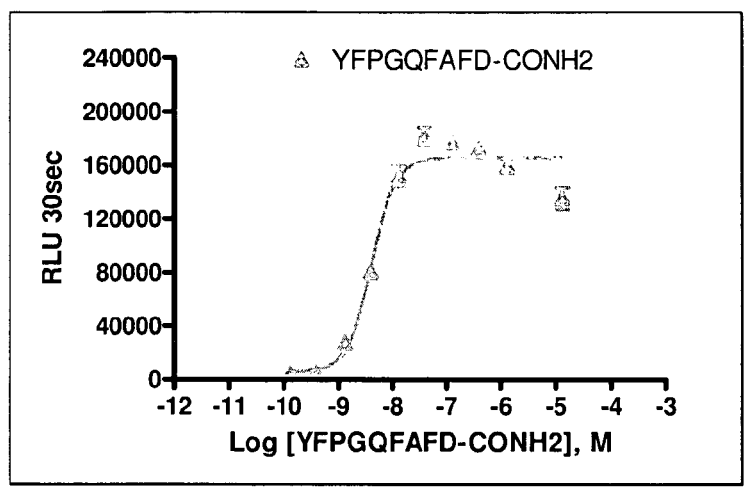

Semi-quantitative RT-PCR was performed using gene-specific primers to hCHEMERIN and ChemerinR on polyA+ RNA and total RNA from various human tissues (CLONTECH and Ambion). Briefly, total RNA from blood cells were prepared with Rneasy Mini Kit (Qiagen). The hCHEMERIN primers were forward (5'-GCAGACAAGCT-GCCGGA-3'; SEQ ID NO: 34), TaqMan probe (5'-AAC-CCGAGTGCAAAGTCAGGCCC-3'; SEQ ID NO: 36), and reverse (5'-AGTTTGATGCAGGCCAGGC-3'; SEQ ID NO: 35). The hChemerinR primers were forward (5'-GTCCCA-GAACCACCGCAG-3'; SEQ ID NO: 37), TaqMan probe (5'-TTCGCCTGGCTTACATGGCCTGC-3'; SEQ ID NO: 39), and reverse (5'-AAGAAAGCCAGGACCCAGATG-3'; SEQ ID NO: 38). Primers designed to the housekeeping gene GAPDH Forward (5'-GAAGGTGAAGGTCGGAGTC-3'; SEQ ID NO: 40), TaqMan pobe (5'-AGCTCTCCCGCCG-GCCTCTG-3'; SEQ ID NO: 42), and reverse (5'-GAA-GATGGTGATGGGATTTC-3'; SEQ ID NO: 41) were used to produced reference mRNA profiles. The distribution of hCHEMERIN and ChemerinR in various tissues is shown in FIGS. 18 and 19, respectively. The level of expression of hCHEMERIN or ChemerinR are expressed as a ratio of hCHEMERIN or ChemerinR to GAPDH reference mRNA expression.

Example 14

Expression and Pharmacological Characterization of Human Chemerin

The recombinant Chemerin protein was purified by filtration through 0.45 µm Millex filters (Millipore) and separation through a cation-exchange HPLC column (Polycat 9.6×250 mm, Vydac, 0-1 M NaCl gradient in acetate buffer pH 5). The protein concentration in active fractions was determined following SDS/PAGE, by comparison with glutathione S-transferase and lysozyme standards after silver staining.

Human Chemerin cDNA was cloned and expressed in CHO-K1 cells. The bioactive recombinant protein was purified to homogeneity from conditioned medium, and analyzed by mass spectrometry and SDS/PAGE, which confirmed C-terminal truncation after serine 157 (not shown). A monoclonal antibody, generated against a peptide (FSKALPRS, SEQ ID NO: 89) corresponding to the predicted C-terminal sequence of the gene product, was used to purify to homogeneity from CHO-K1 conditioned medium, an unprocessed form of the protein (prochemerin), which was confirmed by mass spectrometry to retain the six C-terminal aminoacids (not shown). The amount of purified recombinant Chemerin (FIG. 23A) and prochemerin (not shown) was determined by comparison with protein standards, following SDS/PAGE and silver staining. It was inferred that over 90% of prochemerin released by CHO-K1 cells was enzymatically processed into Chemerin. Comparison of the biological activity of the two purified proteins assayed in parallel on CHO-K1 cells expressing human ChemerinR (FIG. 23B) demonstrated that processed Chemerin (filled circles) was about a hundred fold more active ($EC_{50}$: 4.5±0.7 nM, mean±s.e.m. for 7 independent experiments) than unprocessed prochemerin (open circles) ($EC_{50}$: 393±116 nM, mean±s.e.m. for 3 independent experiments). The N-terminus of prochemerin and Chemerin was determined by mass spectrometry: a tryptic peptide (EL-TEAQR, 845.45 Da, SEQ ID NO: 90) corresponding to amino-acids 21 to 27 of preprochemerin was identified by sequencing (data not shown), confirming the signal peptide cleavage site predicted by the SignalP software from Expasy (http://www.cbs.dtu.dk/services/SignalP/). ChemerinR is structurally and evolutionary related to the C5a and C3a receptors, the prostaglandin D2 receptor CRTH2, and the orphan GPR1 receptor (20). These receptors, as well as a large set of other characterized and orphan receptors, including most chemokine receptors, were shown to be totally unreactive to purified human Chemerin (data not shown). The activation of ChemerinR by a set of over 200 bioactive molecules, including all currently available chemokines, C5a, C3a, fMLP, bradykinin, PAF and leukotrienes, was also tested. All these agents were unable to promote receptor activation even at concentrations significantly higher (100 nM or 1 μM) than those reported to activate their own receptors. Chemerin and its receptor appear therefore as a specific signaling system, in contrast to the situation prevailing with inflammatory chemokines and their respective receptors. In order to investigate whether proteolytic activation of prochemerin is performed intracellularly in the secretory pathway, or is an extracellular process, potentially regulated by the activation of extracellular proteases, we tested the activation of human purified prochemerin in the medium of cultured cells and conditioned media. We could show that human prochemerin can be fully converted into a form active on ChemerinR, during the incubation (at 100 nM) in the culture medium of hamster CHO-K1 cells, simian Cos-7 cells or human HEK293 cells (data not shown), as well as in conditioned media from these cells (FIG. 24A). These data indicate that prochemerin processing is performed extracellularly, and that the active Chemerin product is not degraded further by the proteolytic activity, and is therefore stable in extracellular medium. Although the protease responsible for this processing is not known, the regulation of this enzyme activity is expected to control the extracellular generation of active Chemerin in vivo.

Example 15

High Affinity Activation of ChemerinR by C-Terminus Truncated Peptide of Chemerin In order to investigate the potential effect of peptides derived from the C-terminal domain of prochemerin, we first synthesized several peptides starting at position 139 of prochemerin, after the last cysteine (Table 2), and tested their ability to trigger intracellular calcium release in a cell line coexpressing the Chemerin receptor and apoaequorin, WE have use the arquorin assay as previously described in Detheux et al. (2000 *J. Exp. Med.* 192, 1501-1508). As shown in FIG. 25A and Table 2, the peptide corresponding to the C-terminal end of prochemerin (hProchemerin-25) was not able to activate the receptor under high concentration (mean $EC_{50}$ of 160±21 μM), whereas the same peptide lacking the 6 last amino-acids (hChemerin-19) activated the Chemerin receptor with very high affinity (mean $EC_{50}$ of 16.7±3.2 nM). As described before, the recombinant prochemerin was poorly active (mean $EC_{50}$ of 393±116 nM) compared to the affinity of the processed recombinant Chemerin (mean $EC_{50}$ of 4.5±0.7 nM). These results are consistent with the previously data showing the functional importance of the C-terminal processing of the prochemerin, which allows the transformation of a low affinity precursor to a high affinity form of the ligand. Surprisingly, these data also suggest that a sequence corresponding to the last 19 C-terminus amino acids of Chemerin seems to be sufficient for providing high affinity receptor activation.

To study the accuracy of the processing of the immature form of Chemerin, we further investigated the effect of C-terminal truncated peptides variants (Table 2). As shown in FIG. 25B and Table 2, addition of a single amino-acid (h[Lys-20] Chemerin-19) to the C-terminal end of the control peptide strongly affected the affinity ($EC_{50}$ of 170 μM compared to a value of 16.7±3.2 nM for hChemerin-19). The same effect was observed after removal of at least 2 amino-acids (h[Phe18Ser19] Chemerin-19, $EC_{50}$ of 220 μM; h[Ala17Phe18Ser19] Chemerin-19, $EC_{50}$ of 130±10 μM). However, removal of only one amino-acid slightly impaired the response (h[Ser19] Chemerin-19, $EC_{50}$=97±13 nM).

From these data, the C-terminal end of the Chemerin appeared to be extremely precise, as addition of only one amino acid abrogated the high affinity intracellular calcium response. We also showed the functional importance of the Phenylalanine residue in position 18 and, more slightly, the Serine in position 19. Thus, C-terminal modification of the Chemerin seriously impaired the high affinity activation of its receptor, demonstrating the accuracy of the activating cleavage.

TABLE 2

The $EC_{50}$ value of the truncated Chemerin peptide

| SEQ ID NO | Peptide (name and sequence) | Mean EC50 |
|---|---|---|
| 52 | Human prochemerin-25 QRAGEDPHSFYFPGQFAFSKALPRS | 160 ± 21 uM |
| 53 | Human Chemerin-19 QRAGEDPHSFYFPGQFAFS | 16.7 ± 3.2 nM |
| 54 | Human [Lys20] Chemerin-19 QRAGEDPHSFYFPGQFAFSK | 170 ± uM |
| 55 | Human [ΔSer19] Chemerin-19 QRAGEDPHSFYFPGQFAF | 97 ± 13 nM |
| 56 | Human [ΔPhe18Ser19] Chemerin-19 QRAGEDPHSFYFPGQFA | 220 uM |
| 57 | Human [ΔAla17Phe18Ser19] Chemerin-19 QRAGEDPHSFYFPGQF | 130 ± 10 uM |
| 58 | Human [ΔPhe16Ala17Phe18Ser19] Chemerin-19 QRAGEDPHSFYFPGQ | inactif |
| 59 | Human Chemerin-7 PGQFAFS | 220 ± 100 uM |
| 60 | Human Chemerin-8 FPGQFAFS | 2 ± 1 uM |
| 61 | Human Chemerin-9 YFPGQFAFS | 7 ± 0.25 nM |
| 62 | Human Chemerin-10 FYFPGQFAFS | 8.2 ± 2 nM |
| 63 | Human Chemerin-12 HSFYFPGQFAFS | 12.2 ± 3.4 nM |
| 64 | Human Chemerin-13 PHSFYFPGQFAFS | 14 nM |
| 65 | Human [Ala-1] Chemerin-9 AFPGQFAFS | 496 ± 80 nM |
| 66 | Human [Ala-2] Chemerin-9 YAPGQFAFS | 155.3 ± 41.6 nM |
| 67 | Human [Ala-3] Chemerin-9 YFAGQFAFS | 42.5 ± 7.5 nM |
| 68 | Human [Ala-5] Chemerin-9 YFPGAFAFS | 35.8 ± 5.9 nM |
| 69 | Human [Ala-6] Chemerin-9 YFPGQAAFS | 5 ± 1 uM |
| 70 | Human [Ala-8] Chemerin-9 YFPGQFAAS | 38 ± 7 uM |

TABLE 2-continued

The EC$_{50}$ value of the truncated Chemerin peptide

| SEQ ID NO | Peptide (name and sequence) | Mean EC50 |
|---|---|---|
| 71 | Human [Ala-9] Chemerin-9 YFPGQFAFA | 48.3 ± 5.7 nM |

Example 16

The Shorter C-Terminal Nonapeptide YFPGQFAFS (SEQ ID NO: 61) has a High Affinity on ChemerinR We then determined the minimum length of the C-terminal fragment able to activate the Chemerin receptor with high potency. Successive truncations of the N-terminal domain of the hChemerin-19 peptide were synthesized and tested using the aequorin assay (FIG. 25C). Truncations from residue 1 to residue 10 (hChemerin-17 to hChemerin-9, FIG. 20 and EC$_{50}$ values in table 2) did not affect intracellular calcium signaling. However, removal of the Tyrosine residue in position 11 (hChemerin-8) resulted in a severely loss of affinity for the receptor (EC$_{50}$ of 2±1 µM compared to a value of 16.7±3.2 nM for the control peptide: Human chemerin-19), and the response was completely abrogated for shorter peptide (hChemerin-7, EC$_{50}$ of 220±100 µM). These results indicated that only the last 9 amino acids of Chemerin are necessary for high affinity receptor activation, as the EC$_{50}$ of the nonapeptide is 7±0.25 nM, which is in the same range to the affinity of the recombinant Chemerin.

Example 17

Aromatic Residues in Chemerin C-Terminus are Necessary for ChemerinR Activation

Since multiple residues within the last 9 amino acids sequence of Chemerin appeared to be important for receptor activation, we examined the relative contribution of each amino acid of the YFPGQFAFS (SEQ ID NO: 61) peptide in Chemerin receptor activation, by using an alanine-scanning mutagenesis approach. Eight different alanine-substituted hChemerin-9 analogs were synthesized and tested for intracellular calcium accumulation. As shown in FIG. 25D and Table 2, the EC$_{50}$ of the Q5A, P3A and S9A mutated peptides was shifted to higher concentrations (EC$_{50}$ of 35.8±5.9 nM, 42.5±7.5 nM and 48.3±5.7 nM respectively) as compared with the control peptide (mean EC$_{50}$ of 7±0.25 nM). The EC$_{50}$ of the F2A and Y1A peptides was more severely affected (EC$_{50}$ of 155.3±41.6 nM and 496±80 nM, respectively), and alanine substitution of Phe 6 and Phe 8 dramatically impaired the functional response of Chemerin receptor (EC$_{50}$ of 5±1 µM and 38±7 µM, respectively). These data suggested that aromatic Y1, F2, F6 and F8 residues play an important role in receptor activation.

Example 18

Chemotaxis and Ca$^{2+}$ Mobilization Assays on Primary Cells

Monocyte-derived DCs were generated by GM-CSF (50 ng/ml) and IL-13 (20 ng/ml) stimulation as previously described (17). Maturation of DCs was achieved following stimulation with 100 ng/ml LPS. Macrophages were obtained by incubating monocytes in Petriperm dishes (Haereus) for 6 days in RPMI supplemented with 10% FCS and 10 ng/ml MCSF. Cell migration was evaluated using a 48-well microchemotaxis chamber technique as described (18). For Ca$_{2+}$ mobilization assays, monocyte-derived DCs or macrophages ($10^7$ cells/ml in HBSS without phenol red but containing 0.1% BSA) were loaded with 5 µM FURA-2 (Molecular Probes) for 30 min at 37° C. in the dark. The loaded cells were washed twice, resuspended at $10^6$ cells/ml, kept for 30 min at 4° C. in the dark with or without the blocking 4C7 monoclonal antibody (10 µg/ml), and transferred into the quartz cuvette of a luminescence spectrometer LS50B (PerkinElmer). Ca$^{2+}$ mobilization in response to recombinant Chemerin was measured by recording the ratio of fluorescence emitted at 510 nm after sequential excitation at 340 and 380 nm.

The biological function of Chemerin was further investigated on leukocyte populations. In accordance to the coupling of human ChemerinR through the G$_i$ class of G proteins, its structural relatedness to chemoattractant receptors, and its expression in antigen-presenting cells, we showed that Chemerin acted as a chemotactic factor for these cells. Dendritic cells and macrophages were differentiated in vitro from human monocytes. Human recombinant Chemerin promoted in vitro migration of macrophages and immature dendritic cells (FIGS. 26 B, C, and F), whereas no chemotaxis of mature dendritic cells was observed (data not shown). Maximal chemotactic responses were obtained for concentrations of 100 µM to 1 nM, according to the batch of recombinant Chemerin. Such bell-shaped chemotactic response, with a maximum corresponding to concentrations below the EC$_{50}$ observed in other functional assays, is typically observed for other chemotactic factors such as chemokines. The effect was completely abolished following treatment with Pertussis toxin (FIGS. 26 C and F), demonstrating the involvement of the G$_i$ class of G proteins. Migration of macrophages and dendritic cells was also inhibited by the antiChemerinR monoclonal antibody 4C7 (FIGS. 26 C and F) without affecting RANTESinduced cell migration, demonstrating that the effect is specifically mediated by the ChemerinR. A checkerboard analysis showed that, when equal concentrations of Chemerin were present in both the lower and upper wells, no significant increase in cell migration was observed (FIGS. 26 C and F). Thus, the migration of macrophages and immature dendritic cells induced by Chemerin is essentially a chemotactic effect rather than chemokinesis. We also investigated whether recombinant Chemerin could induce Ca$^{2+}$ mobilization in antigen-presenting cells. As expected, intracellular Ca$^{2+}$ levels increased in immature dendritic cells in response to recombinant Chemerin (FIG. 26D), whereas the 4C7 antibody inhibited the Ca$_{2+}$ response (FIG. 26E). Similar observations were made for macrophages (FIGS. 26 G and H).

Example 19

Bioactive Chemerin Concentration in Human Samples

In order to investigate whether chemerin is frequently generated in pathological situations in human, we fractionated a set of inflammatory fluids and assayed the chemerin content by measuring the biological activity of the fractions on chemerinR, as compared to a standard curve made with purified recombinant chemerin. Significant levels of active chemerin, well within the active range (33 to 358 ng/ml, corresponding to 2 to 23 nM), were found in the majority of ascitic fluids resulting from ovary cancer, but also in ascitic fluids resulting from a liver cancer and from an ovary hyperstimulation syndrome, as well as in a pool of articular fluids from arthritic patients (Table 3). Interestingly, active chemerin was not detected in articular fluid pooled from patients with arthrosis (Table 3), nor in fractions from human hemofiltrate (not shown), demonstrating that its presence is linked to inflammatory situations.

The amount of Chemerin in ascitic (samples 1-17) and articular (samples 18 and 19) fluids was estimated following two fractionation steps, by assaying the fractions on ChemerinR-expressing cells, using the aequorin-based assay and a standard curve made with purified recombinant human Chemerin. Articular fluids from arthritis and arthrosis patients were pooled for measurement, following centrifugation. O. H.S.: ovarian hyperstimulation syndrome. n.d.: not detectable (the limit of detection in the assay conditions is given).

TABLE 3

Bioactive Chemerin concentration in human samples.

| Sample | Pathology | Chemerin (ng/ml) |
|---|---|---|
| 1 | Ovary Carcinoma | 74 |
| 2 | Ovary Carcinoma | 73 |
| 3 | Ovary Carcinoma | 104 |
| 4 | Ovary Carcinoma | 92 |
| 5 | Ovary Carcinoma | n.d. (<10) |
| 6 | Ovary Carcinoma | 82 |
| 7 | Ovary Carcinoma | 103 |
| 8 | Ovary Carcinoma | 43 |
| 9 | Ovary Carcinoma | 87 |
| 10 | Ovary Carcinoma | n.d. (<10) |
| 11 | Ovary Carcinoma | 90 |
| 12 | Ovary Carcinoma | 33 |
| 13 | Ovary Carcinoma | 57 |
| 14 | Ovary Carcinoma | 87 |
| 15 | Ovary Carcinoma | 62 |
| 16 | Ovary Carcinoma | 37 |
| 17 | O.H.S. | 116 |
| 18 | Arthritis | 358 |
| 19 | Arthrosis | n.d. (<1) |

Example 20

In Vivo Gene Therapy in Mouse

B16-F0 Melanoma Model.

B16-F0 melanoma cells (ATCC) were transfected with the pEFIN3-mouse chemerin plasmid using FuGene6, and selected with 800 µg/ml G418. Clones were characterized by assaying the conditioned medium on chemerinRexpressing cells. In vitro proliferation rate was determined by BrdU incorporation as described[30]. For in vivo studies, cells were washed twice with PBS, and grafted ($6 \times 10_5$ cells in 0.1 ml PBS) subcutaneously into the back of 10-week-old C57B16 mice (5 to 11 mice per group, Harlan, The Netherlands). Perpendicular tumor diameters (D and d) were measured every 2 days, and the volume was estimated as $V=\pi(d/2)(D/2)(d/2)$. Statistical analysis was performed by using the unpaired non parametric Mann-Whitney test. For microscopic analysis, tumors were embedded in OCT, snap-frozen in −80° C. isopentane and cut at 12 µm. Sections were stained with hematoxylin-eosin (HE) for routine analysis. All animal procedures were approved by the ethical committee of the Medical School of the Université Libre de Bruxelles.

The biological function of Chemerin was further investigated in a mouse model in vivo. In accordance to the coupling of human ChemerinR through the $G_1$ class of G proteins, its structural relatedness to chemoattractant receptors, and its expression in dendritic cells, Chemerin acted as a chemotactic factor for these cells. Dendritic cells were differentiated in vitro from human monocytes. Human recombinant Chemerin was chemotactic in vitro for immature, but not mature, dendritic cells, with a maximal activity at 1 nM (See example 18 of the present application).

As active Chemerin was originally isolated from tumoral ascitis, we evaluated the significance of this expression in a tumor context, by investigating the consequence of Chemerin expression in a mouse tumor model in vivo. The mouse prochemerin and ChemerinR cDNAs were cloned. Following their expression in CHO-K1 cells, functional assays demonstrated that the human and mouse recombinant ligands were equally active on both the human and mouse receptors (data not shown). The melanoma cell line B16F0 was transfected with a bicistronic expression vector containing the mouse Chemerin cDNA (or a control vector), and stable cell lines were established. The expression of bioactive Chemerin was confirmed by measuring the activity of conditioned medium. The two selected cell lines released over a period of 24 hours about 125 ng/ml active Chemerin in the culture medium. Expression of Chemerin did not modify the growth rate of the cell lines, as assessed by measuring the proportion of cells in the various phases of the cell cycle (FIGS. 27A-C), or by directly counting cells over time (data not shown). However, following subcutaneous graft of the cells to syngenic mice, the phenotype of the developing tumors was profoundly modified by Chemerin expression. In three independent series, all mice receiving wild-type B 16F0 cells developed a rapidly growing tumor, in accordance with the literature, while a number of mice receiving Chemerin-expressing cells did not develop tumors up to four weeks after the graft. By combining the three series, 5 out of 24 mice grafted with Chemerin-expressing cells did not develop tumors (versus 0/24 in the control group, p<0.05, Fisher test). The size of the developing tumors was also much smaller for the Chemerin group (an average reduction of 70% 21-24 days after the graft of cells, FIG. 27D). The difference was significant from day 10 after the graft (p=0.02 to 0.004 according to time points, non-parametric Mann-Whitney test). Macroscopic analysis at the end of the observation period (12 to 30 days) revealed a number of phenotypic differences between the two groups. Chemerin-producing tumors were characterized by a more abundant vascularization, and a much lower extent of necrotic areas. These phenotypic differences were not the consequence of a difference in the size of the tumors, as they were observed as well following the selection of rare size-matched tumors belonging to the two groups. Microscopic analysis, following hematoxylin-eosin staining, confirmed these observations, particularly the major difference in the extent of necrosis, that occupies the largest part of control tumors, while being rare in Chemerin-producing tumors (FIGS. 27 E and F).

The invention claimed is:

1. An isolated nucleic acid molecule encoding the polypeptide sequence of SEQ ID NO: 14.

2. The isolated nucleic acid molecule of claim 1, wherein said nucleic acid molecule consists of the sequence of SEQ ID NO: 13.

3. An isolated nucleic acid molecule encoding a Chemerin polypeptide that specifically binds to a ChemerinR polypeptide of SEQ ID NO: 2, wherein the nine C-terminal amino acids of said Chemerin polypeptide are set forth in SEQ ID NO: 61.

4. The isolated nucleic acid molecule of claim 3, wherein the sequence of said Chemerin polypeptide is set forth in SEQ ID NO: 14.

5. The isolated nucleic acid molecule of claim 3, wherein the sequence of said Chemerin polypeptide is set forth in SEQ ID NO: 53.

6. The isolated nucleic acid molecule of claim 3, wherein said nucleic acid molecule comprises the sequence of SEQ ID NO: 13.

7. An isolated host cell comprising a recombinant nucleic acid molecule encoding the polypeptide sequence of SEQ ID NO: 14.

8. A method for producing the polypeptide of SEQ ID NO: 14 comprising culturing the host cell of claim 7 under conditions wherein said recombinant nucleic acid molecule is expressed and recovering the polypeptide encoded by said isolated nucleic acid molecule.

9. An isolated host cell comprising a recombinant nucleic acid molecule encoding a Chemerin polypeptide that specifically binds to the ChemerinR polypeptide of SEQ ID NO: 2, wherein the nine C-terminal amino acids of said Chemerin polypeptide are set forth in SEQ ID NO: 61.

10. A method for producing a Chemerin polypeptide, said method comprising culturing the host cell of claim 9 under conditions wherein said recombinant nucleic acid molecule is expressed and recovering the polypeptide encoded by said isolated nucleic acid molecule.

* * * * *